(12) United States Patent
Felding et al.

(10) Patent No.: US 8,324,394 B2
(45) Date of Patent: *Dec. 4, 2012

(54) SUBSTITUTED ACETOPHENONES USEFUL AS PDE4 INHIBITORS

(75) Inventors: Jakob Felding, Charlottenlund (DK); Simon Feldbæk Nielsen, Herlev (DK)

(73) Assignee: Leo Pharma A/S, Ballerup (DK)

( * ) Notice: Subject to any disclaimer, the term of this patent is extended or adjusted under 35 U.S.C. 154(b) by 0 days.

This patent is subject to a terminal disclaimer.

(21) Appl. No.: 13/406,932

(22) Filed: Feb. 28, 2012

(65) Prior Publication Data

US 2012/0165539 A1 Jun. 28, 2012

Related U.S. Application Data

(62) Division of application No. 12/520,325, filed as application No. PCT/DK2007/000564 on Dec. 21, 2007, now Pat. No. 8,148,537.

(60) Provisional application No. 60/871,689, filed on Dec. 22, 2006, provisional application No. 60/945,470, filed on Jun. 21, 2007.

(51) Int. Cl.
*C07D 213/46* (2006.01)
*A61K 31/44* (2006.01)

(52) U.S. Cl. ........................................ 546/340; 514/357

(58) Field of Classification Search ........................ None
See application file for complete search history.

(56) References Cited

U.S. PATENT DOCUMENTS 6,514,996 B2 2/2003 Ohshima et al.

FOREIGN PATENT DOCUMENTS

| EP | 0 943 613 A1 | 9/1999 |
|---|---|---|
| WO | WO 95/20578 A1 | 8/1995 |
| WO | WO 2006/040645 A1 | 4/2006 |
| WO | WO 2006/135828 A2 | 12/2006 |

OTHER PUBLICATIONS

Baumer, W. Inflamm. & Allergy Drug Targets 2006, vol. 6, pp. 17-26.
Hardman, J., ed., Goodman and Gilman's The Pharmacological Basis of Therapeutics, McGraw-Hill 1996, p. 44.
Patani, G. et al., Chem. Rev. 1996, vol. 96, pp. 3147-3176.
Silva, A. et al., Mini-Revs in Med. Chem., 2005, vol. 5, 893-914.
Vippagunta, S. Adv. Drug. Deliv. Rev 2001 vol. 48, pp. 3-26.

*Primary Examiner* — Janet Andres
*Assistant Examiner* — Heidi Reese
(74) *Attorney, Agent, or Firm* — Birch, Stewart, Kolasch & Birch, LLP

(57) ABSTRACT

The present invention relates to a compound according to formula: (I); wherein $X_1, X_2, X_3, X_4$ and $X_5$ independently of each other represent —CH— or N; or $X_3, X_4$ and $X_5$ independently of each other represent —CH— or N, and $X_1$ and $X_2$ independently of each other represent C and form part of an additional 6-membered aromatic ring; $R_1$ represents hydrogen, alkyl, alkenyl, alkynyl, haloalkyl, hydroxyallyl, or alkylcarbonyl, all of which are optionally substituted; $R_2$ and $R_3$ independently represent hydrogen, —CH$_2$—C(O)NR—R', alkyl, cycloalkyl, alkenyl, cycloalkenyl, alkynyl, haloalkyl, hydroxyalkyl, heterocycloalkenyl, alkylaryl, alkylalkoxycarbonyl, alkylcarbonyloxy, or alkoxyalkyl, all of which are optionally substituted; $R_{11}$ represents hydrogen, halogen, cyano, amino, alkoxy or alkylamino, $X_1$-$X_5$ represent —CH— or N, including N-oxides, enantiomers and diastereomers; and pharmaceutically acceptable salts, hydrates, or solvates thereof. The invention relates further to processes for the preparation of said compounds, to said compounds for use in therapy, to pharmaceutical compositions comprising said compounds, to methods of treating diseases, e.g. dermal diseases, with said compounds, and to the use of said compounds in the manufacture of medicaments.

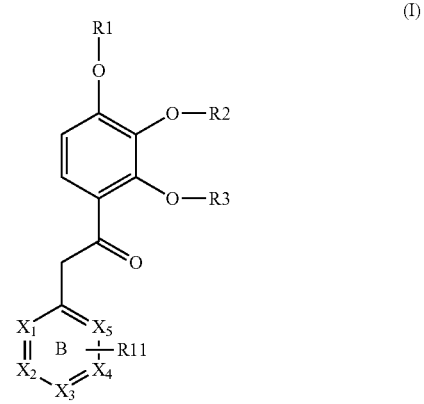

(I)

3 Claims, No Drawings

SUBSTITUTED ACETOPHENONES USEFUL AS PDE4 INHIBITORS

CROSS REFERENCE

The present application is a 37 C.F.R. §1.53(b) divisional of, and claims priority to, U.S. application Ser. No. 12/520,325 filed Jul. 29, 2009 now U.S. Pat. No. 8,148,537. application Ser. No. 12/520,325 is the national phase under 35 U.S.C. §371 of International Application No. PCT/DK2007/000564, filed on Dec. 21, 2007. Priority is also claimed to U.S. Application No. 60/871,689 filed on Dec. 22, 2006 and U.S. Application No. 60/945,470 filed on Jun. 21, 2007. The entire contents of each of these applications is hereby incorporated by reference.

FIELD OF THE INVENTION

This invention relates to novel substituted acetophenones and derivatives thereof, processes for the preparation thereof, to said compounds for use in therapy, to pharmaceutical compositions comprising said compounds, to methods of treating diseases with said compounds, and to the use of said compounds in the manufacture of medicaments.

BACKGROUND OF THE INVENTION

Phosphodiesterases are enzymes that catalyse the hydrolysis of cyclic AMP and/or cyclic GMP in cells to 5-AMP and 5-GMP, respectively, and as such they are critical to cellular regulation of cAMP or cGMP levels. Of the 11 phosphodiesterases identified so far, phosphodiesterase (PDE) 4, PDE7 and PDE8 are selective for cAMP. PDE4 is the most important modulator of cAMP expressed in immune and inflammatory cells such as neutrophils, macrophages and T-lymphocytes (Z. Huang and J. A. Mancini, *Current Med. Chem.* 13, 2006, pp. 3253-3262). As cAMP is a key second messenger in the modulation of inflammatory responses, PDE4 has been found to regulate inflammatory responses of inflammatory cells by modulating proinflammatory cytokines such as TNFα, IL-2, IFN-γ, GM-CSF and LTB4. Inhibition of PDE4 has therefore become an attractive target for the therapy of inflammatory diseases such as asthma, chronic obstructive pulmonary disease (COPD), rheumatoid arthritis, atopic dermatitis, Crohn's disease etc. (M. D. Housley et al., *Drug Discovery Today* 10 (22), 2005, pp. 1503-1519). As atopic dermatitis (AD) patients have increased PDE-activity, PDE4-inhibition would also appear to be a viable treatment of AD (Journal of Investigative Dermatology (1986), 87(3), 372-6). The PDE4 gene family consists at least of four genes, A, B, C and D, which have a high degree of homology (V. Boswell Smith and D. Spina, *Curr. Opinion Investig. Drugs* 6(11), 2006, pp. 1136-1141). The four PDE4 isoforms are differentially expressed in different tissues and cell types. Thus, PDE4B is predominantly expressed in monocytes and neutrophils, but not in cortex and epithelial cells, while PDE4D is expressed in lung, cortex, cerebellum and T-cells (C. Kroegel and M. Foerster, *Exp. Opinion Investig. Drugs* 16(1), 2007, pp. 109-124). It has been speculated that inhibition of PDE4D in the brain is associated with the adverse effects found when administering PDE4 inhibitors clinically, primarily nausea and emesis, whereas inhibition of PDE4B is associated with anti-inflammatory effects (B. Lipworth, *Lancet* 365, 2005, pp. 167-175). However, the PDE inhibitors developed so far are not believed to be specific for any of the four PDE4 isoforms. Numerous PDE4 inhibitors have been studied for their therapeutic effect on inflammatory diseases, primarily asthma and COPD.

The first of these, theophylline, is a weak, non-selective phosphodiesterase inhibitor used in the treatment of respiratory diseases such as asthma and COPD. Treatment with theophylline may, however, give rise to both mild and severe adverse effects, e.g. arrhythmia and convulsions, restricting the clinical utility of theophylline (Kroegel and Foerster, supra). As phosphodiesterase has remained an attractive target for anti-inflammatory therapy, several other, more selective PDE4 inhibitors have been developed and investigated in a clinical setting. The clinical development of many of the first-generation PDE4 inhibitors such as rollpram was discontinued due to dose-limiting side effects, primarily nausea and emesis. Second-generation PDE4 inhibitors with apparently less pronounced adverse effects are currently in clinical trials (Houslay, supra). PDE-4 inhibitors are for example disclosed in EP 0771794 and EP 0943613. WO95/20578 and WO 96/31476 disclose structurally different 4-substituted-3,5-dichloropyridines which are inhibitors of cyclic AMP phosphodiesterase. There is a continued need for developing novel PDE4 inhibitors which have a more favourable therapeutic window, i.e. fewer adverse effects, while retaining their therapeutic anti-inflammatory effect. An overview of preclinical and clinical trials with selective PDE4 inhibitors, including such inhibitors aimed for the treatment of for psoriasis, was recently given in Inflammation & Allergy: Drug Targets, 2007, 6(1), 17-26.

SUMMARY OF THE INVENTION

The inventors have surprisingly found that novel compounds of the present invention exhibit selective PDE4 inhibitory activity (having a >10 times reduced activity against PDE 1, 2, 3, 5, 7, 8, 9, 10, or 11), which may be useful as therapeutic agents for inflammatory allergic diseases such as bronchial asthma, allergic rhinitis, and nephritis; autoimmune diseases such as rheumatoid arthritis, multiple sclerosis, inflammatory Bowel disease, Crohn's disease, and systemic lupus erythematosus; diseases of the central nervous system such as depression, amnesia, and dementia; organopathy associated with ischemic reflux caused by cardiac failure, shock, and cerebrovascular diseases, and the like; insulin-resistant diabetes; wounds; AIDS, and the like.

Compounds of the present invention may also be beneficial in preventing, treating or ameliorating a variety of diseases, such as dermal diseases or conditions, such as proliferative and inflammatory skin disorders and in particular psoriasis, epidermal inflammation, alopecia, skin atrophy, steroid induced skin atrophy, skin ageing, photo skin ageing, acne, dermatitis, atopic dermatitis, seborrheic dermatitis, contact dermatitis, urticaria, pruritis, and eczema.

Compounds of the present invention may also have advantageous properties such as low cytotoxicity, reduced HERG inhibition, low genotoxicity, reduced skin irritation, improved metabolic stability properties and metabolic elimination properties, dermal delivery properties, systemic exposure characteristics after dermal delivery, all of which may make them especially suitable to be used as active pharmaceutical ingredients in drug formulations for the treatment of dermal diseases.

Accordingly, the present invention relates to a compound according to formula I

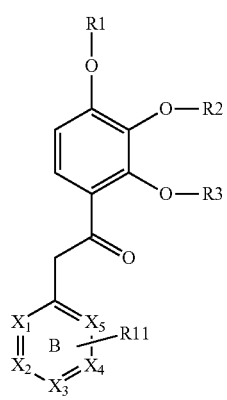

wherein $X_1$, $X_2$, $X_3$, $X_4$ and $X_5$ independently of each other represent —CH— or N;

or $X_3$, $X_4$ and $X_5$ independently of each other represent —CH— or N, and $X_1$ and $X_2$ independently of each other represent C and form part of an additional 6-membered aromatic ring;

wherein $R_1$ represents alkyl, alkenyl, alkynyl, haloalkyl, hydroxyalkyl, or alkylcarbonyl, all of which are optionally substituted by one or more, same or different substituents selected from $R_4$, or $R_1$ represents hydrogen;

$R_2$ represents alkyl, cycloalkyl, alkenyl, cycloalkenyl, alkynyl, haloalkyl, hydroxyalkyl, heterocycloalkenyl, alkylaryl, arylalkyl, alkylalkoxycarbonyl, alkylcarbonyloxy, or alkoxyalkyl, all of which are optionally substituted by one or more, same or different substituents selected from $R_5$; or $R_2$ represents hydrogen or —CH$_2$—C(O)NR$_9$—R$_{12}$;

$R_3$ represents alkyl, cycloalkyl, alkenyl, cycloalkenyl, alkynyl, haloalkyl, hydroxyalkyl, heterocycloalkenyl, alkylaryl, arylalkyl, alkylalkoxycarbonyl, alkylcarbonyloxy, or alkoxyalkyl, all of which are optionally substituted by one or more, same or different substituents selected from $R_6$; or $R_3$ represents hydrogen, —CH$_2$—C(O)-heterocycloalkyl or —CH$_2$—C(O)NR$_9$—R$_{12}$;

$R_4$ represents hydrogen, alkyl, alkenyl, alkynyl, halogen, oxo, alkoxy, hydroxy, or haloalkyl;

$R_5$ represents alkylaryl, carboxy, alkyl, alkenyl, cycloalkenyl, alkynyl, haloalkyl, cycloalkyl, cycloalkenyl, carbamoyl, hydroxyalkyl, aryloxy, alkoxycarbonyloxy, alkoxycarbonyl, alkoxy, alkoxyalkyl, aryl, a heterocyclic ring, aminocarbonyl, alkylthio, alkylcarbonylamino, hydroxy, alkylcarbonyl, arylcarbonyl, alkylcarbonyloxy, or amino, all of which are optionally substituted by one or more, same or different substituents selected from $R_7$;

or $R_5$ represents hydrogen, oxo, halogen, cyano, or nitro;

$R_6$ represents alkylaryl, carboxy, alkyl, alkenyl, cycloalkenyl, alkynyl, haloalkyl, cycloalkyl, cycloalkenyl, carbamoyl, hydroxyalkyl, aryloxy, alkoxycarbonyloxy, alkoxycarbonyl, alkoxy, alkoxyalkyl, aryl, a heterocyclic ring, aminocarbonyl, alkylthio, alkylcarbonylamino, arylcarbonyl, hydroxy, alkylcarbonyl, alkylcarbonyloxy, or amino, all of which are optionally substituted by one or more, same or different substituents selected from $R_8$;

or $R_6$ represents hydrogen, oxo, halogen, cyano, or nitro;

$R_7$ represents alkyl, alkenyl, cycloalkyl, cycloalkenyl, alkynyl, alkoxy, haloalkyl, alkylthio, heterocycloalkenyl, heterocycloalkyl, aryl, alkylcarbonyl, heteroaryl, aryloxy, alkoxycarbonyl, hydroxyalkyl, amino, hydroxy, or carboxy; all of which are optionally substituted by one or more, same or different substituents selected from $R_{10}$;

or $R_7$ represents hydrogen, halogen, or oxo;

$R_8$ represents alkyl, alkenyl, cycloalkyl, cycloalkenyl, alkynyl, alkoxy, haloalkyl, alkylthio, alkylsulfonyl, alkylsulfinyl, heterocycloalkenyl, heterocycloalkyl, aryl, alkylcarbonyl, heteroaryl, aryloxy, alkoxycarbonyl, hydroxyalkyl, amino, hydroxy, or carboxy; all of which are optionally substituted by one or more, same or different substituents selected from $R_{10}$;

or $R_8$ represents hydrogen, halogen, or oxo;

$R_9$ represents hydrogen, alkyl, haloalkyl, or hydroxyalkyl;

$R_{10}$ represents hydrogen, alkyl, oxo, hydroxy, halogen, carboxy, amino, alkoxy, haloalkyl, or hydroxyalkyl;

$R_{11}$ represents one or more, same or different substituents selected from hydrogen, halogen, cyano, amino, alkyl, methylsulfinyl, methylsulfonyl, amino, cyano, or alkoxy;

$R_{12}$ represents alkylaryl, arylalkyl, carboxy, alkyl, alkenyl, alkynyl, haloalkyl, cycloalkyl, cycloalkenyl, carbamoyl, hydroxyalkyl, aryloxy, alkoxycarbonyloxy, alkoxycarbonyl, alkoxy, alkoxyalkyl, aryl, a heterocyclic ring, aminocarbonyl, alkylthio, alkylcarbonylamino, hydroxy, alkylcarbonyl, arylcarbonyl, alkylcarbonyloxy, or amino, all of which are optionally substituted by one or more, same or different substituents selected from $R_8$, or $R_{12}$ represents hydrogen;

with the proviso $R_1$, $R_2$ and $R_3$ cannot all be methyl; with the proviso that when $R_2$ and $R_3$ are both hydrogen, $R_1$ cannot be methyl or hydrogen;

with the proviso that when $R_1$ is methyl or hydrogen, $R_2$ is methyl and $R_3$ is hydrogen, then ring B cannot be phenyl;

and pharmaceutically acceptable and physiologically cleavable esters, pharmaceutically acceptable salts, hydrates, N-oxides or solvates thereof.

In another aspect, the invention relates to a pharmaceutical composition comprising a compound of general formula I as defined herein together with a pharmaceutically acceptable vehicle or excipient or pharmaceutically acceptable carrier(s), optionally together with one or more other therapeutically active compound(s).

In yet another aspect, the invention relates to the use of a compound according to formula I as defined herein, and pharmaceutically acceptable and physiologically cleavable esters, pharmaceutically acceptable salts, hydrates, N-oxides or solvates thereof, in the manufacture of a medicament for the prophylaxis, treatment or amelioration of dermal diseases or conditions, or acute or chronic cutaneous wound disorders.

In yet another aspect, the invention relates to a method of preventing, treating or ameliorating dermal diseases or conditions, or acute or chronic cutaneous wound disorders, the method comprising administering to a person suffering from at least one of said diseases an effective amount of one or more compounds of formula I as defined herein and pharmaceutically acceptable and physiologically cleavable esters, pharmaceutically acceptable salts, hydrates, N-oxides or solvates thereof;

optionally together with a pharmaceutically acceptable carrier or one or more excipients, optionally in combination with other therapeutically active compounds.

In yet another aspect, the present invention relates to a method for the preparation or manufacture of a compound of general formula I comprising a method as anywhere described herein, such as method a), b), c) d), or such as any one of the general methods or procedures described in the examples or preparations herein, and optionally further processing of a compound obtained, to give a compound of general formula I as anywhere defined herein.

DETAILED DESCRIPTION OF THE INVENTION

The term "hydrocarbon radical" is intended to indicate a radical containing only hydrogen and carbon atoms, it may contain one or more double and/or triple carbon-carbon bonds, and it may comprise cyclic moieties in combination with branched or linear moieties. Said hydrocarbon comprises 1-20 carbon atoms, and preferably comprises 1-12, e.g. 1-6, e.g. 1-4, e.g. 1-3, e.g. 1-2 carbon atoms. The term includes alkyl, alkenyl, cycloalkyl, cycloalkenyl, alkynyl and aryl, as indicated below.

The term "aryl" is intended to indicate a radical of aromatic carbocyclic rings comprising 6-20 carbon atoms, such as 6-14 carbon atoms, preferably 6-10 carbon atoms, in particular 5- or 6-membered rings, including fused carbocyclic rings with at least one aromatic ring, such as phenyl, naphthyl, indenyl and indanyl.

The term "heteroaryl" is intended to indicate radicals of heterocyclic aromatic rings comprising 1-6 heteroatoms (selected from O, S and N) and 1-20 carbon atoms, such as 1-5 heteroatoms and 1-10 carbon atoms, such as 1-5 heteroatoms and 1-6 carbon atoms, such as 1-5 heteroatoms and 1-3 carbon atoms, in particular 5- or 6-membered rings with 1-4 heteroatoms selected from O, S and N, including fused bicyclic rings with 1-4 heteroatoms, and wherein at least one ring is aromatic, e.g. pyridyl, quinolyl, isoquinolyl, indolyl, thiadiazolyl, oxodiazolyl, tetrazolyl, furanyl, pyridyl, thiazolyl, benzooxazolyl, imidazolyl, pyrazolyl, oxazolyl, isoxazolyl, thienyl, pyrazinyl, isothiazolyl, benzimidazolyl, and benzofuranyl.

In the present context, the term "alkyl" is intended to indicate a radical obtained when one hydrogen atom is removed from a hydrocarbon. Said alkyl comprises 1-20, preferably 1-12, such as 1-6, such as 1-4 or such as 1-3 carbon atoms. The term includes the subclasses normal alkyl (n-alkyl), secondary and tertiary alkyl, such as methyl, ethyl, n-propyl, isopropyl, n-butyl, isobutyl, sec.-butyl, tert.-butyl, pentyl, isopentyl, hexyl and isohexyl.

The term "cycloalkyl" is intended to indicate a saturated cycloalkane radical comprising 3-20 carbon atoms, preferably 3-10 carbon atoms, in particular 3-8 carbon atoms, such as 3-6 carbon atoms, including fused bicyclic rings, e.g. cyclopropyl, cyclobutyl, cyclopentyl, cyclohexyl, or cycloheptyl.

The term "heterocycloalkyl" is intended to indicate a cycloalkane radical as described above, wherein one or more carbon atoms are replaced by heteroatoms, comprising 1-20 carbon atoms, e.g. 2-5 or 2-4 carbon atoms, further comprising 1-6 heteroatoms, preferably 1, 2, or 3 heteroatoms, selected from O, N, or S, e.g. piperidinyl, pyrrolidinyl, morpholinyl, [1,3]dioxolanyl and [1,3]dioxolyl, or including fused bicyclic rings with 1-4 heteroatoms, wherein at least one ring comprises a heteroatom, and wherein the other ring may for example be a carbocyclic ring, e.g. isoindolyl.

The term "alkenyl" is intended to indicate a mono-, di-, tri-, tetra- or pentaunsaturated hydrocarbon radical comprising 2-10 carbon atoms, in particular 2-6 carbon atoms, such as 2-4 carbon atoms, e.g. ethenyl, propenyl (allyl), methylbutenyl, butenyl, pentenyl or hexenyl.

The term "cycloalkenyl" is intended to indicate mono-, di- tri- or tetraunsaturated non-aromatic cyclic hydrocarbon radicals, comprising 3-20 carbon atoms, including fused bicyclic rings, typically comprising 3-10 carbon atoms, such as 3, 4, or 6 carbon atoms, e.g. cyclopropenyl, cyclobutenyl, cyclopentenyl, cyclohexenyl, cylcoheptenyl.

The term "heterocycloalkenyl" is intended to indicate a cycloalkene radical as described above, wherein one or more carbon atoms are replaced by heteroatoms, comprising 1-20 carbon atoms, e.g. 2-4 carbon atoms, further comprising 1-6 heteroatoms, preferably 1, 2, or 3 heteroatoms, selected from O, N, or S, including fused bicyclic rings with 1-4 heteroatoms, wherein at least one ring comprises a heteroatom and wherein the other ring may for example be a carbocyclic ring, e.g. dihydrofuranyl, or 2,5-dihydro-1H-pyrrolyl.

The term "alkynyl" is intended to indicate an hydrocarbon radical comprising 1-5 triple C—C bonds and 2-20 carbon atoms, typically comprising 2-10 carbon atoms, in particular 2-6 carbon atoms, such as 2-4 carbon atoms, e.g. ethynyl, propynyl, butynyl, pentynyl or hexynyl.

The term "halogen" is intended to indicate a substituent from the $7^{th}$ main group of the periodic table, such as fluoro, chloro and bromo.

The term "haloalkyl" is intended to indicate an alkyl group as defined above substituted with one or more halogen atoms as defined above, e.g. fluoro or chloro, such as difluoromethyl, or trifluoromethyl.

The term "alkoxy" is intended to indicate a radical of the formula —OR', wherein R' is alkyl as indicated above, e.g. methoxy, ethoxy, n-propoxy, isopropoxy, butoxy, etc.

The term "hydroxyalkyl" is intended to indicate an alkyl group as defined above substituted with one or more hydroxy, e.g. hydroxymethyl, hydroxyethyl, hydroxypropyl.

The term "amino" is intended to indicate a radical of the formula —NR"$_2$, wherein each R" independently represents hydrogen, or a hydrocarbon radical as indicated above, e.g. —NH$_2$, dimethylamino, —NHMe, —NHEt, tert.-butylamino.

The term "alkylthio" is intended to indicate a radical of the formula —S—R', wherein R' is alkyl as indicated above, e.g. —SMe.

The term "alkoxycarbonyl" is intended to indicate a radical of the formula —C(O)—O—R', wherein R' is alkyl as indicated above, e.g. methoxycarbonyl, ethoxycarbonyl, n-propoxycarbonyl, isopropoxycarbonyl, tert-butoxycarbonyl etc.

The term "aminocarbonyl" is intended to indicate a radical of the formula —C(O)—NR"$_2$, wherein each R" is as indicated above.

The term "alkylcarbonylamino" is intended to indicate a radical of the formula —NR"-C(O)—R', wherein R' is alkyl as indicated above, and each R" is as indicated above.

The term "alkylcarbonyl" is intended to indicate a radical of the formula —C(O)—R', wherein R' is alkyl as indicated above, e.g. acetyl.

The term "alkylcarbonyloxy" is intended to indicate a radical of the formula —O—C(O)—R', wherein R' is alkyl as indicated above.

The term "alkoxycarbonyloxy" is intended to indicate a radical of the formula —O—C(O)—O—R', wherein R' is alkyl as indicated above.

The term "heterocyclic ring" is intended to include the definitions heteroaryl, heterocycloalkyl and heterocycloalkenyl as defined above, including annelated ring systems with each other or with cyclic hydrocarbons, e.g. 2,5-dihydrobenzo(b)dioxocine, 2,3,5,8-tetrahydro-[1,4]dioxocine, 5,8-dihydro-[1,4]dioxocine, 2,3-dihydro-1H-isoindole.

The term "alkylaryl" is intended to indicate an aryl radical as defined above, which is substituted with an alkyl radical as defined above, e.g. tolyl (=toloyl), ethylbenzene, etc.

The term "arylalkyl" is intended to indicate an alkyl radical as defined above, which is substituted with an aryl radical as defined above, e.g. benzyl, phenylethyl, naphthyl methyl, etc.

The term "alkoxyalkyl" is intended to indicate an alkyl radical as defined above, which is substituted with an alkoxy radical as defined above, i.e. —R'—O—R', wherein each R' is alkyl, same or different, as indicated above, e.g. methoxymethyl, ethoxymethyl.

The term "aryloxy" is intended to indicate —O—R'", wherein R'" is aryl as indicated above, e.g. phenoxy.

The term "arylcarbonyl" is intended to indicate —C(O)—R'''', wherein R'''' is an aryl radical as defined above, e.g. benzoyl, naphthylcarbonyl.

The term "alkylalkoxycarbonyl" is intended to indicate —R'—C(O)—O—R', wherein each R' is alkyl, same or different, as indicated above, e.g. tert-butoxycarbonylmethyl, methoxycarbonylmethyl.

The term "pharmaceutically acceptable salt" is intended to indicate salts prepared by reacting a compound of formula I with a suitable inorganic or organic acid, such as hydrochloric, hydrobromic, hydroiodic, sulfuric, nitric, phosphoric, formic, acetic, 2,2-dichloroaetic, adipic, ascorbic, L-aspartic, L-glutamic, galactaric, lactic, maleic, L-malic, phthalic, citric, propionic, benzoic, glutaric, gluconic, D-glucuronic, methanesulfonic, salicylic, succinic, malonic, tartaric, benzenesulfonic, ethane-1,2-disulfonic, 2-hydroxy ethanesulfonic acid, toluenesulfonic, sulfamic or fumaric acid. Pharmaceutically acceptable salts of compounds of formula I may also be prepared by reaction with a suitable base such as sodium hydroxide, potassium hydroxide, magnesium hydroxide, calcium hydroxide, silver hydroxide, ammonia or the like, or suitable non-toxic amines, such as lower alkylamines, for example triethylamine, hydroxy-lower alkylamines, for example 2-hydroxyethylamine, bis-(2-hydroxyethyl)-amine, cycloalkylamines, for example dicyclohexylamine, or benzylamines, for example N,N'-dibenzylethylenediamine, and dibenzylamine, or L-arginine or L-lysine. Salts obtained by reaction with a suitable base include, but are not limited to sodium salts, choline salts, 2-(dimethylamino)-ethanol salts, 4-(2-hydroxyethyl)-morpholin salts, L-lysine salts, N-(2-hydroxyethyl)-pyrrolidine salts, ethanolamine salts, potassium salts, tetrabutylammonium salts, benzyltrimethylammonium salts, cetyltrimethylammonium salts, tetramethylammonium salts, tetrapropylammonium salts, tris(hydroxymethyl)aminomethane salts, N-methyl-D-glucamine salts, silver salts, benzethonium salts, and triethanolamine salts.

The term "solvate" is intended to indicate a species formed by interaction between a compound, e.g. a compound of formula I, and a solvent, e.g. alcohol, glycerol or water, wherein said species are in a solid form. When water is the solvent, said species is referred to as a hydrate.

Compounds of the invention which comprise free hydroxyl groups or free carboxylic acid groups may also exist in the form of pharmaceutically acceptable, physiologically cleavable esters, and as such are included within the scope of the present invention. Such pharmaceutically acceptable esters are preferably prodrug ester derivatives, such being convertible by solvolysis or cleavage under physiologically conditions to the corresponding compounds of the invention which comprise free hydroxyl groups or free carboxylic acid groups respectively, e.g. In-vivo hydrolysable.

EMBODIMENTS OF THE PRESENT INVENTION

In one or more embodiments of the present invention ring B represents pyridyl, pyrazinyl, quinolyl, pyrimidinyl or pyridazinyl optionally substituted with one or more same or different substituents selected from fluoro, chloro, bromo, cyano, methoxy, —$NH_2$ or $C_{1-4}$amino.

In one or more embodiments of the present invention ring B, optionally substituted with $R_{11}$, represents 2-(6-chloro-pyrazinyl), 2-pyrazinyl, 4-(3-bromo-pyridyl), 4-(3,5-dibromo-pyridyl), 4-(6-chloro-pyrimidinyl), 2-(4-chloro-pyridyl), 3-(2-chloro-pyridyl), 4-(2-methoxy-pyridyl), 4-(2-cyano-pyridyl), 3-pyridazinyl, 4-(2-tert-butylamino-3,5-dichloro-pyridyl), 4-(2-amino-3,5-dichloro-pyridyl), 4-(3,5-dichloro-pyridyl), 2-(3-bromo-pyrazinyl), 4-pyridyl, 4-quinolyl or 4-(3,5-dichloro-1-oxy-pyridyl).

In one or more embodiments of the present invention formula I represents general formula Iz,

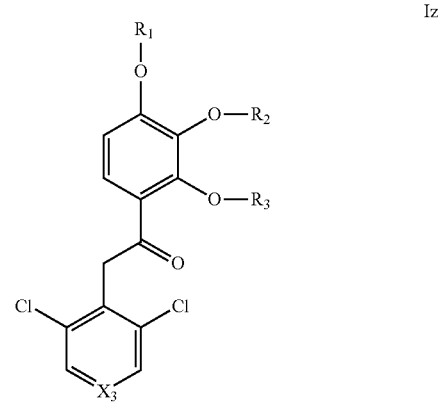

wherein $X_3$ represents —CH— or N, and wherein $R_1$, $R_2$, and $R_3$ are as anywhere defined herein.

In one or more preferred embodiments of the present invention $R_1$ represents alkyl, alkenyl, alkynyl, haloalkyl, hydroxyalkyl, or alkylcarbonyl, all of which are optionally substituted by one or more, same or different substituents selected from $R_4$, and/or
$R_2$ represents alkyl, cycloalkyl, alkenyl, cycloalkenyl, alkynyl, haloalkyl, hydroxyalkyl, heterocycloalkenyl, alkylaryl, alkylalkoxycarbonyl, arylalkyl, alkylcarbonyloxy, or alkoxyalkyl, all of which are optionally substituted by one or more, same or different substituents selected from $R_5$; or $R_2$ represents —$CH_2$—C(O)$NR_9$—$R_{12}$.

In one or more preferred embodiments of the present invention $R_1$ represents methyl or ethyl.

In one or more embodiments of the present invention $R_2$ represents $C_1$-$C_6$alkyl, $C_1$-$C_6$alkenyl, $C_1$-$C_6$alkoxy $C_1$-$C_6$alkyl, hydroxy$C_1$-$C_6$alkyl, halo$C_1$-$C_8$alkyl, $C_1$-$C_6$alkynyl, $C_1$-$C_6$cycloalkyl, $C_1$-$C_6$alkyl$C_6$-$C_{10}$aryl, $C_1$-$C_6$alkyl$C_{1-6}$alkoxycarbonyl or $C_1$-$C_6$alkylcarbonyloxy, all of which are optionally substituted by one or more, same or different substituents selected from $R_5$.

In one or more embodiments of the present invention $R_2$ represents methyl, ethyl, propyl, tert-butoxycarbonylmethyl, allyl, difluoromethyl, ethylbenzene, methylbenzene, butenyl, hydroxyethyl, ethylphenyl, tolyl, pentenyl, methoxyethyl, butinyl, propinyl, cyclopentyl, all of which are optionally substituted by one or more, same or different substituents selected from $R_5$.

In one or more embodiments of the present invention $R_2$ represents cyclopropyl, methylcyclopropyl, cyclopentyl, methyl, ethyl, propyl, or allyl, all of which are optionally substituted by one or more, same or different substituents selected from hydroxy, fluoro, or alkoxy.

In one or more embodiments of the present invention $R_3$ represents methyl, ethyl, propyl, butyl, pentyl, hydroxyethyl, hexyl, butenyl, pentenyl, allyl, butinyl, methylbenzene, ethylbenzene, tolyl, toluoyl, propylbenzene, methylnaphthyl, ethylnaphthyl, methylcarbonylmethoxy, methylcarbonylethoxy, methoxyethyl, methoxypropyl, all of which are optionally substituted by one or more, same or different substituents selected from $R_6$, all of which are optionally substituted by one or more, same or different substituents selected from $R_8$, or $R_3$ represents hydrogen, —$CH_2$—C(O)-heterocycloalkyl or —$CH_2$—C(O)$NR_9$—$R_{12}$.

In one or more embodiments of the present invention $R_3$ represents methyl, ethyl, propyl, or allyl, all of which are optionally substituted by one or more, same or different substituents selected from hydroxy, fluoro, or alkoxy.

In one or more embodiments of the present invention $R_5$ represents methyl, tert-butoxy, ethenyl, cyclopropyl, propenyl, phenyl, butenyl, propinyl, ethylhydroxy, ethinyl, allyl, ethyl, or methoxy,
all of which are optionally substituted by one or more, same or different substituents selected from $R_7$, or $R_5$ represents hydrogen, oxo, chloro, fluoro, or hydroxy.

In one or more embodiments of the present invention $R_6$ represents ethenyl, methyl, tert-butoxy, isoxazolyl, methoxy, propinyl, butenyl, phenyl, pyridyl, benzoxazolyl, thiazolyl, [1,3,4]thiadiazolyl, [1,2,4]oxadiazolyl, 2,3-dihydro-1H-isoindolyl, ethoxy, thiophenyl, propyl, ethyl, butyl, pentyl, allyl, isopropoxy, isopropyl, naphthyl, cyclohexyl, hydroxy, cyclopentyl, phenoxy, tolyl, toluoyl, benzoyl, carbonylnaphthalene, ethylbenzene, quinolinyl, —$NH_2$, ethoxycarbonyl, methoxycarbonyl, carbamoyl, isoindole, methylamine, pyrrolidyl, morpholinyl, methylsulfonyl, methylsulfinyl, butylamine, propylamine, ethylamine, cycloheptyl, hydroxyethyl, hydroxypropyl, indanyl, or ethoxyethyl, all of which are optionally substituted by one or more, same or different substituents selected from $R_8$, or $R_6$ represents hydrogen, oxo, fluoro, chloro, or cyano.

In one or more embodiments of the present invention $R_8$ represents, methyl, ethyl, propyl, butyl, phenyl, cyclopropyl, ethoxy, methoxy, allyl, ethenyl, ethoxycarbonyl, hydroxy, naphthyl, cyclohexyl, methoxycarbonyl, phenxoxy, isopropoxy, —$NH_2$, methylamine, pyrrolidinyl, morpholinyl, methylsulfonyl, methylsulfinyl, cycloheptyl, cyclopentyl, hydroxymethyl, hydroxyethyl, dimethylamino, furanyl, pyridyl, tolyl, piperidinyl, acetyl, thiophenyl, cycloheptyl, all of which are optionally substituted by one or more, same or different substituents selected from $R_{10}$, or $R_8$ represents hydrogen, oxo, chloro, bromo, fluoro, cyano, or trifluoromethyl.

In one or more embodiments of the present invention $R_9$ represents hydrogen, methyl, or ethyl.

In one or more embodiments of the present invention $R_{10}$ represents hydrogen, oxo, methyl, hydroxy, fluoro, cyano, chloro, or methoxy.

In one or more embodiments of the present invention $R_2$ represents methyl.

In one or more embodiments of the present invention $R_1$ and $R_2$ both represent methyl.

In one or more embodiments of the present invention $R_1$ and $R_3$ represent methyl and/or difluoromethyl.

In one or more embodiments of the present invention $R_3$ represents —$CH_2$—C(O)NH—$R_{12}$, —$CH_2$—C(O)NH-heterocycloalkyl, —$CH_2CH_2$-phenyl-$R_6$, or —$CH_2$-phenyl-$R_6$.

In one or more embodiments of the present invention $R_2$ and/or $R_3$ represents —$CH_2COOH$, methyl, hydrogen, allyl, ethyl, tert-butoxycarbonylmethyl, difluoromethyl, 3-methyl-5-methylisoxazole, 2-methoxy-ethane, 2-butyne, 2-methyl-2-butene, 2-phenylethane, benzyl, 2-methyl-1,3-benzoxazole, 4-methyl-2-methylthiazole, 2-methyl-5-cyclopropyl-[1,3,4]thiadiazole, 3-methyl-[1,2,4]oxadiazole, ethyl acetate, 4-chlorobenzyl, 5-chloro-2-methyl-thiophene, phenoxyethane, (4-methylphenyl)ethane, 3-phenylpropane, (3-methoxyphenyl)ethane, (4-methoxyphenyl)ethane, (3-bromophenyl)ethane, (2-methoxyphenyl)ethane, (4-fluorophenyl) ethane, (2-fluorophenyl)ethane, (3,4-dimethoxyphenyl) ethane, benzyl acetate, isopropyl acetate, 3-methyl benzoic acid methyl ester, 3-methyl-butane, 1-hexyl, but-1-ene, pent-1-ene, 1-propyl, 1-butyl, 2-methyl-propane, butyric acid ethyl ester, 4-methyl-benzyl, 3-chloro-benzyl, propoxybenzene, 1-(4-methoxy-phenyl)-ethanone, 4-methyl-benzonitrile, 2-methyl-naphthalene, 1-pentyl, methyl-cyclohexane, 3-methyl-benzonitrile, 1-ethoxy-4-chloro-benzene, 2-ethylbutane, 2-hydroxy-ethane, 4-methyl benzoic acid methyl ester, 1-naphthalen-2-yl-ethanone, 2,5-dimethoxy-phenylethanone, 1-p-tolyl-ethanone, 4-fluoro-benzyl, 2-fluoro-benzyl, 5-trifluoromethyl-benzyl, 5-trifluoromethoxy-benzyl, 3-fluoro-5-trifluoromethyl-benzyl, 1-(2-methoxy-phenyl)-ethanone, 1-(2,4-dimethyl-phenyl)-ethanone, 4-chloro-benzyl, 2-difluoromethoxy-benzyl, 4-isopropyl-benzyl, 2-fluoro-6-trifluoromethyl-benzyl, 2,3-difluoro-4-methyl-benzyl, 2-methyl-benzyl, 3-methyl-benzyl, pent-2-ene, 6-methyl-2-methyl-quinoline, 2-chloro-benzyl, 3-methoxy-benzyl, 4-methoxy-benzyl, (3-Chloro-phenyl)-ethane, 5-methyl-hexane, ethyl-cyclohexane, pentanoic acid ethyl ester, (propoxymethyl)-benzene, acetamide, 2-ethyl-isoindole-1,3-dione, 2-propyl-isoindole-1,3-dione, N-methyl-acetamide, methyl-cyclopropane, but-1-ene, 4-yl-but-1-ene, 2-methyl-pent-2-ene, ethanol, benzyl, pent-2-ene, 2-methoxy-ethane, but-2-yne, propyne, acetate, 1-pyrrolidin-1-yl-ethanone, N-benzylacetamide, 1-morpholin-4-yl-ethanone, N-phenyl-acetamide, N-methyl-N-phenyl-acetamide, N-(3-hydroxy-3-methyl-butyl)-acetamide, N-n-propyl-acetamide, N-ethyl-acetamide, N-isopropyl-acetamide, N-butyl-acetamide, N-cyclopentyl-acetamide, N-(3-methyl-butyl)-acetamide, N-(4-methoxy-benzyl)-acetamide, N-(2,2-dimethyl-propyl)-acetamide, N-cyclohexyl-acetamide, N-(3-methoxy-benzyl)-acetamide, N-cycloheptyl-acetamide, N-(2-methoxy-benzyl)-acetamide, N-cyclohexylmethyl-acetamide, N-(2-hydroxy-ethyl)-acetamide, N-(1-phenyl-ethyl)-acetamide, N-(3-hydroxy-propyl)-acetamide, N-(2-methoxy-ethyl)-acetamide, N-(2-dimethylamino-ethyl)-acetamide, N-(3-dimethylamino-propyl)-acetamide, N-(1-phenyl-ethyl)-acetamide, N-(3-isopropoxy-propyl)-acetamide, N-furan-2-ylmethyl-acetamide, N-pyridin-2-ylmethyl-acetamide, N-pyridin-3-ylmethyl-acetamide, N-(2-phenoxy-ethyl)-acetamide, N-pyridin-4-ylmethyl-acetamide, N-(4-ethyl-benzyl)-acetamide, N-(3,5-difluoro-benzyl)-acetamide, N-(2,3-difluoro-benzyl)-acetamide, N-(2-pyridin-2-yl-ethyl)-acetamide, N-(2-methyl-benzyl)-acetamide, N-(3-fluoro-benzyl)-acetamide, N-(3-methyl-benzyl)-acetamide, N-(4-methyl-benzyl)-acetamide, N-phenethyl-acetamide, N-(2-pyridin-4-yl-ethyl)-acetamide, N-(3-phenyl-propyl)-acetamide, N-(2-chloro-benzyl)-acetamide, N-(2-piperidin-1-yl-ethyl)-acetamide, N-(3-chloro-benzyl)-acetamide, N-(2-morpholin-4-yl-ethyl)-acetamide, N-(4-chloro-benzyl)-acetamide, N-(2-pyridin-3-yl-ethyl)-acetamide, N-(2-pyrrolidin-1-yl-ethyl)-acetamide, N-(2-acetylamino-ethyl)-acetamide, (R)—N-(2-hydroxy-2-phenyl-ethyl)-acetamide, (S)—N-(2-hydroxy-2-phenyl-ethyl)-acetamide, N-thiophen-2-ylmethyl-acetamide, N-[3-(2-oxo-pyrrolidin-1-yl)-propyl]-acetamide, N-(2-hydroxy-indan-1-yl)-acetamide, N-cycloheptylmethyl-acetamide, N-[2-(2-hydroxy-ethoxy)-ethyl]-acetamide, N-(4-dimethylamino-butyl)-acetamide, cyclopentan, cyclopropylmethyl, ethyl, phenyl-ethane, acetic acid benzyl ester, 2-methyl-benzonitrile, (1-oxy-pyridin-4-yl)ethane, (4-pyridyl)ethane, (3-pyridyl)ethane, (2-pyridyl) ethane, (4-benzonitrile)ethane, (4-methylsulfinyl-phenyl) ethane, (4-methylsulfonyl-phenyl)ethane, 1-phenyl-propane, 2-phenyl-propane or 1-methyl-2-phenyl-ethane.

In one or more embodiments of the present invention $R_{12}$ represents alkyl, cycloalkyl, hxydroxyalkyl, aryl, arylalkyl, alkylcarbonylamino, all of which are optionally substituted with one or more same or different substituents selected from alkyl, cycloalkyl, alkoxy, heterocycloalkyl, heteroaryl, aryloxy, amino, hydroxy, halogen, oxy, all of which are optionally substituted with oxo or hydroxyl, or $R_{12}$ represents hydrogen;

In one or more embodiments of the present invention, $R_{12}$ represents methyl, ethyl, 1-propyl, or 2-propyl, optionally substituted with one or more, same of different substituents selected from fluoro, chloro, bromo, or methyl; or $R_{12}$ represents hydrogen.

In yet another embodiment, the present invention relates to a compound of general formula Iz, wherein $X_3$ represents CH, $R_1$ and $R_2$ are both methyl, and $R_3$ is as anywhere described herein.

In one or more embodiments of the present invention, $R_1$ and $R_2$ cannot both be hydrogen.

In one or more embodiments of the present invention, $R_2$ and/or $R_3$ are as described anywhere in the following exemplified compounds.

The present invention includes all embodiments wherein $R_1$, $R_2$, $R_3$, $R_4$, $R_5$, $R_6$, $R_7$, $R_8$, $R_9$, $R_{10}$, $R_{11}$ and $R_{12}$ are combined in any combination as anywhere described herein.

In one or more embodiments of the present invention, the compounds of general structure I have a molecular weight below 800 Dalton, such as below 750 Dalton, e.g. below 700 Dalton, or below 650, 600, 550, or 500 Dalton.

In particular compounds of formula I may be selected from
2-(3,5-Dichloro-pyridin-4-yl)-1-(2-hydroxy-3,4-dimethoxy-phenyl)-ethanone (compound 101),
2-(3,5-Dichloro-pyridin-4-yl)-1-(3-hydroxy-2,4-dimethoxy-phenyl)-ethanone (compound 102),
1-(2-Allyloxy-3-hydroxy-4-methoxy-phenyl)-2-(3,5-dichloro-pyridin-4-yl)-ethanone (compound 103),
2-(3,5-Dichloro-pyridin-4-yl)-1-(2,3-diethoxy-4-methoxy-phenyl)-ethanone (compound 104),
{2-tert-Butoxycarbonylmethoxy-6-[2-(3,5-dichloro-pyridin-4-yl)-acetyl]-3-methoxy-phenoxy}-acetic acid tert-butyl ester (compound 105),
1-(2,3-Bis-allyloxy-4-methoxy-phenyl)-2-(3,5-dichloro-pyridin-4-yl)-ethanone (compound 106),
1-(2,3-Bis-difluoromethoxy-4-methoxy-phenyl)-2-(3,5-dichloro-pyridin-4-yl)-ethanone (compound 107),
2-(3,5-Dichloro-pyridin-4-yl)-1-[3,4-dimethoxy-2-(5-methyl-isoxazol-3-ylmethoxy)-phenyl]-ethanone (compound 108),
2-(3,5-Dichloro-pyridin-4-yl)-1-[3,4-dimethoxy-2-(2-methoxy-ethoxy)-phenyl]-ethanone (compound 109),
1-(2-But-2-ynyloxy-3,4-dimethoxy-phenyl)-2-(3,5-dichloro-pyridin-4-yl)-ethanone (compound 110),
2-(3,5-Dichloro-pyridin-4-yl)-1-[3,4-dimethoxy-2-(3-methyl-but-2-enyloxy)-phenyl]-ethanone (compound III),
2-(3,5-Dichloro-pyridin-4-yl)-1-(3,4-dimethoxy-2-phenethyloxy-phenyl)-ethanone (compound 112),
1-(2-Benzyloxy-3,4-dimethoxy-phenyl)-2-(3,5-dichloro-pyridin-4-yl)-ethanone (compound 113),
1-(2-Allyloxy-3,4-dimethoxy-phenyl)-2-(3,5-dichloro-pyridin-4-yl)-ethanone (compound 114),
1-[2-(Benzooxazol-2-ylmethoxy)-3,4-dimethoxy-phenyl]-2-(3,5-dichloro-pyridin-4-yl)-ethanone (compound 115),
2-(3,5-Dichloro-pyridin-4-yl)-1-[3,4-dimethoxy-2-(2-methyl-thiazol-4-ylmethoxy)-phenyl]-ethanone (compound 116),
1-[2-(5-Cyclopropyl-[1,3,4]thiadiazol-2-ylmethoxy)-3,4-dimethoxy-phenyl]-2-(3,5-dichloro-pyridin-4-yl)-ethanone (compound 117),
2-(3,5-Dichloro-pyridin-4-yl)-1-[3,4-dimethoxy-2-([1,2,4] oxadiazol-3-ylmethoxy)-phenyl]-ethanone (compound 118),
{6-[2-(3,5-Dichloro-pyridin-4-yl)-acetyl]-2,3-dimethoxy-phenoxy}-acetic acid ethyl ester (compound 119),
1-{2-[2-(4-Chloro-phenyl)-ethoxy]-3,4-dimethoxy-phenyl}-2-(3,5-dichloro-pyridin-4-yl)-ethanone (compound 120),
1-[2-(5-Chloro-thiophen-2-ylmethoxy)-3,4-dimethoxy-phenyl]-2-(3,5-dichloro-pyridin-4-yl)-ethanone (compound 121),
2-(3,5-Dichloro-pyridin-4-yl)-1-[3,4-dimethoxy-2-(2-phenoxy-ethoxy)-phenyl]-ethanone (compound 122),
2-(3,5-Dichloro-pyridin-4-yl)-1-[3,4-dimethoxy-2-(2-p-tolyl-ethoxy)-phenyl]-ethanone (compound 123),
2-(3,5-Dichloro-pyridin-4-yl)-1-[3,4-dimethoxy-2-(3-phenyl-propoxy)-phenyl]-ethanone (compound 124),
2-(3,5-Dichloro-pyridin-4-yl)-1-{3,4-dimethoxy-2-[2-(3-methoxy-phenyl)-ethoxy]-phenyl}-ethanone (compound 125),
2-(3,5-Dichloro-pyridin-4-yl)-1-{3,4-dimethoxy-2-[2-(4-methoxy-phenyl)-ethoxy]-phenyl}-ethanone (compound 126),
1-{2-[2-(3-Bromo-phenyl)-ethoxy]-3,4-dimethoxy-phenyl}-2-(3,5-dichloro-pyridin-4-yl)-ethanone (compound 127),
2-(3,5-Dichloro-pyridin-4-yl)-1-{3,4-dimethoxy-2-[2-(2-methoxy-phenyl)-ethoxy]-phenyl}-ethanone (compound 128),
2-(3,5-Dichloro-pyridin-4-yl)-1-{2-[2-(4-fluoro-phenyl)-ethoxy]-3,4-dimethoxy-phenyl}-ethanone (compound 129),
2-(3,5-Dichloro-pyridin-4-yl)-1-{2-[2-(2-fluoro-phenyl)-ethoxy]-3,4-dimethoxy-phenyl}-ethanone (compound 130),
2-(3,5-Dichloro-pyridin-4-yl)-1-{2-[2-(3,4-dimethoxy-phenyl)-ethoxy]-3,4-dimethoxy-phenyl}-ethanone (compound 131),
{6-[2-(3,5-Dichloro-pyridin-4-yl)-acetyl]-2,3-dimethoxy-phenoxy}-acetic acid benzyl ester (compound 132),
{6-[2-(3,5-Dichloro-pyridin-4-yl)-acetyl]-2,3-dimethoxy-phenoxy}-acetic acid isopropyl ester (compound 133),
3-{6-[2-(3,5-Dichloro-pyridin-4-yl)-acetyl]-2,3-dimethoxy-phenoxymethyl}-benzoic acid methyl ester (compound 134),
2-(3,5-Dichloro-pyridin-4-yl)-1-[3,4-dimethoxy-2-(3-methyl-butoxy)-phenyl]-ethanone (compound 135),
2-(3,5-Dichloro-pyridin-4-yl)-1-(2-hexyloxy-3,4-dimethoxy-phenyl)-ethanone (compound 136),
1-(2-But-3-enyloxy-3,4-di methoxy-phenyl)-2-(3,5-dichloro-pyridin-4-yl)-ethanone (compound 137),
2-(3,5-Dichloro-pyridin-4-yl)-1-(3,4-dimethoxy-2-pent-4-enyloxy-phenyl)-ethanone (compound 138),
2-(3,5-Dichloro-pyridin-4-yl)-1-(3,4-dimethoxy-2-propoxy-phenyl)-ethanone (compound 139),
1-(2-Butoxy-3,4-dimethoxy-phenyl)-2-(3,5-dichloro-pyridin-4-yl)-ethanone ethanone (compound 140),
2-(3,5-Dichloro-pyridin-4-yl)-1-(2-isobutoxy-3,4-dimethoxy-phenyl)-ethanone (compound 141),
4-{6-[2-(3,5-Dichloro-pyridin-4-yl)-acetyl]-2,3-dimethoxy-phenoxy}-butyric acid ethyl ester (compound 142),
2-(3,5-Dichloro-pyridin-4-yl)-1-[3,4-dimethoxy-2-(4-methyl-benzyloxy)-phenyl]-ethanone (compound 143),
1-[2-(3-Chloro-benzyloxy)-3,4-dimethoxy-phenyl]-2-(3,5-dichloro-pyridin-4-yl)-ethanone (compound 144),
2-(3,5-Dichloro-pyridin-4-yl)-1-[3,4-dimethoxy-2-(3-phenoxy-propoxy)-phenyl]-ethanone (compound 145),
2-(3,5-Dichloro-pyridin-4-yl)-1-{3,4-dimethoxy-2-[2-(4-methoxy-phenyl)-2-oxo-ethoxy]-phenyl}-ethanone (compound 146), 2-{6-[2-(3,5-Dichloro-pyridin-4-yl)-acetyl]-2,3-dimethoxy-phenoxymethyl}-benzonitrile (compound 147),
4-{6-[2-(3,5-Dichloro-pyridin-4-yl)-acetyl]-2,3-dimethoxy-phenoxymethyl}-benzonitrile (compound 148),
2-(3,5-Dichloro-pyridin-4-yl)-1-[3,4-dimethoxy-2-(naphthalen-2-ylmethoxy)-phenyl]-ethanone (compound 149),
2-(3,5-Dichloro-pyridin-4-yl)-1-(3,4-dimethoxy-2-pentyloxy-phenyl)-ethanone (compound 150),
1-(2-Cyclohexylmethoxy-3,4-dimethoxy-phenyl)-2-(3,5-dichloro-pyridin-4-yl)-ethanone (compound 151),
3-{6-[2-(3,5-Dichloro-pyridin-4-yl)-acetyl]-2,3-dimethoxy-phenoxymethyl}-benzonitrile (compound 152),
1-{2-[2-(4-Chloro-phenoxy)-ethoxy]-3,4-dimethoxy-phenyl}-2-(3,5-dichloro-pyridin-4-yl)-ethanone (compound 153),
2-(3,5-Dichloro-pyridin-4-yl)-1-[2-(2-ethyl-butoxy)-3,4-dimethoxy-phenyl]-ethanone (compound 154),
2-(3,5-Dichloro-pyridin-4-yl)-1-[2-(2-hydroxy-ethoxy)-3,4-dimethoxy-phenyl]-ethanone (compound 155),
4-{6-[2-(3,5-Dichloro-pyridin-4-yl)-acetyl]-2,3-dimethoxy-phenoxymethyl}-benzoic acid methyl ester (compound 156),
2-(3,5-Dichloro-pyridin-4-yl)-1-[3,4-dimethoxy-2-(2-naphthalen-2-yl-2-oxo-ethoxy)-phenyl]-ethanone (compound 157),
2-(3,5-Dichloro-pyridin-4-yl)-1-{2-[2-(2,5-dimethoxy-phenyl)-2-oxo-ethoxy]-3,4-dimethoxy-phenyl}-ethanone (compound 158),
2-(3,5-Dichloro-pyridin-4-yl)-1-[3,4-dimethoxy-2-(2-oxo-2-p-tolyl-ethoxy)-phenyl]-ethanone (compound 159),
2-(3,5-Dichloro-pyridin-4-yl)-1-[2-(4-fluoro-benzyloxy)-3,4-dimethoxy-phenyl]-ethanone (compound 160),
2-(3,5-Dichloro-pyridin-4-yl)-1-[2-(2-fluoro-benzyloxy)-3,4-dimethoxy-phenyl]-ethanone (compound 161),
2-(3,5-Dichloro-pyridin-4-yl)-1-[3,4-dimethoxy-2-(3-trifluoromethyl-benzyloxy)-phenyl]-ethanone (compound 162),
2-(3,5-Dichloro-pyridin-4-yl)-1-[3,4-dimethoxy-2-(3-trifluoromethoxy-benzyloxy)-phenyl]-ethanone (compound 163),
2-(3,5-Dichloro-pyridin-4-yl)-1-[2-(3-fluoro-5-trifluoromethyl-benzyloxy)-3,4-dimethoxy-phenyl]-ethanone (compound 164),
2-(3,5-Dichloro-pyridin-4-yl)-1-{3,4-dimethoxy-2-[2-(2-methoxy-phenyl)-2-oxo-ethoxy]-phenyl}-ethanone (compound 165),
2-(3,5-Dichloro-pyridin-4-yl)-1-{2-[2-(2,4-dimethyl-phenyl)-2-oxo-ethoxy]-3,4-dimethoxy-phenyl}-ethanone (compound 166),
1-[2-(4-Chloro-benzyloxy)-3,4-dimethoxy-phenyl]-2-(3,5-dichloro-pyridin-4-yl)-ethanone (compound 167),
2-(3,5-Dichloro-pyridin-4-yl)-1-[2-(2-difluoromethoxy-benzyloxy)-3,4-dimethoxy-phenyl]-ethanone (compound 168),
2-(3,5-Dichloro-pyridin-4-yl)-1-[2-(4-isopropyl-benzyloxy)-3,4-dimethoxy-phenyl]-ethanone (compound 169),
2-(3,5-Dichloro-pyridin-4-yl)-1-[2-(2-fluoro-6-trifluoromethyl-benzyloxy)-3,4-dimethoxy-phenyl]-ethanone (compound 170),
2-(3,5-Dichloro-pyridin-4-yl)-1-[2-(2,3-difluoro-4-methyl-benzyloxy)-3,4-dimethoxy-phenyl]-ethanone (compound 171),
2-(3,5-Dichloro-pyridin-4-yl)-1-[3,4-dimethoxy-2-(2-methyl-benzyloxy)-phenyl]-ethanone (compound 172),
2-(3,5-Dichloro-pyridin-4-yl)-1-[3,4-dimethoxy-2-(3-methyl-benzyloxy)-phenyl]-ethanone (compound 173),
2-(3,5-Dichloro-pyridin-4-yl)-1-(3,4-dimethoxy-2-pent-2-enyloxy-phenyl)-ethanone (compound 174),
2-(3,5-Dichloro-pyridin-4-yl)-1-[3,4-dimethoxy-2-(2-methyl-quinolin-6-ylmethoxy)-phenyl]-ethanone (compound 175),
1-[2-(2-Chloro-benzyloxy)-3,4-dimethoxy-phenyl]-2-(3,5-dichloro-pyridin-4-yl)-ethanone (compound 176),
2-(3,5-Dichloro-pyridin-4-yl)-1-[3,4-dimethoxy-2-(3-methoxy-benzyloxy)-phenyl]-ethanone (compound 177),
2-(3,5-Dichloro-pyridin-4-yl)-1-[3,4-dimethoxy-2-(4-methoxy-benzyloxy)-phenyl]-ethanone (compound 178),
1-{2-[2-(3-Chloro-phenyl)-ethoxy]-3,4-dimethoxy-phenyl}-2-(3,5-dichloro-pyridin-4-yl)-ethanone (compound 179),
2-(3,5-Dichloro-pyridin-4-yl)-1-[3,4-dimethoxy-2-(5-methyl-hexyloxy)-phenyl]-ethanone (compound 180),
1-[2-(2-Cyclohexyl-ethoxy)-3,4-dimethoxy-phenyl]-2-(3,5-dichloro-pyridin-4-yl)-ethanone (compound 181),
5-{6-[2-(3,5-Dichloro-pyridin-4-yl)-acetyl]-2,3-dimethoxy-phenoxy}-pentanoic acid ethyl ester (compound 182),
1-(2-(3-Benzyloxy-propoxy)-3,4-dimethoxy-phenyl)-2-(3,5-dichloro-pyridin-4-yl)-ethanone (compound 183),
2-{6-[2-(3,5-Dichloro-pyridin-4-yl)-acetyl]-2,3-dimethoxy-phenoxy}-acetamide (compound 184),
2-(2-{6-[2-(3,5-Dichloro-pyridin-4-yl)-acetyl]-2,3-dimethoxy-phenoxy}-ethyl)-isoindole-1,3-dione (compound 185),
2-(3-{6-[2-(3,5-Dichloro-pyridin-4-yl)-acetyl]-2,3-dimethoxy-phenoxy}-propyl)-isoindole-1,3-dione (compound 186),
2-{6-[2-(3,5-Dichloro-pyridin-4-yl)-acetyl]-2,3-dimethoxy-phenoxy}-N-methyl-acetamide (compound 187),
2-(3,5-Dichloro-pyridin-4-yl)-1-(3-ethoxy-2,4-dimethoxy-phenyl)-ethanone (compound 188),
1-(3-Cyclopropylmethoxy-2,4-dimethoxy-phenyl)-2-(3,5-dichloro-pyridin-4-yl)-ethanone (compound 189),
1-(2-Allyloxy-3-but-3-enyloxy-4-methoxy-phenyl)-2-(3,5-dichloro-pyridin-4-yl)-ethanone (compound 190),
1-(3-But-3-enyloxy-2,4-dimethoxy-phenyl)-2-(3,5-dichloro-pyridin-4-yl)-ethanone (compound 191),
2-(3,5-Dichloro-pyridin-4-yl)-1-(2,4-dimethoxy-3-propoxy-phenyl)-ethanone (compound 192),
1-(3-Allyloxy-2,4-dimethoxy-phenyl)-2-(3,5-dichloro-pyridin-4-yl)-ethanone (compound 193),
2-(3,5-Dichloro-pyridin-4-yl)-1-[2,4-dimethoxy-3-(4-methyl-pent-3-enyloxy)-phenyl]-ethanone (compound 194),
2-(3,5-Dichloro-pyridin-4-yl)-1-[3-(2-hydroxy-ethoxy)-2,4-dimethoxy-phenyl]-ethanone (compound 195),
2-(3,5-Dichloro-pyridin-4-yl)-1-(2,4-dimethoxy-3-phenethyloxy-phenyl)-ethanone (compound 196),
1-(3-Benzyloxy-2,4-dimethoxy-phenyl)-2-(3,5-dichloro-pyridin-4-yl)-ethanone (compound 197),
2-(3,5-Dichloro-pyridin-4-yl)-1-(2,4-dimethoxy-3-pent-2-enyloxy-phenyl)-ethanone (compound 198),
2-(3,5-Dichloro-pyridin-4-yl)-1-[2,4-dimethoxy-3-(2-methoxy-ethoxy)-phenyl]-ethanone (compound 199),
1-(3-But-2-ynyloxy-2,4-dimethoxy-phenyl)-2-(3,5-dichloro-pyridin-4-yl)-ethanone (compound 200),
2-(3,5-Dichloro-pyridin-4-yl)-1-(2,4-dimethoxy-3-prop-2-ynyloxy-phenyl)-ethanone (compound 201),
2-(3,5-Dichloro-pyridin-4-yl)-1-[3,4-dimethoxy-2-(2-oxo-2-pyrrolidin-1-yl-ethoxy)-phenyl]-ethanone (compound 202),
N-Benzyl-2-{6-[2-(3,5-dichloro-pyridin-4-yl)-acetyl]-2,3-dimethoxy-phenoxy}-acetamide (compound 203), 2-(3,5-Dichloro-pyridin-4-yl)-1-[3,4-dimethoxy-2-(2-morpholin-4-yl-2-oxo-ethoxy)-phenyl]-ethanone (compound 204),
2-{6-[2-(3,5-Dichloro-pyridin-4-yl)-acetyl]-2,3-dimethoxy-phenoxy}-N-phenyl-acetamide (compound 205),
2-{6-[2-(3,5-Dichloro-pyridin-4-yl)-acetyl]-2,3-dimethoxy-phenoxy}-N-methyl-N-phenyl-acetamide (compound 206),
2-{6-[2-(3,5-Dichloro-pyridin-4-yl)-acetyl]-2,3-dimethoxy-phenoxy}-N-(3-hydroxy-3-methyl-butyl)-acetamide (compound 207),
2-{6-[2-(3,5-Dichloro-pyridin-4-yl)-acetyl]-2,3-dimethoxy-phenoxy}-N-propyl-acetamide (compound 208),
2-{6-[2-(3,5-Dichloro-pyridin-4-yl)-acetyl]-2,3-dimethoxy-phenoxy}-N-Isopropyl-acetamide (compound 209),
N-Butyl-2-{6-[2-(3,5-dichloro-pyridin-4-yl)-acetyl]-2,3-dimethoxy-phenoxy}-acetamide (compound 210),
N-Cyclopentyl-2-{6-[2-(3,5-dichloro-pyridin-4-yl)-acetyl]-2,3-dimethoxy-phenoxy}-acetamide (compound 211),
2-{6-[2-(3,5-Dichloro-pyridin-4-yl)-acetyl]-2,3-dimethoxy-phenoxy}-N-(3-methyl-butyl)-acetamide (compound 212),
2-{6-[2-(3,5-Dichloro-pyridin-4-yl)-acetyl]-2,3-dimethoxy-phenoxy}-N-(4-methoxy-benzyl)-acetamide (compound 213),
2-{6-[2-(3,5-Dichloro-pyridin-4-yl)-acetyl]-2,3-dimethoxy-phenoxy}-N-(2,2-dimethyl-propyl)-acetamide (compound 214),
N-Cyclohexyl-2-{6-[2-(3,5-dichloro-pyridin-4-yl)-acetyl]-2,3-demethoxy-phenoxy}-acetamide (compound 215),
2-{6-[2-(3,5-Dichloro-pyridin-4-yl)-acetyl]-2,3-dimethoxy-phenoxy}-N-(3-methoxy-benzyl)-acetamide (compound 216),
N-Cycloheptyl-2-{6-(2-(3,5-dichloro-pyridin-4-yl)-acetyl)-2,3-dimethoxy-phenoxy}-acetamide (compound 217),
2-{6-[2-(3,5-Dichloro-pyridin-4-yl)-acetyl]-2,3-dimethoxy-phenoxy}-N-(2-methoxy-benzyl)-acetamide (compound 218),
N-Cyclohexylmethyl-2-{6-[2-(3,5-dichloro-pyridin-4-yl)-acetyl]-2,3-dimethoxy-phenoxy}-acetamide (compound 219),
2-{6-[2-(3,5-Dichloro-pyridin-4-yl)-acetyl]-2,3-dimethoxy-phenoxy}-N-(2-hydroxy-ethyl)-acetamide (compound 220),
(R)-2-{6-[2-(3,5-Dichloro-pyridin-4-yl)-acetyl]-2,3-dimethoxy-phenoxy}-N-(1-phenyl-ethyl)-acetamide (compound 221),
2-{6-[2-(3,5-Dichloro-pyridin-4-yl)-acetyl]-2,3-dimethoxy-phenoxy}-N-(3-hydroxy-propyl)-acetamide (compound 222),
2-{6-[2-(3,5-Dichloro-pyridin-4-yl)-acetyl]-2,3-dimethoxy-phenoxy}-N-(2-methoxy-ethyl)-acetamide (compound 223),
2-{6-[2-(3,5-Dichloro-pyridin-4-yl)-acetyl]-2,3-dimethoxy-phenoxy}-N-(2-dimethylamino-ethyl)-acetamide (compound 224),
2-{6-[2-(3,5-Dichloro-pyridin-4-yl)-acetyl]-2,3-dimethoxy-phenoxy}-N-(3-dimethylamino-propyl)-acetamide (compound 225),
(S)-2-{6-[2-(3,5-Dichloro-pyridin-4-yl)-acetyl]-2,3-dimethoxy-phenoxy}-N-(1-phenyl-ethyl)-acetamide (compound 226),
2-{6-[2-(3,5-Dichloro-pyridin-4-yl)-acetyl]-2,3-dimethoxy-phenoxy}-N-(3-isopropoxy-propyl)-acetamide (compound 227),
2-{6-[2-(3,5-Dichloro-pyridin-4-yl)-acetyl]-2,3-dimethoxy-phenoxy}-N-furan-2-ylmethyl-acetamide (compound 228),
2-{6-[2-(3,5-Dichloro-pyridin-4-yl)-acetyl]-2,3-dimethoxy-phenoxy}-N-pyridin-2-ylmethyl-acetamide (compound 229),
2-{6-[2-(3,5-Dichloro-pyridin-4-yl)-acetyl]-2,3-dimethoxy-phenoxy}-N-pyridin-3-ylmethyl-acetamide (compound 230),
2-{6-[2-(3,5-Dichloro-pyridin-4-yl)-acetyl]-2,3-dimethoxy-phenoxy}-N-(2-phenoxy-ethyl)-acetamide (compound 231),
2-{6-[2-(3,5-Dichloro-pyridin-4-yl)-acetyl]-2,3-dimethoxy-phenoxy}-N-pyridin-4-ylmethyl-acetamide (compound 232),
2-{6-[2-(3,5-Dichloro-pyridin-4-yl)-acetyl]-2,3-dimethoxy-phenoxy}-N-(4-ethyl-benzyl)-acetamide (compound 233),
2-{6-[2-(3,5-Dichloro-pyridin-4-yl)-acetyl]-2,3-dimethoxy-phenoxy}-N-(3,5-difluoro-benzyl)-acetamide (compound 234),
2-{6-[2-(3,5-Dichloro-pyridin-4-yl)-acetyl]-2,3-dimethoxy-phenoxy}-N-(2,3-difluoro-benzyl)-acetamide (compound 235),
2-{6-[2-(3,5-Dichloro-pyridin-4-yl)-acetyl]-2,3-dimethoxy-phenoxy}-N-(2-pyridin-2-yl-ethyl)-acetamide (compound 236),
2-{6-[2-(3,5-Dichloro-pyridin-4-yl)-acetyl]-2,3-dimethoxy-phenoxy}-N-(2-methyl-benzyl)-acetamide (compound 237),
2-{6-[2-(3,5-Dichloro-pyridin-4-yl)-acetyl]-2,3-dimethoxy-phenoxy}-N-(3-fluoro-benzyl)-acetamide (compound 238),
2-{6-[2-(3,5-Dichloro-pyridin-4-yl)-acetyl]-2,3-dimethoxy-phenoxy}-N-(3-methyl-benzyl)-acetamide (compound 239),
2-{6-[2-(3,5-Dichloro-pyridin-4-yl)-acetyl]-2,3-dimethoxy-phenoxy}-N-(4-methyl-benzyl)-acetamide (compound 240),
2-{6-[2-(3,5-Dichloro-pyridin-4-yl)-acetyl]-2,3-dimethoxy-phenoxy}-N-phenethyl-acetamide (compound 241),
2-{6-[2-(3,5-Dichloro-pyridin-4-yl)-acetyl]-2,3-dimethoxy-phenoxy}-N-(2-pyridin-4-yl-ethyl)-acetamide (compound 242),
2-{6-[2-(3,5-Dichloro-pyridin-4-yl)-acetyl]-2,3-dimethoxy-phenoxy}-N-(3-phenyl-propyl)-acetamide (compound 243),
N-(2-Chloro-benzyl)-2-{6-[2-(3,5-dichloro-pyridin-4-yl)-acetyl]-2,3-dimethoxy-phenoxy}-acetamide (compound 244),
2-{6-[2-(3,5-Dichloro-pyridin-4-yl)-acetyl]-2,3-dimethoxy-phenoxy}-N-(2-piperidin-1-yl-ethyl)-acetamide (compound 245),
N-(3-Chloro-benzyl)-2-{6-[2-(3,5-dichloro-pyridin-4-yl)-acetyl]-2,3-dimethoxy-phenoxy}-acetamide (compound 246),
2-{6-[2-(3,5-Dichloro-pyridin-4-yl)-acetyl]-2,3-dimethoxy-phenoxy}-N-(2-morpholin-4-yl-ethyl)-acetamide (compound 247),
N-(4-Chloro-benzyl)-2-{6-[2-(3,5-dichloro-pyridin-4-yl)-acetyl]-2,3-dimethoxy-phenoxy}-acetamide (compound 248),
2-{6-[2-(3,5-Dichloro-pyridin-4-yl)-acetyl]-2,3-dimethoxy-phenoxy}-N-(2-pyridin-3-yl-ethyl)-acetamide (compound 249), 2-{6-[2-(3,5-Dichloro-pyridin-4-yl)-acetyl]-2,3-dimethoxy-phenoxy}-N-(2-pyrrolidin-1-yl-ethyl)-acetamide (compound 250), N-(2-Acetylamino-ethyl)-2-{6-[2-(3,5-dichloro-pyridin-4-yl)-acetyl]-2,3-dimethoxy-phenoxy}-acetamide (compound 251), (R)-2-{6-[2-(3,5-Dichloro-pyridin-4-yl)-acetyl]-2,3-dimethoxy-phenoxy}-N-(2-hydroxy-2-phenyl-ethyl)-acetamide (compound 252), (S)-2-{6-[2-(3,5-Dichloro-pyridin-4-yl)-acetyl]-2,3-dimethoxy-phenoxy}-N-(2-hydroxy-2-phenyl-ethyl)-acetamide (compound 253), 2-{6-[2-(3,5-Dichloro-pyridin-4-yl)-acetyl]-2,3-dimethoxy-phenoxy}-N-thiophen-2-ylmethyl-acetamide (compound 254), 2-{6-[2-(3,5-Dichloro-pyridin-4-yl)-acetyl]-2,3-dimethoxy-phenoxy}-N-[3-(2-oxo-pyrrolidin-1-yl)-propyl]-acetamide (compound 255), (2R)-2-{6-[2-(3,5-Dichloro-pyridin-4-yl)-acetyl]-2,3-dimethoxy-phenoxy}-N-(2-hydroxy-indan-1-yl)-acetamide (compound 256), N-Cycloheptylmethyl-2-{6-[2-(3,5-dichloro-pyridin-4-yl)-acetyl]-2,3-dimethoxy-phenoxy}-acetamide (compound 257), 2-{6-[2-(3,5-Dichloro-pyridin-4-yl)-acetyl]-2,3-dimethoxy-phenoxy}-N-[2-(2-hydroxy-ethoxy)-ethyl]-acetamide (compound 258), 2-{6-[2-(3,5-Dichloro-pyridin-4-yl)-acetyl]-2,3-dimethoxy-phenoxy}-N-(4-dimethylamino-butyl)-acetamide (compound 259), 1-(3-Cyclopentyloxy-2-hydroxy-4-methoxy-phenyl)-2-(3,5-dichloro-pyridin-4-yl)-ethanone (compound 260), 1-(3-Cyclopropylmethoxy-2-hydroxy-4-methoxy-phenyl)-2-(3,5-dichloro-pyridin-4-yl)-ethanone (compound 261), 2-(3,5-Dichloro-pyridin-4-yl)-1-(3-ethoxy-2-hydroxy-4-methoxy-phenyl)-ethanone (compound 262), 2-(3,5-Dichloro-pyridin-4-yl)-1-(3-ethoxy-4-methoxy-2-phenethyloxy-phenyl)-ethanone (compound 263), 1-[2-(5-Cyclopropyl-[1,3,4]thiadiazol-2-ylmethoxy)-3-ethoxy-4-methoxy-phenyl]-2-(3,5-dichloro-pyridin-4-yl)-ethanone (compound 264), {6-[2-(3,5-Dichloro-pyridin-4-yl)-acetyl]-2-ethoxy-3-methoxy-phenoxy}-acetic acid benzyl ester (compound 265), 1-(3-Allyloxy-2-hydroxy-4-methoxy-phenyl)-2-(3,5-dichloro-pyridin-4-yl)-ethanone (compound 266), 2-{2-Allyloxy-6-[2-(3,5-dichloro-pyridin-4-yl)-acetyl]-3-methoxy-phenoxymethyl}-benzonitrile (compound 267), 1-(3-Allyloxy-4-methoxy-2-phenethyloxy-phenyl)-2-(3,5-dichloro-pyridin-4-yl)-ethanone (compound 268), 1-{3-Allyloxy-2-[2-(4-fluoro-phenyl)-ethoxy]-4-methoxy-phenyl}-2-(3,5-dichloro-pyridin-4-yl)-ethanone (compound 269), N-Benzyl-2-{6-[2-(3,5-dichloro-1-oxy-pyridin-4-yl)-acetyl]-2,3-dimethoxy-phenoxy}-acetamide (compound 270), 2-(3,5-Dichloro-1-oxy-pyridin-4-yl)-1-(3,4-dimethoxy-2-phenethyloxy-phenyl)-ethanone (compound 271), 2-(3,5-Dichloro-1-oxy-pyridin-4-yl)-1-{2-[2-(4-fluoro-phenyl)-ethoxy]-3,4-dimethoxy-phenyl}-ethanone (compound 272), 2-(3,5-Dichloro-1-oxy-pyridin-4-yl)-1-{3,4-dimethoxy-2-[2-(1-oxy-pyridin-4-yl)-ethoxy]-phenyl}-ethanone (compound 274), 2-(3,5-Dichloro-1-oxy-pyridin-4-yl)-1-(2-hydroxy-3,4-dimethoxy-phenyl)-ethanone (compound 275), 4-(2-{6-[2-(3,5-Dichloro-1-oxy-pyridin-4-yl)-acetyl]-2,3-dimethoxy-phenoxy}-ethyl)-benzonitrile (compound 276), 2-(3,5-Dichloro-pyridin-4-yl)-1-[3,4-dimethoxy-2-(2-pyridin-4-yl-ethoxy)-phenyl]-ethanone (compound 277), 4-(2-{6-[2-(3,5-Dichloro-pyridin-4-yl)-acetyl]-2,3-dimethoxy-phenoxy}-ethyl)-benzonitrile (compound 278), 2-(3,5-Dichloro-pyridin-4-yl)-1-[3,4-dimethoxy-2-(2-pyridin-2-yl-ethoxy)-phenyl]-ethanone (compound 279), 2-(3,5-Dichloro-pyridin-4-yl)-1-[3,4-dimethoxy-2-(2-pyridin-3-yl-ethoxy)-phenyl]-ethanone (compound 280), 2-(3,5-Dichloro-pyridin-4-yl)-1-{2-[2-(4-methanesulfinyl-phenyl)-ethoxy]-3,4-dimethoxy-phenyl}-ethanone (compound 281), 2-(3,5-Dichloro-pyridin-4-yl)-1-{2-[2-(4-methanesulfonyl-phenyl)-ethoxy]-3,4-dimethoxy-phenyl}-ethanone (compound 282), 2-(3,5-Dichloro-pyridin-4-yl)-1-[3,4-dimethoxy-2-(1-phenyl-propoxy)-phenyl]-ethanone (compound 283), 2-(3,5-Dichloro-pyridin-4-yl)-1-[3,4-dimethoxy-2-(2-phenyl-propoxy)-phenyl]-ethanone (compound 284), 2-(3,5-Dichloro-pyridin-4-yl)-1-[3,4-dimethoxy-2-(1-methyl-2-phenyl-ethoxy)-phenyl]-ethanone (compound 285), 2-{6-[2-(6-Chloro-pyrazin-2-yl)-acetyl]-2,3-dimethoxy-phenoxy}-N-propyl-acetamide (compound 286), 2-{6-[2-(3-Bromo-pyrazin-2-yl)-acetyl]-2,3-dimethoxy-phenoxy}-N-propyl-acetamide (compound 287), 2-{6-[2-(2,6-Dichloro-phenyl)-acetyl]-2,3-dimethoxy-phenoxy}-N-propyl-acetamide (compound 288), 2-[2,3-Dimethoxy-6-(2-pyridin-4-yl-acetyl)-phenoxy]-N-propyl-acetamide (compound 289), 2-[2,3-Dimethoxy-6-(2-quinolin-4-yl-acetyl)-phenoxy]-N-propyl-acetamide (compound 290), 2-[2,3-Dimethoxy-6-(2-pyrazin-2-yl-acetyl)-phenoxy]-N-propyl-acetamide (compound 291), 2-{6-[2-(3-Bromo-pyridin-4-yl)-acetyl]-2,3-dimethoxy-phenoxy}-N-propyl-acetamide (compound 292), 2-{6-[2-(3,5-Dibromo-pyridin-4-yl)-acetyl]-2,3-dimethoxy-phenoxy}-N-propyl-acetamide (compound 293), 2-{6-[2-(6-Chloro-pyrimidin-4-yl)-acetyl]-2,3-dimethoxy-phenoxy}-N-propyl-acetamide (compound 294), 2-{6-[2-(4-Chloro-pyridin-2-yl)-acetyl]-2,3-dimethoxy-phenoxy}-N-propyl-acetamide (compound 295), 2-{6-[2-(2-Chloro-pyridin-3-yl)-acetyl]-2,3-dimethoxy-phenoxy}-N-propyl-acetamide (compound 296), 2-{2,3-Dimethoxy-6-[2-(2-methoxy-pyridin-4-yl)-acetyl]-phenoxy}-N-propyl-acetamide (compound 297), 2-{6-[2-(2-Cyano-pyridin-4-yl)-acetyl]-2,3-dimethoxy-phenoxy}-N-propyl-acetamide (compound 298), 2-[2,3-Dimethoxy-6-(2-pyridazin-3-yl-acetyl)-phenoxy]-N-propyl-acetamide (compound 299), 2-(2-tert-Butylamino-3,5-dichloro-pyridin-4-yl)-1-{2-[2-(4-fluoro-phenyl)-ethoxy]-3,4-dimethoxy-phenyl}-ethanone (compound 300), 2-(2-amino-3,5-dichloro-pyridin-4-yl)-1-{2-[2-(4-fluoro-phenyl)-ethoxy]-3,4-dimethoxy-phenyl}-ethanone (compound 301), 2-(3,5-Dichloro-pyridin-4-yl)-1-(4-ethoxy-3-methoxy-2-phenethyloxy-phenyl)-ethanone (compound 302), {6-[2-(3,5-Dichloro-pyridin-4-yl)-acetyl]-2,3-dimethoxy-phenoxy}-acetic acid (compound 504), 2-tert-butoxycarbonylmethoxy-3,4-dimethoxy-benzoic acid methyl ester (compound 506a), 2-carboxymethoxy-3,4-dimethoxy-benzoic acid methyl ester (compound 506b), 3,4-Dimethoxy-2-propylcarbamoylmethoxy-benzoic acid methyl ester (compound 506c), or
2-{6-[2-(3,5-Dichloro-pyridin-4-yl)-acetyl]-2,3-dimethoxy-phenoxy}-N-ethyl-acetamide (compound 305),
and pharmaceutically acceptable and physiologically cleavable esters, pharmaceutically acceptable salts, hydrates, N-oxides or solvates thereof.

In one preferred embodiment of the present invention $X_3$ represents N, and $X_1$, $X_2$, $X_4$ and $X_5$ represent —CH—. In another embodiment $X_1$ represents N, and $X_2$, $X_3$, $X_4$ and $X_s$ represent —CH—. In another embodiment $X_2$ represents N, and $X_1$, $X_3$, $X_4$ and $X_5$ represent —CH—. In another embodiment $X_4$ represents N, and $X_1$, $X_2$, $X_3$ and $X_5$ represent —CH—, or $X_5$ represents N, and $X_1$, $X_2$, $X_3$ and $X_4$ represent —CH—. In a further preferred embodiment $X_1$, $X_2$, $X_3$, $X_4$ and $X_5$ represent —CH—. In yet another embodiment $X_1$ and $X_4$ represent N, and $X_2$, $X_3$ and $X_5$ represent —CH—, or $X_2$ and $X_s$ represent N and $X_1$, $X_3$ and $X_4$ represent —CH—, or $X_3$ and $X_s$ represent N and $X_1$, $X_2$ and $X_4$ represent —CH—. In a further embodiment $X_1$ and $X_2$ represent N, and $X_3$, $X_4$ and $X_s$ represent —CH—, or $X_4$ and $X_5$ represent N and $X_1$, $X_2$ and $X_3$ represent —CH—.

Suitable substituents $R_{11}$ of ring B comprise halogens such as chloro, bromo or fluoro, cyano, methoxy, ethoxy, propoxy or alkylamines such as tert.-butylamine.

Substituents $R_{11}$ of ring B may preferably be attached in the ortho (2 and 6 position) and/or meta (3 and 5 position) position from where ring B is attached to the acetophenone:

In another embodiment when $R_3$ is hydrogen, then one of $X_1$, $X_2$, $X_3$, $X_4$ or $X_5$ is nitrogen.

In one or more embodiments of the present invention, the compounds of formula I as defined above are useful in therapy and in particular useful for treatment of dermal diseases.

In one or more embodiments of the present invention, the dermal disease or condition is selected from proliferative and inflammatory skin disorders, psoriasis, cancer, epidermal inflammation, alopecia, skin atrophy, steroid induced skin atrophy, skin ageing, photo skin ageing, acne, dermatitis, atopic dermatitis, seborrheic dermatitis, contact dermatitis, urticaria, pruritis, and eczema.

The compounds of formula I may be obtained in crystalline form either directly by concentration from an organic solvent or by crystallisation or recrystallisation from an organic solvent or mixture of said solvent and a cosolvent that may be organic or inorganic, such as water. The crystals may be isolated in essentially solvent-free form or as a solvate, such as a hydrate. The invention covers all crystalline forms, such as polymorphs and pseudopolymorphs, and also mixtures thereof.

Compounds of formula I may or may not comprise asymmetrically substituted (chiral) carbon atoms which give rise to the existence of isomeric forms, e.g. enantiomers and possibly diastereomers. The present invention relates to all such isomers, either in pure form or as mixtures thereof (e.g. racemates). Pure stereoisomeric forms of the compounds and the intermediates of this invention may be obtained by the application of procedures known in the art. The various isomeric forms may be separated by physical separation methods such as selective crystallization and chromatographic techniques, e.g. liquid chromatography using chiral stationary phases. Enantiomers may be separated from each other by the selective crystallization of their diastereomeric salts with optically active amines, such as l-ephedrine. Alternatively, enantiomers may be separated by chromatographic techniques using chiral stationary phases. Said pure stereoisomeric forms may also be derived from the corresponding pure stereoisomeric forms of the appropriate starting materials, provided that the reaction occurs stereoselectively or stereospecifically. Preferably, if a specific stereoisomer is desired, said compound will be synthesized by stereoselective or stereospecific methods of preparation. These methods will advantageously employ chiral pure starting materials.

Compounds of the present invention, optionally in combination with other active compounds, would be useful for the treatment of dermal diseases or conditions, or acute or chronic cutaneous wound disorders, in particular for the treatment of proliferative and inflammatory skin disorders, psoriasis, cancer, epidermal inflammation, alopecia, skin atrophy, steroid induced skin atrophy, skin ageing, photo skin ageing, acne, dermatitis, atopic dermatitis, seborrheic dermatitis, contact dermatitis, urticaria, pruritis, and eczema.

Besides being useful for human treatment, the compounds of the present invention may also be useful for veterinary treatment of animals including mammals such as horses, cattle, sheep, pigs, dogs, and cats.

For use in therapy, compounds of the present invention are typically in the form of a pharmaceutical composition. The invention therefore relates to a pharmaceutical composition comprising a compound of formula I, optionally together with one or more other therapeutically active compound(s), together with a pharmaceutically acceptable excipient, vehicle or carrier(s). The excipient must be "acceptable" in the sense of being compatible with the other ingredients of the composition and not deleterious to the recipient thereof.

Conveniently, the active ingredient comprises from 0.05-99.9% by weight of the formulation.

In the form of a dosage unit, the compound may be administered one or more times a day at appropriate intervals, always depending, however, on the condition of the patient, and in accordance with the prescription made by the medical practitioner. Conveniently, a dosage unit of a formulation contain between 0.1 mg and 1000 mg, preferably between 1 mg and 100 mg, such as 5-50 mg of a compound of formula I.

A suitable dosage of the compound of the invention will depend, inter alia, on the age and condition of the patient, the severity of the disease to be treated and other factors well known to the practising physician. The compound may be administered either orally, parenterally or topically according to different dosing schedules, e.g. daily or with weekly intervals. In general a single dose will be in the range from 0.01 to 400 mg/kg body weight. The compound may be administered as a bolus (i.e. the entire daily dosis is administered at once) or in divided doses two or more times a day.

In the context of topical treatment it may be more appropriate to refer to a "usage unit", which denotes a single dose which is capable of being administered to a patient, and which may be readily handled and packed, remaining as a physically and chemically stable unit dose comprising either the active material as such or a mixture of it with solid or liquid pharmaceutical diluents or carriers.

The term "usage unit" in connection with topical use means a unitary, i.e. a single dose, capable of being administered topically to a patient in an application per square centimetre of the infected area of from 0.1 mg to 10 mg and preferably from 0.2 mg to 1 mg of the active ingredient in question.

It is also envisaged that in certain treatment regimes, administration with longer intervals, e.g. every other day, every week, or even with longer intervals may be beneficial.

If the treatment involves administration of another therapeutically active compound It is recommended to consult *Goodman & Gilman's The Pharmacological Basis of Thera-*

*peutics*, 9<sup>th</sup> Ed., J. G. Hardman and L. E. Limbird (Eds.), McGraw-Hill 1995, for useful dosages of said compounds.

The administration of a compound of the present invention with one or more other active compounds may be either concomitantly or sequentially.

The formulations include e.g. those in a form suitable for oral (including sustained or timed release), rectal, parenteral (including subcutaneous, intraperitoneal, intramuscular, intraarticular and intravenous), transdermal, ophthalmic, topical, nasal or buccal administration.

The formulations may conveniently be presented in dosage unit form and may be prepared by any of the methods well known in the art of pharmacy, e.g. as disclosed in Remington, *The Science and Practice of Pharmacy*, 21ed ed., 2005.

All methods include the step of bringing the active ingredient into association with the carrier, which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid, such as ethanol or glycerol; or in the form of an oil-in-water emulsion or a water-in-oil emulsion. Such oils may be edible oils, such as e.g. cottonseed oil, sesame oil, coconut oil or peanut oil. Suitable dispersing or suspending agents for aqueous suspensions include synthetic or natural gums such as tragacanth, alginate, acacia, dextran, sodium carboxymethylcellulose, gelatin, methylcellulose, hydroxypropylmethylcellulose, hydroxypropylcellulose, carbomers and polyvinylpyrrolidone. The active ingredients may also be administered in the form of a bolus, electuary or paste.

A tablet may be made by compressing or moulding the active ingredient optionally with one or more accessory ingredients. Compressed tablets may be prepared by compressing, in a suitable machine, the active ingredient(s) in a free-flowing form such as a powder or granules, optionally mixed by a binder, such as e.g. lactose, glucose, starch, gelatine, acacia gum, tragacanth gum, sodium alginate, carboxymethylcellulose, methylcellulose, hydroxypropylmethylcellulose, polyethylene glycol, waxes or the like; a lubricant such as e.g. sodium oleate, sodium stearate, magnesium stearate, sodium benzoate, sodium acetate, sodium chloride or the like; a disintegrating agent such as e.g. starch, methylcellulose, agar, bentonite, croscarmellose sodium, sodium starch glycollate, crospovidone or the like or a dispersing agent, such as polysorbate 80. Moulded tablets may be made by moulding, in a suitable machine, a mixture of the powdered active ingredient and suitable carrier moistened with an inert liquid diluent.

Formulations for rectal administration may be in the form of suppositories in which the compound of the present invention is admixed with low melting water soluble or insoluble solids such as cocoa butter, hydrogenated vegetable oils, polyethylene glycol or fatty acids esters of polyethylene glycols, while elixirs may be prepared using myristyl palmitate.

Formulations suitable for parenteral administration conveniently comprise a sterile oily or aqueous preparation of the active ingredients, which is preferably isotonic with the blood of the recipient, e.g. isotonic saline, isotonic glucose solution or buffer solution. The formulation may be conveniently sterilised by for instance filtration through a bacteria retaining filter, addition of sterilising agent to the formulation, irradiation of the formulation or heating of the formulation. Liposomal formulations as disclosed in e.g. Encyclopedia of Pharmaceutical Technology, vol. 9, 1994, are also suitable for parenteral administration.

Alternatively, the compounds of formula I may be presented as a sterile, solid preparation, e.g. a freeze-dried powder, which is readily dissolved in a sterile solvent immediately prior to use.

Transdermal formulations may be in the form of a plaster or a patch.

Formulations suitable ophthalmic administration may be in the form of a sterile aqueous preparation of the active ingredients, which may be in microcrystalline form, for example, in the form of an aqueous microcrystalline suspension. Liposomal formulations or biodegradable polymer systems e.g. as disclosed in Encyclopedia of Pharmaceutical Technology, vol. 2, 1989, may also be used to present the active ingredient for ophthalmic administration.

Formulations suitable for topical or ophthalmic administration include liquid or semi-liquid preparations such as liniments, lotions, gels, applicants, oil-in-water or water-in-oil emulsions such as creams, ointments or pastes; or solutions or suspensions such as drops. Compositions for ophthalmic treatment may preferably additionally contain a cyclodextrin.

For topical administration, the compound of formula I may typically be present in an amount of from 0.01 to 20% by weight of the composition, such as 0.1% to about 10%, but may also be present in an amount of up to about 50% of the composition.

Formulations suitable for nasal or buccal administration include powder, self-propelling and spray formulations, such as aerosols and atomisers. Such formulations are disclosed in greater detail in e.g. Modern Pharmaceutics, 2nd ed., G. S. Banker and C. T. Rhodes (Eds.), page 427-432, Marcel Dekker, New York; Modern Pharmaceutics, 3<sup>th</sup> ed., G. S. Banker and C. T. Rhodes (Eds.), page 618-619 and 718-721, Marcel Dekker, New York and Encyclopedia of Pharmaceutical Technology, vol. 10, J. Swarbrick and J. C. Boylan (Eds), page 191-221, Marcel Dekker, New York.

In addition to the aforementioned ingredients, the formulations of a compound of formula I may include one or more additional ingredients such as diluents, buffers, flavouring agents, colourant, surface active agents, thickeners, preservatives, e.g. methyl hydroxybenzoate (including anti-oxidants), emulsifying agents and the like.

When the active ingredient is administered in the form of salts with pharmaceutically acceptable non-toxic acids or bases, preferred salts are for instance easily water-soluble or slightly soluble in water, in order to obtain a particular and appropriate rate of absorption.

The pharmaceutical composition may additionally comprise one or more other active components conventionally used in the treatment of dermal disease or conditions, e.g. selected from the group consisting of proliferative and inflammatory skin disorders, psoriasis, cancer, epidermal inflammation, alopecia, skin atrophy, steroid induced skin atrophy, skin ageing, photo skin ageing, acne, dermatitis, atopic dermatitis, seborrheic dermatitis, contact dermatitis, urticaria, pruritis, and eczema.

Examples of such additional active components may for example be selected from the group consisting of glucocorticoids, vitamin D and vitamin D analogues, antihistamines, platelet activating factor (PAF) antagonists, anticholinergic agents, methylxanthines, β-adrenergic agents, COX-2 inhibitors, salicylates, indomethacin, flufenamate, naproxen, timegadine, gold salts, penicillamine, serum cholesterol lowering agents, retinoids, zinc salts and salicylazosulfapyridine.

Methods of Preparation

The compounds of the present invention can be prepared in a number of ways well known to those skilled in the art of synthesis. The compounds of formula I may for example be prepared using the reactions and techniques outlined below together with methods known in the art of synthetic organic chemistry, or variations thereof as appreciated by those skilled in the art. Preferred methods include, but are not limited to, those described below. The reactions are carried out in solvents appropriate to the reagents and materials employed and suitable for the transformations being effected. Also, in the synthetic methods described below, it is to be understood that all proposed reaction conditions, including choice of solvent, reaction atmosphere, reaction temperature, duration of experiment and work-up procedures, are chosen to be conditions of standard for that reaction, which should be readily recognized by one skilled in the art. Not all compounds falling into a given class may be compatible with some of the reaction conditions required in some of the methods described. Such restrictions to the substituents which are compatible with the reaction conditions will be readily apparent to one skilled in the art and alternative methods can be used. The compounds of the present invention or any intermediate may be purified if required using standard methods well known to a synthetic organist chemist, e.g. methods described in "Purification of Laboratory Chemicals", 5$^{th}$ ed. 2003. Starting materials are either known compounds, commercially available, or they may be prepared by routine synthetic methods well known to a person skilled in the art.

GENERAL PROCEDURES, PREPARATIONS AND EXAMPLES $^1$H nuclear magnetic resonance (NMR) spectra were usually recorded at 300 MHz. Chemical shift values (δ, in ppm) are quoted in the specified solvent relative to internal tetramethylsilane (δ=0.00) or chloroform (δ=7.25) standards. The value of a multiplet, either defined (doublet (d), triplet (t), quartet (q)) or not (m) at the approximate mid point is given unless a range is quoted. (bs) indicates a broad singlet. The organic solvents used were usually anhydrous. Chromatography was performed on Merck silica gel 60 (0.040-0.063 mm). The solvent ratios indicated refer to v:v unless otherwise noted.

The following abbreviations have been used throughout:
ADDP 1,1'-(Azodicarbonyl)dipiperidine
AIBN Azobisisobutyronitrile
Ar-Me aryl-methyl
DCE dichloroethane
DCM dichloromethane
DMF N,N'-Dimethylformamide
DMSO dimethyl sulfoxide
Et ethyl
h hour(s)
HATU O-(7-Azabenzotriazol-1-yl)-1,1,3,3-tetramethyluronium hexafluorophosphate
HetAr-Me heteroaryl-methyl
L litre
LDA lithium diisopropylamide
LiHMDS lithium hexamethyldisilazide
m milli
MCPBA m-chloroperoxybenzoic acid
Me methyl
NBS N-bromosuccinimide
NMP 1-methyl-2-pyrrolidinone
NMR nuclear magnetic resonance
rt room temperature
RT retention Time
TBAD di-tert-butyl-azodicarboxylate
TFA trifluoroacetic acid
THF tetrahydrofuran
TIS triethylsilane
v volume Preparative HPLC/MS Preparative HPLC/MS was performed on a Dionex APS-system with two Shimadzu PP150 prep. pumps and a Thermo MSQ Plus mass spectrometer. Column: Waters XTerra C-18, 150 mm×19 mm, 5 µm; solventsystem: A=water (0.1% formic acid) and B=acetonitrile (0.1% formic acid); flow rate=18 mL/min; method (10 min): Linear gradient method going from 10% B to 100% B in 6 minutes and staying at 100% B for another 2 minutes. The fractions were collected based on ion traces of relevant ions and FDA signal (240-400 nm).

Analytical HPLC/MS

Method A:

Analytical HPLC/MS was performed on a Dionex APS-system with a P680A analytical pump and a Thermo MSQ Plus mass spectrometer. Column: Waters XTerra C-18, 150 mm×4.6 mm, 5 µm; solventsystem: A=water (0.1% formic acid) and B=acetonitrile (0.1% formic acid); flow rate=1.0 mL/min; method (10 min): Linear gradient method going from 10% B to 100% B in 6.6 minutes and staying at 100% B for another 1.5 minutes.

Method B:

Analytical HPLC/MS was performed on a system consisting of a Waters 2795 HPLC, Micromass ZQ mass spectrometer, Waters 996 PDA. Column: Waters XTerra C-18, 50 mm×3.0 mm, 5 µm; solventsystem: A=water:acetonitrile 95:5 (0.05% formic acid) and B=acetonitrile (0.05% formic acid); flow rate=1.0 ml/min; method (8 min): Linear gradient method going from 10% B to 100% B in 6.0 minutes and staying at 100% B for 1 minute.

GENERAL METHODS AND EXAMPLES

The compounds of the invention may for example be prepared according to the following non-limiting general methods and examples:

Method a)

Mono or dialkylation of compounds with formula Ia

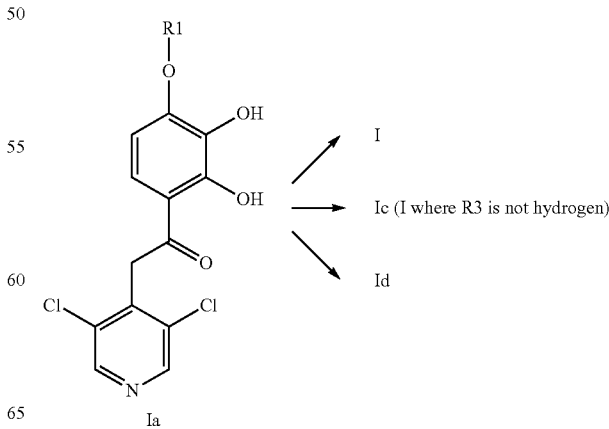

wherein R1 is as described herein, with suitable alkyl or alkenyl chlorides, bromides, iodides, mesylates or tosylates under basic conditions (Protective Groups in Organic Chemistry, John Wiley & sons, Ed: T. Greene and P. G. Wuts, 3$^{rd}$ edition (1999), p 249-72), or by suitable alcohols, e.g. alkyl alcohols, using Mitsunobu conditions (see Synthesis (1981), 1; Tet. Lett. (1993), 34, 1639-42 and Eur. J. Org. Chem. (2004), 2763-72), in a suitable solvent such as THF, benzene or DMF. The reaction may either be one-pot or in two subsequent steps.

Method b)

Alkylation of compounds with formula Ic,

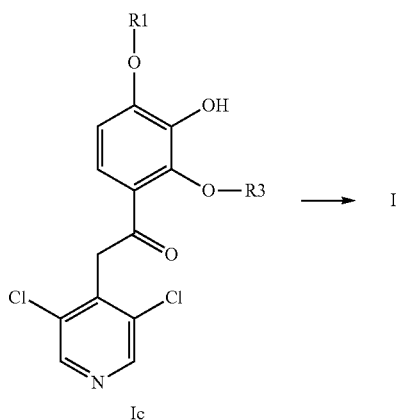

Ic wherein R1 and R3 (R3≠H) are as described herein, with alkyl, alkenyl or alkynyl chlorides, bromides, Iodides, mesylates or tosylates under basic conditions or with alkyl alcohols using Mitsunobu conditions in a suitable solvent such as THF, acetone, benzene, toluene or DMF.

Method c)

Alkylation of compounds with formula Id (I where R3=hydrogen),

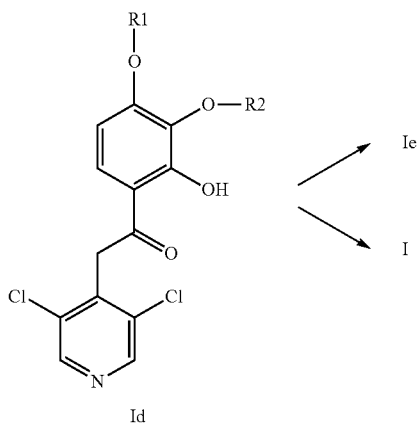

Id wherein R1 and R2 (R2≠H) are as described herein, with alkyl, alkenyl or alkynyl chlorides, bromides, iodides, mesylates or tosylates under basic conditions or by alkyl alcohols using Mitsunobu conditions in a suitable solvent such as THF, acetone, benzene, toluene or DMF.

Method d)

Amide formation of compounds with formula Ie,

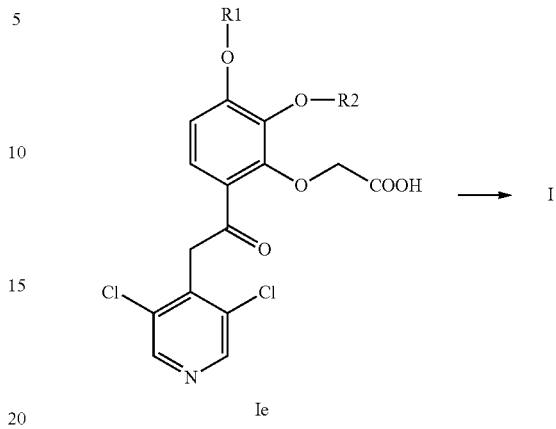

Ie wherein R1 and R2 are as described herein, with primary or secondary amines using for example a coupling reagent such as HATU (Carpino, L. A. J. Am. Chem. Soc. (1993), 115, 4397), or any other standard peptide coupling reagents (Larry. Yet, Albany Molecular Research, Technical Reports Vol 4, number 1, p 1-7).

Starting materials of formula Ia-Ie may be prepared according to standard procedures well known to a person skilled in the art. E.g. commercially available 2,3,4-Methoxy benzoic acid (Aldrich) is esterified with MeI in the presence of a suitable base, such as $K_2CO_3$ or $Et_3N$. In a suitable solvent such as DMF, THF or DCM at temperatures from it to 100° C. The resulting ester is then condensed with 3,5-dichloro-4-methylpyridine (e.g. prepared according to either J. Org. Chem. (1961), 26, 789-92, Heterocycles (2001), 55, 2075-84 or PCT9414742) in the presence of a suitable base, such as LDA or LiHMDS, in a suitable solvent such as THF, at temperatures from minus 78° C. to rt. The resulting ketone is deprotected either:

A) In the presence of a suitable acid, such as HI or HBr in a suitable solvent such as AcOH at temperatures from 50° C. to 120° C. to provide compounds of formula Ia.

B) In the presence of a suitable Lewis acid, such as $BCl_3$, $BBr_3$ or $AlCl_3$ in a suitable solvent, such as dichloromethane at temperatures from 0° to it to provide compounds of formula Id.

Dialkylation of compounds with formula Ia with alkenyl chlorides, bromides, Iodides, mesylates or tosylates in the presence of a suitable base, such as $K_2CO_3$ or $Et_3N$ in a suitable solvent such as DMF, NMP, THF or DCM at temperatures from rt to 100° C. provide compounds of formula Ib. Subsequent deprotection of compounds with formula Ib in the presence of a suitable Lewis acid, such as $BCl_3$, $BBr_3$ or $AlCl_3$ in a suitable solvent, such as dichloromethane at temperatures from 0° to rt, followed by re-alkylation with alkenyl chlorides, bromides, iodides, mesylates or tosylates in the presence of a suitable base, such as $K_2CO_3$ or $Et_3N$ in a suitable solvent such as DMF, NMP, THF or DCM at temperatures from it to 100° C. provide unsymmetrical compounds of formula Ib.

Selective monoalkylation of compounds with formula Ia with alkyl, alkenyl or alkynyl bromides or iodides in the presence of a suitable base, such as $K_2CO_3$ in a suitable solvent such as DMF or NMP at temperatures from it to 100° C. provide compounds of formula Ic or id.

Alkylation of compounds with formula Id with alkyl chloro or bromoacetate in the presence of suitable base, such as K$_2$CO$_3$ in a suitable solvent such as DMF or NMP at temperatures from it to 100° C. followed by hydrolysis of the carboxylic ester under standard conditions (Protective Groups in Organic Chemistry, John Wiley & sons, Ed; T. Greene and P. G. Wuts, 3$^{rd}$ edition (1999), p 384-86) provide compounds of formula Ie.

Preparation 1

Compound 501

Methyl 2,3,4-trimethoxybenzoate

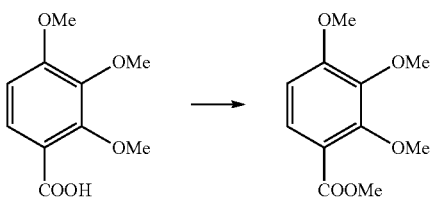

2,3,4-Trimethoxybenzoic acid (Aldrich) (20 g, 94 mmol) was dissolved in dry DMF (250 mL). K$_2$CO$_3$ (13 g, 94 mmol) and MeI (6.5 mL, 103.4 mmol) were added and the reaction mixture was heated to 50° C. for 5 h. The reaction mixture was cooled tort and water (250 mL) was added. EtOAc (1 L) was added and the organic phase was washed with water (3×500 mL) and finally with NaCl (sat.). The organic phase washed dried over MgSO$_4$, filtered and concentrated in vacuo. Redissolved in toluene and evaporated. Methyl 2,3,4-trimethoxybenzoate was obtained as a slightly yellow oil. $^1$H NMR (CDCl$_3$) δ=7.60 (1H, d), 6.70 (1H, d), 3.99 (3H, s), 3.91 (3H, s), 3.89 (3H, s), 3.88 (3H, s). Yield 21 g (99%).

Preparation 2

Compound 502

2-(3,5-Dichloro-pyridin-4-yl)-1-(2,3,4-trimethoxy-phenyl)-ethanone

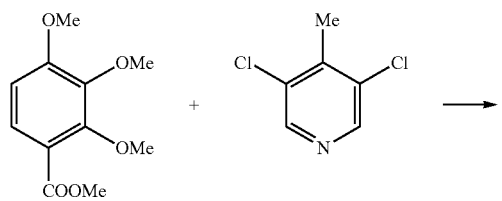

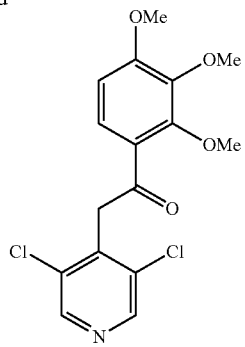

Methyl 2,3,4-trimethoxybenzoate from preparation 1 (2.7 g, 10 mmol) and 3,5-dichloro-4-methylpyridine (prepared according to literature procedures) was dissolved in dry THF (40 mL). The reaction was cooled on ice and treated dropwise (during 5 minutes) with 1M lithium bis(trimethylsilyl)amide (12 mL, 12 mmol). After 1.5 hours at 0° C. the reaction was quenched with NH$_4$Cl (sat, 100 mL). The organic products were extracted with EtOAc (2×100 mL), and the combined organic phases washed with NaCl (sat, 100 mL). The organic phase was dried over Na$_2$SO$_4$, evaporated in vacuo and purified by flash chromatography using a gradient of EtOAc in heptane as eluent. 2-(3,5-Dichloro-pyridin-4-yl)-1-(2,3,4-trimethoxy-phenyl)-ethanone was obtained as a white solid. $^1$H NMR (CDCl$_3$) δ=8.43 (2H, s), 7.55 (1H, d), 6.69 (1H, d), 4.61 (2H, s), 4.02 (3H, s), 3.87 (3H, s), 3.84 (3H, s). Yield 2.3 g (65%).

Example 1

Compound 101

2-(3,5-Dichloro-pyridin-4-yl)-1-(2-hydroxy-3,4-dimethoxy-phenyl)-ethanone

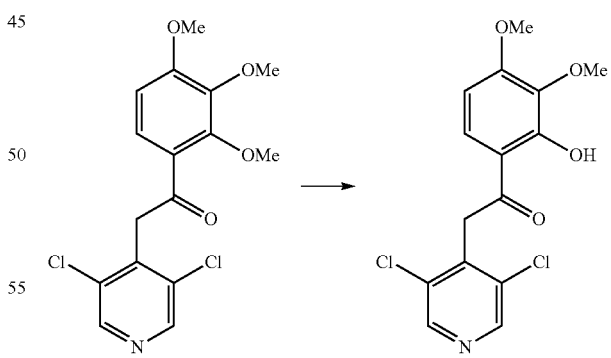

2-(3,5-Dichloro-pyridin-4-yl)-1-(2,3,4-trimethoxy-phenyl)-ethanone from preparation 2 (20 g, 56 mmol) was dissolved in DCM (75 mL) under argon. BCl$_3$ (95 mL of a 1M solution in DCM) was added slowly at room temperature for 2 hours. Water (50 mL) was added slowly followed by EtOH (200 mL). The white precipitate was filtered and re-crystallised from EtOH. 2-(3,5-Dichloro-pyridin-4-yl)-1-(2-hydroxy-3,4-dimethoxy-phenyl)-ethanone was obtained as a white solid. $^1$H NMR (CDCl$_3$) δ=11.92 (1H, s), 8.54 (2H, s), 7.68 (1H, d), 6.60 (1H, d), 4.67 (2H, s), 3.98 (3H, s), 3.90 (3H, s). Yield 14.2 g (74%)

Preparation 3

Compound 503

2-(3,5-Dichloro-pyridin-4-yl)-1-(2,3-dihydroxy-4-methoxy-phenyl)-ethanone

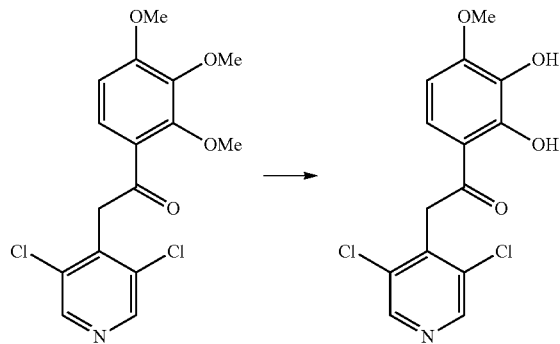

2-(3,5-Dichloro-pyridin-4-yl)-1-(2,3,4-trimethoxy-phenyl)-ethanone from preparation 2 (1.25 g, 3.5 mmol) was dissolved in AcOH (100%, 9.25 mL) under argon. HI (55-58%, 4.55 mL) was added and the reaction mixture was heated at 80° C. for 18 hours. The reaction mixture was cooled to rt and evaporated in vacuo. NaHCO$_3$ (sat., 150 mL) was added slowly followed by NaCl (sat., 50 mL). The organic products were extracted with EtOAc (4×100 mL). The combined organic phases were washed twice with NaCl (sat, 100 mL), Na$_2$S$_2$O$_3$ (10%, 100 mL), dried over Na$_2$SO$_4$ and evaporated in vacuo. 2-(3,5-Dichloro-pyridin-4-yl)-1-(2,3-dihydroxy-4-methoxy-phenyl)-ethanone was obtained as a brown solid. $^1$H NMR (CDCl$_3$) δ=11.88 (1H, s), 8.54 (2H, s), 7.51 (1H, d), 6.60 (1H, d), 5.62 (1H, bs), 4.67 (2H, s), 4.00 (3H, s). Yield 0.935 g (81%)

General Procedure for Preparation of Compounds with Formula If, Wherein R3 is as Defined Herein (R3≠Hydrogen):

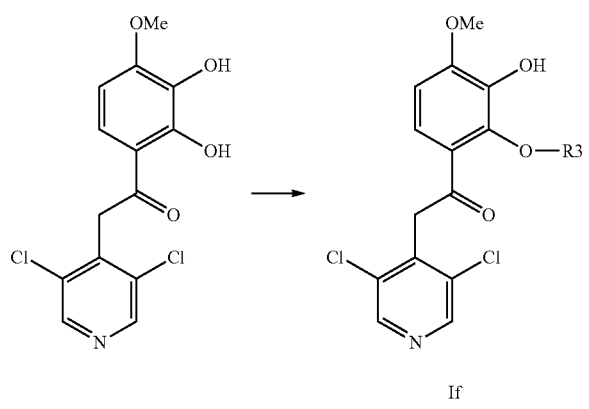

If 2-(3,5-Dichloro-pyridin-4-yl)-1-(2,3-dihydroxy-4-methoxy-phenyl)-ethanone (0.1 mmol) from preparation 3 was dissolved in dry DMF (0.75 mL). K$_2$CO$_3$ (0.1 mmol) was added followed by 0.1 mmol of an alkyl bromide or iodide.

The reaction mixture was heated to 70° C. for 18 hours. After cooling to rt, water (1 mL) was added and the organic products were extracted with EtOAc (3×1 mL). The combined organic phases were washed with NaCl (sat, 1 mL) and then dried over Na$_2$SO$_4$. The pure compounds were obtained by redissolving the reaction mixture in DMSO followed by standard preparative HPLC purification.

Using this procedure the following compounds were obtained:

Example 2

Compound 102

2-(3,5-Dichloro-pyridin-4-yl)-1-(3-hydroxy-2,4-dimethoxy-phenyl)-ethanone LC/MS (METHOD B): (m/z) 342.1 (MH+); RT=3.34 min; purity (UV)=100% Alkyl halide: Methyl iodide Example 3

Compound 103

1-(2-Allyloxy-3-hydroxy-4-methoxy-phenyl)-2-(3,5-dichloro-pyridin-4-yl)-ethanone LC/MS (METHOD B): (m/z) 368.2 (MH+); RT=3.81 min; purity (UV)=100%
Alkyl halide: Allyl bromide General Procedure for Preparation of Compounds with Formula Ig, Wherein R2=R3 and are as defined herein (R3≠hydrogen):

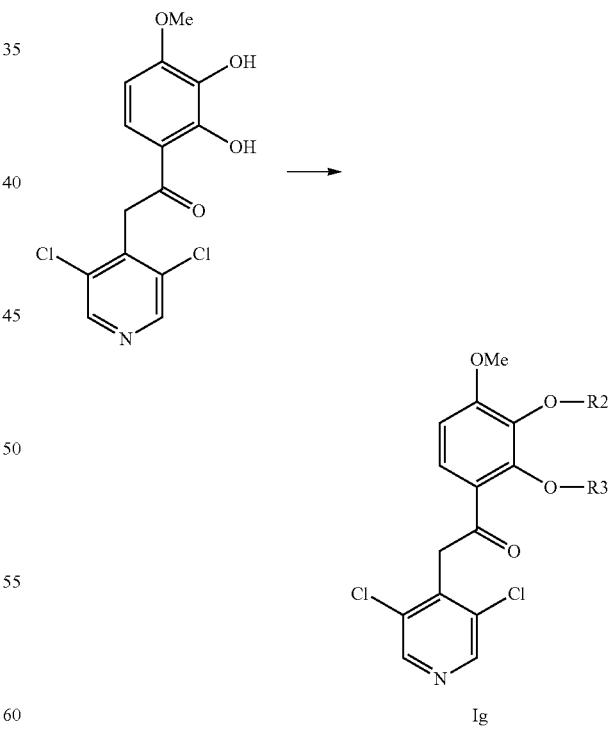

Ig 2-(3,5-Dichloro-pyridin-4-yl)-1-(2,3-dihydroxy-4-methoxy-phenyl)-ethanone (0.1 mmol) from preparation 3 was dissolved in dry DMF (0.75 mL). K$_2$CO$_3$ (0.2 mmol) was added followed by 0.2 mmol of an alkyl chloride, bromide or iodide. In the case of the alkyl chlorides additional KI (0.05 mmol) was added. The reaction mixture was heated to 70° C. for 18 hours. After cooling to it, water (1 mL) was added and the organic products were extracted with EtOAc (3×1 mL). The combined organic phases were washed with NaCl (sat, 1 mL) and then dried over $Na_2SO_4$. The pure compounds were obtained by redissolving the reaction mixture in DMSO followed by standard preparative HPLC purification.

Using this procedure the following compounds were obtained:

Example 4

Compound 104

2-(3,5-Dichloro-pyridin-4-yl)-1-(2,3-diethoxy-4-methoxy-phenyl)-ethanone

LC/MS (METHOD B): (m/z) 384.1 (MH+); RT=4.69 min; purity (UV)=100% Alkyl halide: Ethyl iodide Example 5

Compound 105

{2-tert-Butoxycarbonylmethoxy-6-[2-(3,5-dichloro-pyridin-4-yl)-acetyl]-3-methoxy-phenoxy}-acetic acid tert-butyl ester LC/MS (METHOD B): (m/z) 554.3 (MH+); RT=5.39 min; purity (UV)=100%

Alkyl halide: Tert-butyl bromoacetate

Example 6

Compound 106

1-(2,3-Bis-allyloxy-4-methoxy-phenyl)-2-(3,5-dichloro-pyridin-4-yl)-ethanone

LC/MS (METHOD B): (m/z) 408.2 (MH+); RT=4.94 min; purity (UV)=100%

Alkyl halide: Allyl bromide

Example 107

Compound 107

1-(2,3-Bis-difluoromethoxy-4-methoxy-phenyl)-2-(3,5-dichloro-pyridin-4-yl)-ethanone LC/MS (METHOD B): (m/z) 428.1 (MH+); RT=4.23 min; purity (UV)=100%

Alkyl halide: Sodium chlorodifluoroacetate. Heated to 100° C. for 30 minutes.

General Procedure for Preparation of Compounds with Formula Ih, Wherein R3 (R3≠Hydrogen) is as Defined Above:

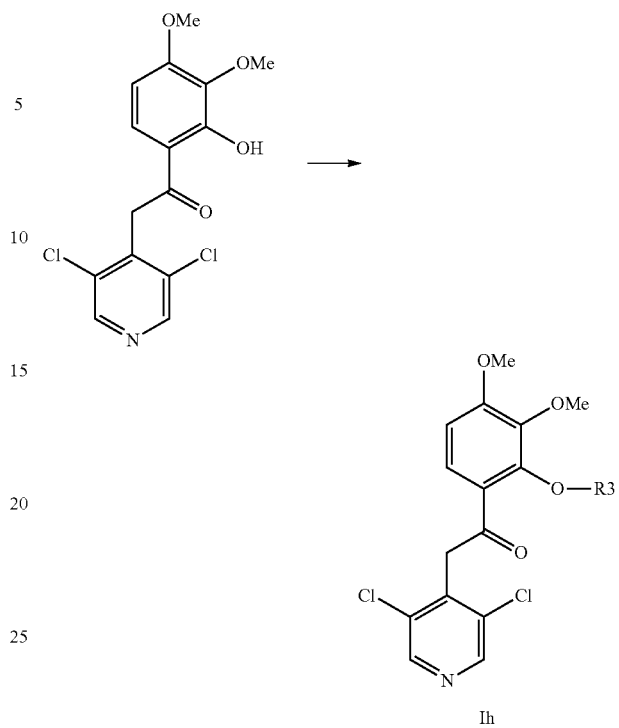

2-(3,5-Dichloro-pyridin-4-yl)-1-(2-hydroxy-3,4-methoxy-phenyl)-ethanone (0.035 mmol) from example 1 was dissolved in dry DMSO (0.25 mL). Aqueous $K_2CO_3$ (0.025 mL of a 2M) was added followed by 0.053 mmol of an alkyl chloride, bromide or iodide dissolved in 0.025 mL DMSO. The reaction mixture was left at rt for 48 hours. The pure compounds were obtained by standard preparative HPLC purification.

Using this procedure the following compounds were obtained:

Example 108

Compound 108

2-(3,5-Dichloro-pyridin-4-yl)-1-[3,4-dimethoxy-2-(5-methyl-isoxazol-3-ylmethoxy)-phenyl]-ethanone LC/MS (METHOD B): (m/z) 437.1 (MH+); RT=4.01 min; purity (UV)=100%

Alkyl halide: 3-Chloromethyl-5-methylisoxazole

Example 109

Compound 109

2-(3,5-Dichloro-pyridin-4-yl)-1-[3,4-dimethoxy-2-(2-methoxy-ethoxy)-phenyl]-ethanone LC/MS (METHOD B): (m/z) 400.1 (MH+); RT=3.90 min; purity (UV)=100%

Alkyl halide: 1-Bromo-2-methoxy-ethane

Example 110

Compound 110

1-(2-But-2-ynyloxy-3,4-dimethoxy-phenyl)-2-(3,5-dichloro-pyridin-4-yl)-ethanone LC/MS (METHOD B): (m/z) 394.1 (MH+); RT=4.30 min; purity (UV)=100%

Alkyl halide: 1-Bromo-2-butyne

Example 111

Compound III 2-(3,5-Dichloro-pyridin-4-yl)-1-[3,4-dimethoxy-2-(3-methyl-but-2-enyloxy)-phenyl]-ethanone LC/MS (METHOD B): (m/z) 410.1 (MH+); RT=4.83 min; purity (UV)=100%
Alkyl halide: 1-Bromo-2-methyl-2-butene

Example 112

Compound 112

2-(3,5-Dichloro-pyridin-4-yl)-1-(3,4-dimethoxy-2-phenethyloxy-phenyl)-ethanone $^1$H NMR (CDCl$_3$) δ=8.48 (2H, s), 7.61 (1H, d), 7.31-7.08 (5H, m), 6.75 (1H, d), 4.50-4.46 (4H, m), 3.92 (3H, s), 3.77 (3H, s), 3.18 (2H, t).
Alkyl halide: 1-Bromo-2-phenyl-ethane

Example 113

Compound 113

1-(2-Benzyloxy-3,4-dimethoxy-phenyl)-2-(3,5-dichloro-pyridin-4-yl)-ethanone

LC/MS (METHOD B): (m/z) 432.1 (MH+); RT=4.70 min; purity (UV)=100%
Alkyl halide: Benzyl bromide

Example 114

Compound 114

1-(2-Allyloxy-3,4-dimethoxy-phenyl)-2-(3,5-dichloro-pyridin-4-yl)-ethanone

LC/MS (METHOD B): (m/z) 382 (MH+); RT=4.34 min; purity (UV)=100%
Alkyl halide: Allyl bromide

Example 115

Compound 115

1-[2-(Benzooxazol-2-ylmethoxy)-3,4-dimethoxy-phenyl]-2-(3,5-dichloro-pyridin-4-yl)-ethanone LC/MS (METHOD B): (m/z) 473 (MH+); RT=4.36 min; purity (UV)=100%
Alkyl halide: 2-(chloromethyl)-1,3-benzoxazole

Example 116

Compound 116

2-(3,5-Dichloro-pyridin-4-yl)-1-[3,4-dimethoxy-2-(2-methyl-thiazol-4-ylmethoxy)-phenyl]-ethanone LC/MS (METHOD B): (m/z) 453 (MH+); RT=4.02 min; purity (UV)=100%
Alkyl halide: 4-(chloromethyl)-2-methylthiazole

Example 117

Compound 117

1-[2-(5-Cyclopropyl-[1,3,4]thiadiazol-2-ylmethoxy)-3,4-dimethoxy-phenyl]-2-(3,5-dichloro-pyridin-4-yl)-ethanone LC/MS (METHOD B): (m/z) 480.1 (MH+); RT=3.86 min; purity (UV)=100%
Alkyl halide: 2-(chloromethyl)-5-cyclopropyl-[1,3,4]thiadiazole

Example 118

Compound 118

2-(3,5-Dichloro-pyridin-4-yl)-1-[3,4-dimethoxy-2-([1,2,4]oxadiazol-3-ylmethoxy)-phenyl]-ethanone LC/MS (METHOD B): (m/z) 424 (MH+); RT=3.65 min; purity (UV)=100%
Alkyl halide: 3-(Chloromethyl)-[1,2,4]oxadiazole

Example 119

Compound 119

{6-[2-(3,5-Dichloro-pyridin-4-yl)-acetyl]-2,3-dimethoxy-phenoxy}-acetic acid ethyl ester $^1$H NMR (CDCl$_3$) δ=8.48 (2H, s), 7.61 (1H, d), 6.76 (1H, d), 4.92 (1H, s), 4.79 (2H, s), 4.25 (2H, q), 3.93 (3H, s), 3.88 (3H, s), 1.27 (3H, t).
Alkyl halide: Ethyl bromoacetate.

Example 120

Compound 120

1-{2-[2-(4-Chloro-phenyl)-ethoxy]-3,4-dimethoxy-phenyl}-2-(3,5-dichloro-pyridin-4-yl)-ethanone $^1$H NMR (CDCl$_3$) δ=8.49 (2H, s), 7.61 (1H, d), 7.23-7.18 (4H, m), 6.75 (1H, d), 4.45 (2H, t), 4.37 (2H, s), 3.93 (3H, s), 3.77 (3H, s), 3.14 (2H, t).
Alkyl halide: 4-Chlorobenzyl chloride

Example 121

Compound 121

1-[2-(5-Chloro-thiophen-2-ylmethoxy)-3,4-dimethoxy-phenyl]-2-(3,5-dichloro-pyridin-4-yl)-ethanone LC/MS (METHOD B): (m/z) 474 (MH+); RT=5.01 min; purity (UV)=100%
Alkyl halide: 5-Chloro-2-(chloromethyl)-thiophene

Example 122

Compound 122

2-(3,5-Dichloro-pyridin-4-yl)-1-[3,4-dimethoxy-2-(2-phenoxy-ethoxy)-phenyl]-ethanone $^1$H NMR (CDCl$_3$) δ=8.48 (2H, s), 7.65 (1H, d), 7.23 (2H, t), 6.92 (1H, t), 6.85 (2H, d), 6.76 (1H, d), 4.78 (2H, s), 4.69-4.63 (2H, m), 4.39-4.33 (2H, m), 3.94 (3H, s), 3.92 (3H, s).
Alkyl halide: 1-Bromo-2-phenoxy-ethane

Example 123

Compound 123

2-(3,5-Dichloro-pyridin-4-yl)-1-[3,4-dimethoxy-2-(2-p-tolyl-ethoxy)-phenyl]-ethanone LC/MS (METHOD B): (m/z) 460 (MH+); RT=5.29 min; purity (UV)=100%
Alkyl halide: 1-Bromo-2-(4-methylphenyl)-ethane

Example 124

Compound 124

2-(3,5-Dichloro-pyridin-4-yl)-1-[3,4-dimethoxy-2-(3-phenyl-propoxy)-phenyl]-ethanone $^1$H NMR (CDCl$_3$) δ=8.49 (2H, s), 7.59 (1H, d), 7.22 (5H, m), 6.75 (1H, d), 4.69 (2H, s), 4.28 (2H, t), 3.93 (3H, s), 3.88 (3H, s), 2.85 (2H, t), 2.21 (2H, m).
Alkyl halide: 1-Bromo-3-phenyl-propane

Example 125

Compound 125

2-(3,5-Dichloro-pyridin-4-yl)-1-{3,4-dimethoxy-2-[2-(3-methoxy-phenyl)-ethoxy]-phenyl}-ethanone LC/MS (METHOD B): (m/z) 476.2 (MH+); RT=4.86 min; purity (UV)=100%
Alkyl halide: 1-Bromo-2-(3-methoxyphenyl)-ethane

Example 126

Compound 126

2-(3,5-Dichloro-pyridin-4-yl)-1-{3,4-dimethoxy-2-[2-(4-methoxy-phenyl)-ethoxy]-phenyl}-ethanone LC/MS (METHOD B): (m/z) 476.2 (MH+); RT=4.84 min; purity (UV)=100%
Alkyl halide: 1-Bromo-2-(4-methoxyphenyl)-ethane

Example 127

Compound 127

1-{2-[2-(3-Bromo-phenyl)-ethoxy]-3,4-dimethoxy-phenyl}-2-(3,5-dichloro-pyridin-4-yl)-ethanone $^1$H NMR (DMSO-d$_6$) δ=8.62 (2H, s), 7.54 (2H, m), 7.26 (3H, m), 6.97 (1H, d), 4.43 (2H, t), 4.36 (2H, s), 3.88 (3H, s), 3.70 (3H, s), 3.14 (2H, t).
Alkyl halide: 1-Bromo-2-(3-bromophenyl)-ethane

Example 128

Compound 128

2-(3,5-Dichloro-pyridin-4-yl)-1-{3,4-dimethoxy-2-[2-(2-methoxy-phenyl)-ethoxy]-phenyl}-ethanone LC/MS (METHOD B): (m/z) 476.2 (MH+); RT=5.08 min; purity (UV)=100%
Alkyl halide: 1-Bromo-2-(2-methoxyphenyl)-ethane

Example 129

Compound 129

2-(3,5-Dichloro-pyridin-4-yl)-1-{2-[2-(4-fluoro-phenyl)-ethoxy]-3,4-dimethoxy-phenyl}-ethanone LC/MS (METHOD B): (m/z) 464.3 (MH+); RT=4.83 min; purity (UV)=100%
Alkyl halide: 1-Bromo-2-(4-fluorophenyl)-ethane

Example 130

Compound 130

2-(3,5-Dichloro-pyridin-4-yl)-1-{2-[2-(2-fluoro-phenyl)-ethoxy]-3,4-dimethoxy-phenyl}-ethanone LC/MS (METHOD B): (m/z) 464.2 (MH+); RT=4.99 min; purity (UV)=100%
Alkyl halide: 1-Bromo-2-(2-fluorophenyl)-ethane

Example 131

Compound 131

2-(3,5-Dichloro-pyridin-4-yl)-1-{2-[2-(3,4-dimethoxy-phenyl)-ethoxy]-3,4-dimethoxy-phenyl}-ethanone $^1$H NMR (DMSO-d$_5$) δ=8.60 (2H, s), 7.52 (1H, d), 6.95 (1H, d), 6.89 (1H, d), 6.81 (1H, d), 6.73 (1H, d), 4.43 (2H, t), 4.26 (2H, s), 3.88 (3H, s), 3.76 (3H, s), 3.68 (3H, s), 3.55 (3H, s), 3.06 (2H, t).
Alkyl halide: 1-Bromo-2-(3,4-dimethoxyphenyl)-ethane

Example 132

Compound 132

{6-[2-(3,5-Dichloro-pyridin-4-yl)-acetyl]-2,3-dimethoxy-phenoxy}-acetic acid benzyl ester LC/MS (METHOD B): (m/z) 490.2 (MH+); RT=4.66 min; purity (UV)=100%
Alkyl halide: Benzyl bromoacetate

Example 133

Compound 133

{6-[2-(3,5-Dichloro-pyridin-4-yl)-acetyl]-2,3-dimethoxy-phenoxy}-acetic acid isopropyl ester LC/MS (METHOD B): (m/z) 442.2 (MH+); RT=4.44 min; purity (UV)=100%
Alkyl halide: Isopropyl bromoacetate

Example 1.34

Compound 134)

3-{6-[2-(3,5-Dichloro-pyridin-4-yl)-acetyl]-2,3-dimethoxy-phenoxymethyl}-benzoic acid methyl ester LC/MS (METHOD A): (m/z) 489.9 (MH+); RT=8.14 min; purity (UV)=100%
Alkyl halide: 3-Chloromethyl benzoic acid methyl ester

Example 135

Compound 135

2-(3,5-Dichloro-pyridin-4-yl)-1-[3,4-dimethoxy-2-(3-methyl-butoxy)-phenyl]-ethanone LC/MS (METHOD A): (m/z) 412 (MH+); RT=8.99 min; purity (UV)=100%

Alkyl halide: 1-Bromo-3-methyl-butan

Example 136

Compound 136

2-(3,5-Dichloro-pyridin-4-yl)-1-(2-hexyloxy-3,4-dimethoxy-phenyl)-ethanone

LC/MS (METHOD A): (m/z) 395.9 (MH+); RT=9.42 min; purity (UV)=100%
Alkyl halide: 1-Bromo-hexan

Example 137

Compound 137

1-(2-But-3-enyloxy-3,4-dimethoxy-phenyl)-2-(3,5-dichloro-pyridin-4-yl)-ethanone LC/MS (METHOD A): (m/z) 395.9 (MH+); RT=8.27 min; purity (UV)=100%
Alkyl halide: 4-Bromo-but-1-ene

Example 138

Compound 138

2-(3,5-Dichloro-pyridin-4-yl)-1-(3,4-dimethoxy-2-pent-4-enyloxy-phenyl)-ethanone LC/MS (METHOD A): (m/z) 410 (MH+); RT=8.62 min; purity (UV)=100%

Alkyl halide: 5-Bromo-pent-1-ene

Example 139

Compound 139

2-(3,5-Dichloro-pyridin-4-yl)-1-(3,4-dimethoxy-2-propoxy-phenyl)-ethanone

LC/MS (METHOD A): (m/z) 383.9 (MH+); RT=8.34 min; purity (UV)=100%
Alkyl halide: 1-Iodo-propan

Example 140

Compound 140

1-(2-Butoxy-3,4-dimethoxy-phenyl)-2-(3,5-dichloro-pyridin-4-yl)-ethanone

LC/MS (METHOD A): (m/z) 397.9 (MH+); RT=8.72 min; purity (UV)=100%
Alkyl halide: 1-Iodo-butan

Example 141

Compound 141

2-(3,5-Dichloro-pyridin-4-yl)-1-(2-isobutoxy-3,4-dimethoxy-phenyl)-ethanone

LC/MS (METHOD A): (m/z) 397.9 (MH+); RT=8.72 min; purity (UV)=100%
Alkyl halide: 1-Iodo-2-methyl-propane

Example 142

Compound 142

4-{6-[2-(3,5-Dichloro-pyridin-4-yl)-acetyl]-2,3-dimethoxy-phenoxy}-butyric acid ethyl ester LC/MS (METHOD A): (m/z) 456 (MH+); RT=7.89 min; purity (UV)=100%
Alkyl halide: 4-Bromo-butyric acid ethyl ester

Example 143

Compound 143

2-(3,5-Dichloro-pyridin-4-yl)-1-[3,4-dimethoxy-2-(4-methyl-benzyloxy)-phenyl]-ethanone LC/MS (METHOD A): (m/z) 445.9 (MH+); RT=8.69 min; purity (UV)=97.1%
Alkyl halide: 4-Methyl-benzylchloride

Example 144

Compound 144

1-[2-(3-Chloro-benzyloxy)-3,4-dimethoxy-phenyl]-2-(3,5-dichloro-pyridin-4-yl)-ethanone LC/MS (METHOD A): (m/z) 465.9 (MH+); RT=8.69 min; purity (UV)=100%
Alkyl halide: 3-Chloro-benzylchloride

Example 145

Compound 145

2-(3,5-Dichloro-pyridin-4-yl)-1-[3,4-dimethoxy-2-(3-phenoxy-propoxy)-phenyl]-ethanone LC/MS (METHOD A): (m/z) 476 (MH+); RT=8.59 min; purity (UV)=98.2%
Alkyl halide: (3-Bromo-propoxy)-benzene

Example 146

Compound 146

2-(3,5-Dichloro-pyridin-4-yl)-1-{3,4-dimethoxy-2-[2-(4-methoxy-phenyl)-2-oxo-ethoxy]-phenyl}-ethanone LC/MS (METHOD A): (m/z) 490 (MH+); RT=7.74 min; purity (UV)=97.1%
Alkyl halide: 2-Bromo-1-(4-methoxy-phenyl)-ethanone

Example 147

Compound 147

2-{6-[2-(3,5-Dichloro-pyridin-4-yl)-acetyl]-2,3-dimethoxy-phenoxymethyl}-benzonitrile LC/MS (METHOD A): (m/z) 456.9 (MH+); RT=7.81 min; purity (UV)=97.1%. $^1$H NMR (DMSO-$d_6$) δ=8.60 (2H, s), 7.91 (1H, d), 7.81 (1H, d), 7.78 (1H, t), 7.59 (1H, t), 7.55 (1H, d), 7.02 (1H, d), 5.43 (2H, s), 4.50 (2H, s), 3.92 (3H, s), 3.81 (3H, s).
Alkyl halide: 2-Chloromethyl-benzonitrile

Example 148

Compound 148

4-{6-[2-(3,5-Dichloro-pyridin-4-yl)-acetyl]-2,3-dimethoxy-phenoxymethyl}-benzonitrile LC/MS (METHOD A): (m/z) 456.9 (MH+); RT=7.82 min; purity (UV)=98.5%
Alkyl halide: 4-Chloromethyl-benzonitrile

Example 149

Compound 149

2-(3,5-Dichloro-pyridin-4-yl)-1-[3,4-dimethoxy-2-(naphthalen-2-ylmethoxy)-phenyl]-ethanone LC/MS (METHOD A): (m/z) 481.9 (MH+); RT=8.86 min; purity (UV)=77.3%
Alkyl halide: 2-Bromomethyl-naphthalene

Example 150

Compound 150

2-(3,5-Dichloro-pyridin-4-yl)-1-(3,4-dimethoxy-2-pentyloxy-phenyl)-ethanone

LC/MS (METHOD A): (m/z) 411.9 (MH+); RT=9.06 min; purity (UV)=100%
Alkyl halide: 1-Iodo-pentane

Example 151

Compound 151

1-(2-Cyclohexylmethoxy-3,4-dimethoxy-phenyl)-2-(3,5-dichloro-pyridin-4-yl)-ethanone LC/MS (METHOD A): (m/z) 438 (MH+); RT=9.59 min; purity (UV)=100%
Alkyl halide: Bromomethyl-cyclohexane

Example 152

Compound 152

3-(6-[2-(3,5-Dichloro-pyridin-4-yl)-acetyl]-2,3-dimethoxy-phenoxymethyl)-benzonitrile LC/MS (METHOD A): (m/z) 456.9 (MH+); RT=7.81 min; purity (UV)=96.5%
Alkyl halide: 3-Chloromethyl-benzonitrile

Example 153

Compound 153

1-{2-[2-(4-Chloro-phenoxy)-ethoxy]-3,4-dimethoxy-phenyl}-2-(3,5-dichloro-pyridin-4-yl)-ethanone LC/MS (METHOD A): (m/z) 495.9 (MH+); RT=8.56 min; purity (UV)=100% Alkyl halide; 1-(2-Bromo-ethoxy)-4-chloro-benzene

Example 154

Compound 154

2-(3,5-Dichloro-pyridin-4-yl)-1-[2-(2-ethyl-butoxy)-3,4-dimethoxy-phenyl]-ethanone LC/MS (METHOD A): (m/z) 426 (MH+); RT=9.39 min; purity (UV)=92.5%
Alkyl halide: 1-Iodo-2-ethyl-butane

Example 155

Compound 155

2-(3,5-Dichloro-pyridin-4-yl)-1-[2-(2-hydroxy-ethoxy)-3,4-dimethoxy-phenyl]-ethanone LC/MS (METHOD A): (m/z) 385.9 (MH+); RT=6.22 min; purity (UV)=88.0%
Alkyl halide: 1-Iodo-2-hydroxy-ethane

Example 156

Compound 156

4-{6-[2-(3,5-Dichloro-pyridin-4-yl)-acetyl]-2,3-dimethoxy-phenoxymethyl}-benzoic acid methyl ester LC/MS (METHOD A): (m/z) 489.9 (MH+); RT=8.17 min; purity (UV)=89.6%
Alkyl halide: 4-Chloromethyl benzoic acid methyl ester

Example 157

Compound 157

2-(3,5-Dichloro-pyridin-4-yl)-1-[3,4-dimethoxy-2-(2-naphthalen-2-yl-2-oxo-ethoxy)-phenyl]-ethanone LC/MS (METHOD A): (m/z) 509.9 (MH+); RT=8.41 min; purity (UV)=89.9%
Alkyl halide: 2-Bromo-1-naphthalen-2-yl-ethanone

Example 158

Compound 158

2-(3,5-Dichloro-pyridin-4-yl)-1-(2-[2-(2,5-dimethoxy-phenyl)-2-oxo-ethoxy]-3,4-dimethoxy-phenyl)-ethanone LC/MS (METHOD A): (m/z) 519.9 (MH+); RT=7.99 min; purity (UV)=95.7%
Alkyl halide: 2-Bromo-2,5-dimethoxy-phenyl-ethanone

Example 159

Compound 159

2-(3,5-Dichloro-pyridin-4-yl)-1-[3,4-dimethoxy-2-(2-oxo-2-p-tolyl-ethoxy)-phenyl]-ethanone LC/MS (METHOD A): (m/z) 473.9 (MH+); RT=8.11 min; purity (UV)=88.1%
Alkyl halide: 2-Bromo-1-p-tolyl-ethanone

Example 160

Compound 160

2-(3,5-Dichloro-pyridin-4-yl)-1-[2-(4-fluoro-benzyloxy)-3,4-dimethoxy-phenyl]-ethanone LC/MS (METHOD A): (m/z) 449.9 (MH+); RT=8.32 min; purity (UV)=100%
Alkyl halide: 4-Fluoro-benzylchloride

Example 161

Compound 161

2-(3,5-Dichloro-pyridin-4-yl)-1-[2-(2-fluoro-benzyloxy)-3,4-dimethoxy-phenyl]-ethanone LC/MS (METHOD A): (m/z) 449.9 (MH+); RT=8.34 min; purity (UV)=95.7%
Alkyl halide: 2-Fluoro-benzylchloride

Example 162

Compound 162

2-(3,5-Dichloro-pyridin-4-yl)-1-[3,4-dimethoxy-2-(3-trifluoromethyl-benzyloxy)-phenyl]-ethanone LC/MS (METHOD A): (m/z) 499.9 (MH+); RT=8.61 min; purity (UV)=98.9%
Alkyl halide: 5-Trifluoromethyl-benzylchloride

Example 163

Compound 163

2-(3,5-Dichloro-pyridin-4-yl)-1-[3,4-dimethoxy-2-(3-trifluoromethoxy-benzyloxy)-phenyl]-ethanone LC/MS (METHOD A): (m/z) 515.9 (MH+); RT=8.72 min; purity (UV)=98.9%
Alkyl halide: 5-Trifluoromethoxy-benzylchloride

Example 164

Compound 164

2-(3,5-Dichloro-pyridin-4-yl)-1-[2-(3-fluoro-5-trifluoromethyl-benzyloxy)-3,4-dimethoxy-phenyl]-ethanone LC/MS (METHOD A): (m/z) 558.9 (MH+); RT=8.71 min; purity (UV)=98.9%
Alkyl halide: 3-Fluoro-5-trifluoromethyl-benzylchloride

Example 165

Compound 165

2-(3,5-Dichloro-pyridin-4-yl)-1-{3,4-dimethoxy-2-[2-(2-methoxy-phenyl)-2-oxo-ethoxy]-phenyl}-ethanone LC/MS (METHOD A): (m/z) 490 (MH+); RT=7.96 min; purity (UV)=95.8%
Alkyl halide: 2-Bromo-1-(2-methoxy-phenyl)-ethanone

Example 166

Compound 166

2-(3,5-Dichloro-pyridin-4-yl)-1-{2-[2-(2,4-dimethyl-phenyl)-2-oxo-ethoxy]-3,4-dimethoxy-phenyl}-ethanone LC/MS (METHOD A): (m/z) 487.9 (MH+); RT=8.49 min; purity (UV)=99.1%
Alkyl halide: 2-Bromo-1-(2,4-dimethyl-phenyl)-ethanone

Example 167

Compound 167

1-[2-(4-Chloro-benzyloxy)-3,4-dimethoxy-phenyl]-2-(3,5-dichloro-pyridin-4-yl)-ethanone LC/MS (METHOD A): (m/z) 465.9 (MH+); RT=8.72 min; purity (UV)=98.5%
Alkyl halide: 4-Chloro-benzylchloride

Example 168

Compound 168

2-(3,5-Dichloro-pyridin-4-yl)-1-[2-(2-difluoromethoxy-benzyloxy)-3,4-dimethoxy-phenyl]-ethanone LC/MS (METHOD A): (m/z) 497.8 (MH+); RT=8.19 min; purity (UV)=98.5%
Alkyl halide: 2-Difluoromethoxy-benzylchloride

Example 169

Compound 169

2-(3,5-Dichloro-pyridin-4-yl)-1-[2-(4-isopropyl-benzyloxy)-3,4-dimethoxy-phenyl]-ethanone LC/MS (METHOD A): (m/z) 474 (MH+); RT=9.21 min; purity (UV)=100%
Alkyl halide: 4-Isopropyl-benzylchloride

Example 170

Compound 170

2-(3,5-Dichloro-pyridin-4-yl)-1-[2-(2-fluoro-6-trifluoromethyl-benzyloxy)-3,4-dimethoxy-phenyl]-ethanone LC/MS (METHOD A): (m/z) 517.9 (MH+); RT=8.52 min; purity (UV)=98.9%
Alkyl halide: 2-Fluoro-6-trifluoromethyl-benzylchloride

Example 171

Compound 171

2-(3,5-Dichloro-pyridin-4-yl)-1-[2-(2,3-difluoro-4-methyl-benzyloxy)-3,4-dimethoxy-phenyl]-ethanone LC/MS (METHOD A): (m/z) 481.9 (MH+); RT=8.71 min; purity (UV)=98.6%
Alkyl halide: 2,3-Difluoro-4-methyl-benzylchloride

Example 172

Compound 172

2-(3,5-Dichloro-pyridin-4-yl)-1-[3,4-dimethoxy-2-(2-methyl-benzyloxy)-phenyl]-ethanone LC/MS (METHOD A): (m/z) 445.9 (MH+); RT=8.67 min; purity (UV)=98.5%
Alkyl halide: 2-Methyl-benzylchloride

Example 173

Compound 173

2-(3,5-Dichloro-pyridin-4-yl)-1-[3,4-dimethoxy-2-(3-methyl-benzyloxy)-phenyl]-ethanone LC/MS (METHOD A): (m/z) 446 (MH+); RT=8.69 min; purity (UV)=98.4%
Alkyl halide: 3-Methyl-benzylchloride

Example 174

Compound 174

2-(3,5-Dichloro-pyridin-4-yl)-1-(3,4-dimethoxy-2-pent-2-enyloxy-phenyl)-ethanone LC/MS (METHOD A): (m/z) 409.9 (MH+); RT=8.67 min; purity (UV)=98.3%
Alkyl halide: 1-Bromo-pent-2-ene

Example 175

Compound 175

2-(3,5-Dichloro-pyridin-4-yl)-1-[3,4-dimethoxy-2-(2-methyl-quinolin-6-ylmethoxy)-phenyl]-ethanone LC/MS (METHOD A): (m/z) 497 (MH+); RT=5.27 min; purity (UV)=98.1%
Alkyl halide: 6-Bromomethyl-2-methyl-quinoline

Example 176

Compound 176

1-[2-(2-Chloro-benzyloxy)-3,4-dimethoxy-phenyl]-2-(3,5-dichloro-pyridin-4-yl)-ethanone LC/MS (METHOD A): (m/z) 465.9 (MH+); RT=8.71 min; purity (UV)=96.3%
Alkyl halide: 2-Chloro-benzylchloride

Example 177

Compound 177

2-(3,5-Dichloro-pyridin-4-yl)-1-[3,4-dimethoxy-2-(3-methoxy-benzyloxy)-phenyl]-ethanone LC/MS (METHOD A): (m/z) 461.9 (MH+); RT=8.26 min; purity (UV)=96.3%
Alkyl halide: 3-Methoxy-benzylchloride

Example 178

Compound 178

2-(3,5-Dichloro-pyridin-4-yl)-1-[3,4-dimethoxy-2-(4-methoxy-benzyloxy)-phenyl]-ethanone LC/MS (METHOD A): (m/z) 461.9 (MH+); RT=8.22 min; purity (UV)=77.9%
Alkyl halide: 4-Methoxy-benzylchloride

Example 179

Compound 179

1-{2-[2-(3-Chloro-phenyl)-ethoxy]-3,4-dimethoxy-phenyl}-2-(3,5-dichloro-pyridin-4-yl)-ethanone LC/MS (METHOD A): (m/z) 479.9 (MH+); RT=8.81 min; purity (UV)=98.6%
Alkyl halide: 1-Bromo-2-(3-Chloro-phenyl)-ethane

Example 180

Compound 180

2-(3,5-Dichloro-pyridin-4-yl)-1-[3,4-dimethoxy-2-(5-methyl-hexyloxy)-phenyl]-ethanone LC/MS (METHOD A): (m/z) 440 (MH+); RT=9.69 min; purity (UV)=100%
Alkyl halide: 1-Bromo-5-methyl-hexane

Example 181

Compound 181

1-[2-(2-Cyclohexyl-ethoxy)-3,4-dimethoxy-phenyl]-2-(3,5-dichloro-pyridin-4-yl)-ethanone LC/MS (METHOD A): (m/z) 452 (MH+); RT=9.92 min; purity (UV)=97.7%
Alkyl halide: (2-Bromo-ethyl)-cyclohexane

Example 182

Compound 182

5-{6-[2-(3,5-Dichloro-pyridin-4-yl)-acetyl]-2,3-dimethoxy-phenoxy}-pentanoic acid ethyl ester LC/MS (METHOD A): (m/z) 470 (MH+); RT=8.11 min; purity (UV)=100%
Alkyl halide: 4-Bromo-pentanoic acid ethyl ester

Example 183

Compound 183

1-[2-(3-Benzyloxy-propoxy)-3,4-dimethoxy-phenyl]-2-(3,5-dichloro-pyridin-4-yl)-ethanone LC/MS (METHOD A): (m/z) 490 (MH+); RT=8.64 min; purity (UV)=97.5%
Alkyl halide: (3-Bromo-propoxymethyl)-benzene

Example 184

Compound 184

2-{6-[2-(3,5-Dichloro-pyridin-4-yl)-acetyl]-2,3-dimethoxy-phenoxy}-acetamide $^1$H NMR (DMSO-$d_6$) δ=8.64 (2H, s), 7.67-7.58 (2H, m), 7.37 (1H, bs), 6.98 (1H, d), 4.79 (2H, s), 4.62 (2H, s), 3.90 (3H, s), 3.80 (3H, s).
Alkyl halide: 2-Chloro-acetamide

Example 185

Compound 185

2-(2-{6-[2-(3,5-Dichloro-pyridin-4-yl)-acetyl]-2,3-dimethoxy-phenoxy}-ethyl)-isoindole-1,3-dione $^1$H NMR (CDCl$_3$) δ=8.36 (2H, s), 7.74 (2H, m), 7.60 (3H, m), 6.75 (1H, d), 4.52 (2H, t), 4.48 (2H, s), 4.21 (2H, t), 3.91 (3H, s), 3.83 (3H, s).
Alkyl halide: 2-(2-Bromo-ethyl)-isoindole-1,3-dione

Example 186

Compound 186

2-(3-{6-[2-(3,5-Dichloro-pyridin-4-yl)-acetyl]-2,3-dimethoxy-phenoxy}-propyl)-isoindole-1,3-dione $^1$H NMR (CDCl$_3$) δ=8.48 (2H, s), 7.81 (2H, m), 7.70 (2H, m), 7.59 (1H, d), 6.75 (1H, d), 4.67 (2H, s), 4.31 (2H, t), 3.96 (2H, t), 3.93 (3H, s), 3.89 (3H, s), 2.30 (2H, m).
Alkyl halide: 2-(3-Bromo-propyl)-isoindole-1,3-dione

Example 187

Compound 187

2-{6-[2-(3,5-Dichloro-pyridin-4-yl)-acetyl]-2,3-dimethoxy-phenoxy}-N-methyl-acetamide
$^1$H NMR (CDCl$_3$) δ=8.52 (2H, s), 7.75-7.64 (2H, m), 6.79 (1H, d), 4.67 (2H, s), 4.60 (2H, s), 3.96 (3H, s), 3.87 (3H, s), 2.86 (3H, d).
Alkyl halide: 2-Chloro-N-methyl-acetamide

Example 305

Compound 305

2-{6-[2-(3,5-Dichloro-pyridin-4-yl)-acetyl]-2,3-dimethoxy-phenoxy}-N-ethyl-acetamide $^1$H NMR (DMSO-$d_5$) δ=8.64 (2H, s), 8.18 (1H, bs), 7.61 (1H, d), 6.99 (1H, d), 4.77 (2H, s), 4.62 (2H, s), 3.91 (3H, s), 3.79 (3H, s), 3.15 (2H, m), 1.01 (3H, t).
Alkyl halide: 2-Chloro-N-ethyl-acetamide
General Procedure for Preparation of Compounds with Formula Ii or Ij, Wherein R2 is as Defined Above:

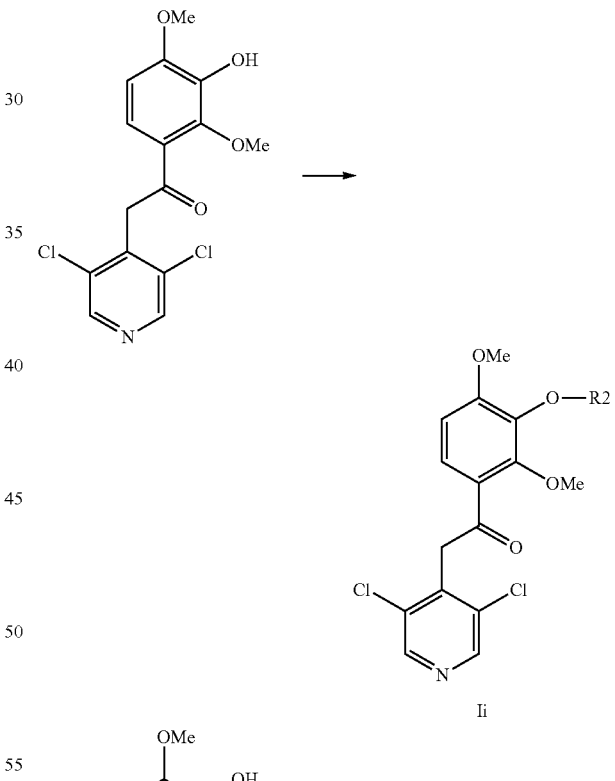

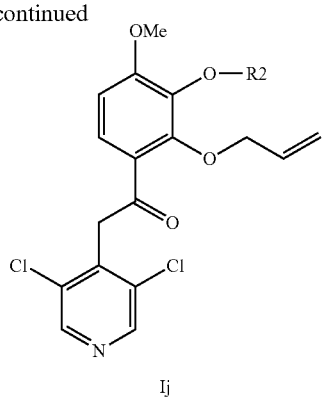

2-(3,5-Dichloro-pyridin-4-yl)-1-(3-hydroxy-2,4-methoxy-phenyl)-ethanone (0.035 mmol) from example 2 (Ii) or 1-(2-allyloxy-3-hydroxy-4-methoxy-phenyl)-2-(3,5-dichloro-pyridin-4-yl)-ethanone (0.035 mmol) from example 3 (Ij) was dissolved in dry 3-pentanone (0.4 mL). Solid K$_2$CO$_3$ (0.052 mmol) was added followed by 0.052 mmol of an alkyl bromide or iodide dissolved in 3-pentanone (0.1 mL). In the case of the alkyl bromides additional KI (0.5 eq) was added. The reaction mixture was heated to 70° C. for 18 hours. The samples were filtered in the solvent removed in vacuo. The pure compounds were obtained by redissolving the reaction mixture in DMSO followed by standard preparative HPLC purification.

Using this procedure the following compounds were obtained:

Example 188

Compound 188

2-(3,5-Dichloro-pyridin-4-yl)-1-(3-ethoxy-2,4-dimethoxy-phenyl)-ethanone

LC/MS (METHOD B): (m/z) 370 (MH+); RT=4.45 min; purity (UV)=100%

Alkyl halide: Iodoethane

Example 189

Compound 18.)

1-(3-Cyclopropylmethoxy-2,4-dimethoxy-phenyl)-2-(3,5-dichloro-pyridin-4-yl)-ethanone LC/MS (METHOD B): (m/z) 396.1 (MH+); RT=4.78 min; purity (UV)=100%

Alkyl halide: Bromomethyl-cyclopropane

Example 190

Compound 190

1-(2-Allyloxy-3-but-3-enyloxy-4-methoxy-phenyl)-2-(3,5-dichloro-pyridin-4-yl)-ethanone LC/MS (METHOD B: (m/z) 422.1 (MH+); RT=5.27 min; purity (UV)=100%

Alkyl halide: 4-Bromo-but-1-ene

Example 191

Compound 191

1-(3-But-3-enyloxy-2,4-dimethoxy-phenyl)-2-(3,5-dichloro-pyridin-4-yl)-ethanone LC/MS (METHOD A): (m/z) 396.3 (MH+); RT=8.39 min; purity (UV)=94.0%

Alkyl halide: 4-Bromo-but-1-ene

Example 192

Compound 192

2-(3,5-Dichloro-pyridin-4-yl)-1-(2,4-dimethoxy-3-propoxy-phenyl)-ethanone

LC/MS (METHOD A): (m/z) 384.3 (MH+); RT=8.42 min; purity (UV)=100%

Alkyl halide: 1-Iodoethane

Example 193

Compound 193

1-(3-Allyloxy-2,4-dimethoxy-phenyl)-2-(3,5-dichloro-pyridin-4-yl)-ethanone

LC/MS (METHOD A): (m/z) 382.3 (MH+); RT=8.01 min; purity (UV)=100%

Alkyl halide: Allyl bromide

Example 194

Compound 194

2-(3,5-Dichloro-pyridin-4-yl)-1-[2,4-dimethoxy-3-(4-methyl-pent-3-enyloxy)-phenyl]-ethanone LC/MS (METHOD A): (m/z) 424.3 (MH+); RT=8.99 min; purity (UV)=100%

Alkyl halide: 5-Bromo-2-methyl-pent-2-ene

Example 195

Compound 195

2-(3,5-Dichloro-pyridin-4-yl)-1-[3-(2-hydroxy-ethoxy)-2,4-dimethoxy-phenyl]-ethanone LC/MS (METHOD A): (m/z) 386.3 (MH+); RT=6.21 min; purity (UV)=70.5%

Alkyl halide: 2-Indo-ethanol

Example 196

Compound 196

2-(3,5-Dichloro-pyridin-4-yl)-1-(2,4-dimethoxy-3-phenethyloxy-phenyl)-ethanone LC/MS (METHOD A): (m/z) 446.2 (MH+); RT=8.71 min; purity (UV)=82.0%

Alkyl halide: 2-Phenyl-1-bromo-ethane

Example 197

Compound 197

1-(3-Benzyloxy-2,4-dimethoxy-phenyl)-2-(3,5-dichloro-pyridin-4-yl)-ethanone

LC/MS (METHOD A): (m/z) 432.2 (MH+); RT=8.49 min; purity (UV)=96.3%

Alkyl halide: Benzyl bromide

Example 198

Compound 198

2-(3,5-Dichloro-pyridin-4-yl)-1-(2,4-dimethoxy-3-pent-2-enyloxy-phenyl)-ethanone LC/MS (METHOD A): (m/z) 410.3 (MH+); RT=8.67 min; purity (UV)=91.9%

Alkyl halide: 1-Bromo-pent-2-ene

Example 199

Compound 199

2-(3,5-Dichloro-pyridin-4-yl)-1-[2,4-dimethoxy-3-(2-methoxy-ethoxy)-phenyl]-ethanone LC/MS (METHOD A): (m/z) 400.3 (MH+); RT=7.34 min; purity (UV)=91.6%

Alkyl halide: 1-Bromo-2-methoxy-ethane

Example 200

Compound 200

1-(3-But-2-ynyloxy-2,4-dimethoxy-phenyl)-2-(3,5-dichloro-pyridin-4-yl)-ethanone LC/MS (METHOD A): (m/z) 394.3 (MH+); RT=7.81 min; purity (UV)=100%

Alkyl halide: 1-Bromo-but-2-yne

Example 201

Compound 201

2-(3,5-Dichloro-pyridin-4-yl)-1-(2,4-dimethoxy-3-prop-2-ynyloxy-phenyl)-ethanone LC/MS (METHOD A): (m/z) 380.2 (MH+); RT=7.44 min; purity (UV)=100%

Alkyl halide: 3-Bromo-propyne

Preparation 4

Example 273

Compound 504

{6-[2-(3,5-Dichloro-pyridin-4-yl)-acetyl]-2,3-dimethoxy-phenoxy}-acetic acid

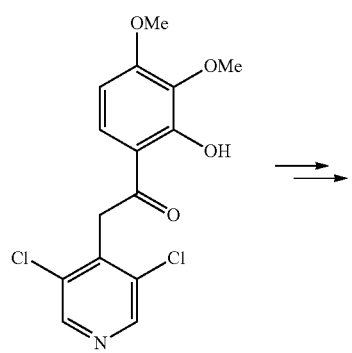

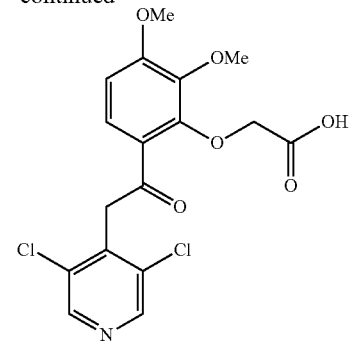

2-(3,5-Dichloro-pyridin-4-yl)-1-(2-hydroxy-3,4-methoxy-phenyl)-ethanone (1.37 g, 4.1 mmol) from example 1 was dissolved in dry NMP (50 mL). Ethyl bromoacetate (660 μL, 6.1 mmol) was added followed by K₂CO₃ (830 mg, 6.1 mmol) and the reaction mixture was stirred at rt overnight. Water (500 mL) was added and the product extracted with EtOAc (2×250 mL). The combined organic phases were washed with water (250 mL), brine (250 mL) and dried over MgSO₄. The solvent were removed in vacuo and the pure product obtained be standard silica gel chromatography to provide {6-[2-(3,5-Dichloro-pyridin-4-yl)-acetyl]-2,3-dimethoxy-phenoxy}-acetic acid ethyl ester as a white solid. Yield 990 mg (78%). The compound was re-dissolved in MeOH-water (1:1, 200 mL) by heating. LiOH (490 mg, 12 mmol, 5 eq.) was added and the reaction mixture was stirred at rt for 1 hour. The reaction mixture was acidified to pH=1 by addition of 1N HCl (15 mL) and extracted with EtOAc (2×250 mL). The combined organic phases were washed with brine (250 ml) and dried over MgSO₄. The solvent was removed in vacuo to provide {6-[2-(3,5-Dichloro-pyridin-4-yl)-acetyl]-2,3-dimethoxy-phenoxy}-acetic acid as a white solid. $^1$H NMR (CDCl₃) δ=8.52 (2H, s), 7.76 (1H, d), 6.81 (1H, d), 4.85 (2H, s), 4.66 (2H, s), 3.99 (3H, s), 3.88 (3H, s). Yield 0.85 g (92%).

General Procedure for Preparation of Compounds with Formula Ik, Wherein R9 and R12 are as Defined Herein:

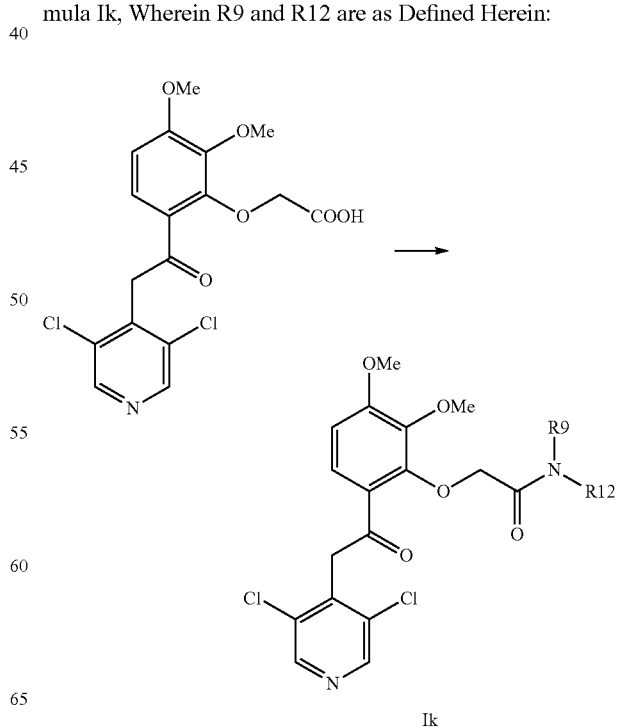

{6-[2-(3,5-Dichloro-pyridin-4-yl)-acetyl]-2,3-dimethoxy-phenoxy}-acetic acid (0.037 mmol) from preparation 4 was dissolved in dry DMF (0.25 mL). A primary or secondary amine (0.045 mmol) dissolved in DMF (0.05 mL) was added followed by HATU (0.045 mmol) dissolved in DMF (0.050 mL). The reaction mixture was left at rt for 48 hours. The pure compounds were obtained by standard preparative HPLC purification.

Using this procedure the following compounds were obtained:

Example 202

Compound 202

2-(3,5-Dichloro-pyridin-4-yl)-1-[3,4-dimethoxy-2-(2-oxo-2-pyrrolidin-1-yl-ethoxy)-phenyl]-ethanone $^1$H NMR (CDCl$_3$) δ=8.47 (2H, s), 7.64 (1H, d), 6.76 (1H, d), 4.92 (2H, s), 4.88 (2H, s), 3.94 (3H, s), 3.89 (3H, s), 3.53 (2H, t), 3.39 (2H, t), 1.98 (2H, m), 1.86 (2H, m).
Amine: Pyrrolidine

Example 203

Compound 203

N-Benzyl-2-{6-[2-(3,5-dichloro-pyridin-4-yl)-acetyl]-2,3-dimethoxy-phenoxy}-acetamide $^1$H NMR (CDCl$_3$) δ=8.49 (2H, s), 8.12 (1H, bs), 7.66 (1H, d), 7.29-7.20 (5H, m), 6.77 (1H, d), 4.72 (2H, s), 4.55 (2H, s), 4.50 (2H, d), 3.95 (3H, s), 3.81 (3H, s).
Amine: Benzylamine

Example 204

Compound 204

2-(3,5-Dichloro-pyridin-4-yl)-1-[3,4-dimethoxy-2-(2-morpholin-4-yl-2-oxo-ethoxy)-phenyl]-ethanone $^1$H NMR (CDCl$_3$) δ=8.48 (2H, s), 7.63 (1H, d), 6.78 (1H, d), 4.96 (2H, s), 4.80 (2H, s), 3.94 (3H, s), 3.89 (3H, s), 3.72-3.61 (6H, m), 3.54-3.45 (2H, m).
Amine: Morpholine

Example 205

Compound 205

2-{6-[2-(3,5-Dichloro-pyridin-4-yl)-acetyl]-2,3-dimethoxy-phenoxy}-N-phenyl-acetamide $^1$H NMR (CDCl$_3$) δ=9.97 (1H, bs), 8.50 (2H, s), 7.75 (1H, d), 7.59 (2H, d), 7.25 (2H, t), 7.07 (1H, t), 6.81 (1H, d), 4.80 (2H, s), 4.65 (2H, s), 3.99 (3H, s), 3.89 (3H, s).
Amine: Aniline

Example 206

Compound 206

2-{6-[2-(3,5-Dichloro-pyridin-4-yl)-acetyl]-2,3-dimethoxy-phenoxy}-N-methyl-N-phenyl-acetamide $^1$H NMR (CDCl$_3$) δ=8.48 (2H, s), 7.59 (1H, d), 7.45-7.32 (3H, m), 7.25-7.19 (2H, m), 6.70 (1H, d), 4.83 (2H, s), 4.68 (2H, s), 3.90 (3H, s), 3.77 (3H, s), 3.32 (3H, s).
Amine: N-Methyl aniline

Example 207

Compound 207

2-{6-[2-(3,5-Dichloro-pyridin-4-yl)-acetyl]-2,3-dimethoxy-phenoxy}-N-(3-hydroxy-3-methyl-butyl)-acetamide LC/MS (METHOD A): (m/z) 485 (MH+); RT=5.89 min; purity (UV)=100%
Amine: 3-Hydroxy-3-methyl-butylamine

Example 208

Compound 208

2-{6-[2-(3,5-Dichloro-pyridin-4-yl)-acetyl]-2,3-dimethoxy-phenoxy}-N-propyl-acetamide LC/MS (METHOD A): (m/z) 441 (MH+); RT=6.71 min; purity (UV)=89.3%
$^1$H NMR (CDCl$_3$) δ=8.51 (2H, s), 7.79 (1H, bs), 7.67 (1H, d), 6.78 (1H, d), 4.67 (2H, s), 4.60 (2H, s), 3.97 (3H, s), 3.87 (3H, s), 3.27 (2H, q), 1.50 (2H, m), 0.87 (3H, t).
Amine: n-Propylamine

Example 209

Compound 209

2-{6-[2-(3,5-Dichloro-pyridin-4-yl)-acetyl]-2,3-dimethoxy-phenoxy}-N-isopropyl-acetamide LC/MS (METHOD A): (m/z) 441 (MH+); RT=6.72 min; purity (UV)=87.7%
$^1$H NMR (DMSO-d$_5$) δ=8.64 (2H, s), 8.01 (1H, d), 7.65 (1H, d), 6.99 (1H, d), 4.77 (2H, s), 4.61 (2H, s), 3.91 (4H, m), 3.80 (3H, s), 1.04 (6H, d)
Amine: Isopropylamine

Example 210

Compound 210

N-Butyl-2-{6-[2-(3,5-dichloro-pyridin-4-yl)-acetyl]-2,3-dimethoxy-phenoxy}-acetamide LC/MS (METHOD A): (m/z) 455 (MH+); RT=7.09 min; purity (UV)=100%
Amine: Butylamine

Example 211

Compound 211

N-Cyclopentyl-2-{6-[2-(3,5-dichloro-pyridin-4-yl)-acetyl]-2,3-dimethoxy-phenoxy}-acetamide LC/MS (METHOD A): (m/z) 466.9 (MH+); RT=7.19 min; purity (UV)=100%
Amine: Cyclopentylamine

Example 212

Compound 212

2-{6-[2-(3,5-Dichloro-pyridin-4-yl)-acetyl]-2,3-dimethoxy-phenoxy}-N-(3-methyl-butyl)-acetamide LC/MS (METHOD A): (m/z) 469 (MH+); RT=7.42 min; purity (UV)=100%
Amine: 3-Methyl-butylamine

Example 213

Compound 213

2-{6-[2-(3,5-Dichloro-pyridin-4-yl)-acetyl]-2,3-dimethoxy-phenoxy}-N-(4-methoxy-benzyl)-acetamide $^1$H NMR (DMSO-d$_6$) δ=8.67 (1H, t), 8.64 (2H, s), 7.61 (1H, d), 7.15 (2H, d), 6.99 (1H, d), 6.75 (2H, d), 4.75 (2H, s), 4.70 (2H, s), 4.26 (2H, d), 3.90 (3H, s), 3.76 (3H, s), 3.70 (3H, s)
Amine: 4-Methoxy-benzylamine

Example 214

Compound 214

2-{6-[2-(3,5-Dichloro-pyridin-4-yl)-acetyl]-2,3-dimethoxy-phenoxy}-N-(2,2-dimethyl-propyl)-acetamide LC/MS (METHOD A): (m/z) 469 (MH+); RT=7.44 min; purity (UV)=100%
Amine: 2,2-Dimethyl-propylamine

Example 215

Compound 215

N-Cyclohexyl-2-{6-[2-(3,5-dichloro-pyridin-4-yl)-acetyl]-2,3-dimethoxy-phenoxy}-acetamide LC/MS (METHOD A): (m/z) 481 (MH+); RT=7.52 min; purity (UV)=100%
Amine: Cyclohexylamine

Example 216

Compound 216

2-{6-[2-(3,5-Dichloro-pyridin-4-yl)-acetyl]-2,3-dimethoxy-phenoxy}-N-(3-methoxy-benzyl)-acetamide $^1$H NMR (DMSO-d$_6$) δ=8.72 (1H, t), 8.63 (2H, s), 7.60 (1H, d), 7.12 (1H, t), 6.99 (1H, d), 6.83-6.74 (3H, m), 4.75 (2H, s), 4.73 (2H, s), 4.30 (2H, d), 3.90 (3H, s), 3.78 (3H, s), 3.69 (3H, s).
Amine: 3-Methoxy-benzylamine

Example 217

Compound 217

N-Cycloheptyl-2-{6-[2-(3,5-dichloro-pyridin-4-yl)-acetyl]-2,3-dimethoxy-phenoxy}-acetamide LC/MS (METHOD A): (m/z) 495 (MH+); RT=7.84 min; purity (UV)=92.2%
Amine: Cycloheptylamine

Example 218

Compound 218

2-{6-[2-(3,5-Dichloro-pyridin-4-yl)-acetyl]-2,3-dimethoxy-phenoxy}-N-(2-methoxy-benzyl)-acetamide $^1$H NMR (DMSO-d$_6$) δ=8.64 (2H, s), 8.50 (1H, t), 7.62 (1H, d), 7.19 (1H, t), 7.12 (1H, d), 6.99 (1H, d), 6.93 (1H, d), 6.76 (1H, t), 4.78 (2H, s), 4.74 (2H, s), 4.31 (2H, d), 3.91 (3H, s), 3.79 (3H, s), 3.76 (3H, s).
Amine: 2-Methoxy-benzylamine

Example 219

Compound 219

N-Cyclohexylmethyl-2-{6-[2-(3,5-dichloro-pyridin-4-yl)-acetyl]-2,3-dimethoxy-phenoxy}-acetamide LC/MS (METHOD A): (m/z) 495 (MH+); RT=7.86 min; purity (UV)=100%
Amine: Cyclohexylmethylamine

Example 220

Compound 220

2-{6-[2-(3,5-Dichloro-pyridin-4-yl)-acetyl]-2,3-dimethoxy-phenoxy}-N-(2-hydroxy-ethyl)-acetamide LC/MS (METHOD A): (m/z) 442.9 (MH+); RT=5.41 min; purity (UV)=100%
Amine: 2-Hydroxy-ethylamine

Example 221

Compound 221

(R)-2-{6-[2-(3,5-Dichloro-pyridin-4-yl)-acetyl]-2,3-dimethoxy-phenoxy}-N-(1-phenyl-ethyl)-acetamide LC/MS (METHOD A): (m/z) 502.9 (MH+); RT=7.37 min; purity (UV)=100%
Amine: (R)-1-Phenyl-ethylamine

Example 222

Compound 222

2-{6-[2-(3,5-Dichloro-pyridin-4-yl)-acetyl]-2,3-dimethoxy-phenoxy}-N-(3-hydroxy-propyl)-acetamide LC/MS (METHOD A): (m/z) 457 (MH+); RT=5.51 min; purity (UV)=100%
Amine: 3-Hydroxy-propylamine

Example 223

Compound 223

2-{6-[2-(3,5-Dichloro-pyridin-4-yl)-acetyl]-2,3-dimethoxy-phenoxy}-N-(2-methoxy-ethyl)-acetamide LC/MS (METHOD A): (m/z) 457 (MH+); RT=6.12 min; purity (UV)=100%
Amine: 2-Methoxy-ethylamine

Example 224

Compound 224

2-{6-[2-(3,5-Dichloro-pyridin-4-yl)-acetyl]-2,3-dimethoxy-phenoxy}-N-(2-dimethylamino-ethyl)-acetamide LC/MS (METHOD A): (m/z) 470 (MH+); RT=4.26 min; purity (UV)=100%
Amine: 2-Dimethylamino-ethylamine

Example 225

Compound 225

2-(6-[2-(3,5-Dichloro-pyridin-4-yl)-acetyl]-2,3-dimethoxy-phenoxy)-N-(3-dimethylamino-propyl)-acetamide LC/MS (METHOD A): (m/z) 484 (MH+); RT=4.29 min; purity (UV)=100%
Amine: 3-Dimethylamino-propylamine

Example 226

Compound 226

(S)-2-(6-[2-(3,5-Dichloro-pyridin-4-yl)-acetyl]-2,3-dimethoxy-phenoxy)-N-(1-phenyl-ethyl)-acetamide LC/MS (METHOD A): (m/z) 503 (MH+); RT=7.39 min; purity (UV)=100%
Amine: (S)-1-Phenyl-ethylamine

Example 227

Compound 227

2-{6-[2-(3,5-Dichloro-pyridin-4-yl)-acetyl]-2,3-dimethoxy-phenoxy}-N-(3-isopropoxy-propyl)-acetamide LC/MS (METHOD A): (m/z) 498.9 (MH+); RT=6.89 min; purity (UV)=100%
Amine: 3-Isopropoxy-propylamine

Example 228

Compound 228

2-{6-[2-(3,5-Dichloro-pyridin-4-yl)-acetyl]-2,3-dimethoxy-phenoxy}-N-furan-2-ylmethyl-acetamide LC/MS (METHOD A): (m/z) 478.9 (MH+); RT=6.74 min; purity (UV)=100%
Amine: Furan-2-yl-methylamine

Example 229

Compound 229

2-{6-[2-(3,5-Dichloro-pyridin-4-yl)-acetyl]-2,3-dimethoxy-phenoxy}-N-pyridin-2-ylmethyl-acetamide LC/MS (METHOD A): (m/z) 490 (MH+); RT=5.17 min; purity (UV)=100%
Amine: Pyridine-2-yl-methylamine

Example 230

Compound 230

2-{6-[2-(3,5-Dichloro-pyridin-4-yl)-acetyl]-2,3-dimethoxy-phenoxy}-N-pyridin-3-ylmethyl-acetamide LC/MS (METHOD A): (m/z) 490 (MH+); RT=4.62 min; purity (UV)=100%
Amine: Pyridine-3-yl-methylamine

Example 231

Compound 231

2-{6-[2-(3,5-Dichloro-pyridin-4-yl)-acetyl]-2,3-dimethoxy-phenoxy}-N-(2-phenoxy-ethyl)-acetamide LC/MS (METHOD A): (m/z) 518.9 (MH+); RT=7.19 min; purity (UV)=98.3%
Amine: 2-Phenoxy-ethylamine

Example 232

Compound 232

2-{6-[2-(3,5-Dichloro-pyridin-4-yl)-acetyl]-2,3-dimethoxy-phenoxy}-N-pyridin-4-ylmethyl-acetamide LC/MS (METHOD A): (m/z) 490 (MH+); RT=4.46 min; purity (UV)=100%
Amine: Pyridine-4-yl-methylamine

Example 233

Compound 233

2-{6-[2-(3,5-Dichloro-pyridin-4-yl)-acetyl]-2,3-dimethoxy-phenoxy}-N-(4-ethyl-benzyl)-acetamide LC/MS (METHOD A): (m/z) 517 (MH+); RT=7.71 min; purity (UV)=96.8%
Amine: 4-Ethyl-benzylamine

Example 234

Compound 234

2-{6-[2-(3,5-Dichloro-pyridin-4-yl)-acetyl]-2,3-dimethoxy-phenoxy}-N-(3,5-difluoro-benzyl)-acetamide LC/MS (METHOD A): (m/z) 524.9 (MH+); RT=7.27 min; purity (UV)=95.3%
Amine: 3,5-Difluoro-benzylamine

Example 235

Compound 235

2-{6-[2-(3,5-Dichloro-pyridin-4-yl)-acetyl]-2,3-dimethoxy-phenoxy}-N-(2,3-difluoro-benzyl)-acetamide LC/MS (METHOD A): (m/z) 524.9 (MH+); RT=7.22 min; purity (UV)=100%
Amine: 2,3-Difluoro-benzylamine

Example 236

Compound 236

2-{6-[2-(3,5-Dichloro-pyridin-4-yl)-acetyl]-2,3-dimethoxy-phenoxy}-N-(2-pyridin-2-yl-ethyl)-acetamide LC/MS (METHOD A): (m/z) 503.9 (MH+); RT=4.54 min; purity (UV)=100%
Amine: 2-Pyridine-2-yl-ethylamine

Example 237

Compound 237

2-{6-[2-(3,5-Dichloro-pyridin-4-yl)-acetyl]-2,3-dimethoxy-phenoxy}-N-(2-methyl-benzyl)-acetamide LC/MS (METHOD A): (m/z) 503 (MH+); RT=7.37 min; purity (UV)=100%
Amine: 2-Methyl-benzylamine

Example 238

Compound 238

2-{6-[2-(3,5-Dichloro-pyridin-4-yl)-acetyl]-2,3-dimethoxy-phenoxy}-N-(3-fluoro-benzyl)-acetamide LC/MS (METHOD A): (m/z) 506.9 (MH+); RT=7.14 min; purity (UV)=100%
Amine: 3-Fluoro-benzylamine

Example 239

Compound 239

2-{6-[2-(3,5-Dichloro-pyridin-4-yl)-acetyl]-2,3-dimethoxy-phenoxy}-N-(3-methyl-benzyl)-acetamide LC/MS (METHOD A): (m/z) 503 (MH+); RT=7.39 min; purity (UV)=100%
Amine: 3-Methyl-benzylamine

Example 240

Compound 240

2-{6-[2-(3,5-Dichloro-pyridin-4-yl)-acetyl]-2,3-dimethoxy-phenoxy}-N-(4-methyl-benzyl)-acetamide LC/MS (METHOD A): (m/z) 502.9 (MH+); RT=7.39 min; purity (UV)=100%
Amine: 4-Methyl-benzylamine

Example 241

Compound 241

2-{6-[2-(3,5-Dichloro-pyridin-4-yl)-acetyl]-2,3-dimethoxy-phenoxy}-N-phenethyl-acetamide LC/MS (METHOD A): (m/z) 503 (MH+); RT=7.29 min; purity (UV)=100%
Amine: 2-Phenyl-ethylamine

Example 242

Compound 242

2-(6-[2-(3,5-Dichloro-pyridin-4-yl)-acetyl]-2,3-dimethoxy-phenoxy)-N-(2-pyridin-4-yl-ethyl)-acetamide $^1$H NMR (DMSO-$d_6$) δ=8.65 (2H, s), 8.44 (2H, d), 8.33 (1H, t), 7.60 (1H, d), 7.30 (2H, d), 6.99 (1H, d), 4.74 (2H, s), 4.62 (2H, s), 3.90 (3H, s), 3.75 (3H, s), 3.44 (2H, q), 2.81 (2H, t).
Amine: 2-Pyridine-4-yl-ethylamine

Example 243

Compound 243

2-{6-[2-(3,5-Dichloro-pyridin-4-yl)-acetyl]-2,3-dimethoxy-phenoxy}-N-(3-phenyl-propyl)-acetamide LC/MS (METHOD A): (m/z) 517 (MH+); RT=7.56 min; purity (UV)=100%
Amine: 3-Phenyl-propylamine

Example 244

Compound 244

N-(2-Chloro-benzyl)-2-{6-[2-(3,5-dichloro-pyridin-4-yl)-acetyl]-2,3-dimethoxy-phenoxy}-acetamide LC/MS (METHOD A): (m/z) 522.9 (MH+); RT=7.46 min; purity (UV)=100%
Amine: 2-Chloro-benzylamine

Example 245

Compound 245

2-{6-[2-(3,5-Dichloro-pyridin-4-yl)-acetyl]-2,3-dimethoxy-phenoxy}-N-(2-piperidin-1-yl-ethyl)-acetamide LC/MS (METHOD A): (m/z) 510 (MH+); RT=4.46 min; purity (UV)=92.5%
Amine: 2-Piperidin-1-yl-ethylamine

Example 246

Compound 246

N-(3-Chloro-benzyl)-2-{6-[2-(3,5-dichloro-pyridin-4-yl)-acetyl]-2,3-dimethoxy-phenoxy}-acetamide LC/MS (METHOD A): (m/z) 522.8 (MH+); RT=7.46 min; purity (UV)=100%
Amine: 3-Chloro-benzylamine

Example 247

Compound 247

2-{6-[2-(3,5-Dichloro-pyridin-4-yl)-acetyl]-2,3-dimethoxy-phenoxy}-N-(2-morpholin-4-yl-ethyl)-acetamide LC/MS (METHOD A): (m/z) 512 (MH+); RT=4.31 min; purity (UV)=98.1%
Amine: 2-Morpholin-4-yl-ethylamine

Example 248

Compound 248

N-(4-Chloro-benzyl)-2-{6-[2-(3,5-dichloro-pyridin-4-yl)-acetyl]-2,3-dimethoxy-phenoxy}-acetamide LC/MS (METHOD A): (m/z) 522.9 (MH+); RT=7.49 min; purity (UV)=98.7%
Amine: 4-Chloro-benzylamine

Example 249

Compound 249

2-{6-[2-(3,5-Dichloro-pyridin-4-yl)-acetyl]-2,3-dimethoxy-phenoxy}-N-(2-pyridin-3-yl-ethyl)-acetamide LC/MS (METHOD A): (m/z) 504 (MH+); RT=4.47 min; purity (UV)=100%
Amine: 2-Pyridine-3-yl-ethylamine

Example 250

Compound 250

2-{6-[2-(3,5-Dichloro-pyridin-4-yl)-acetyl]-2,3-dimethoxy-phenoxy}-N-(2-pyrrolidin-1-yl-ethyl)-acetamide LC/MS (METHOD A): (m/z) 496 (MH+); RT=4.37 min; purity (UV)=100%
Amine: 2-Pyrrolidin-1-yl-ethylamine

Example 251

Compound 251

N-(2-Acetylamino-ethyl)-2-{6-[2-(3,5-dichloro-pyridin-4-yl)-acetyl]-2,3-dimethoxy-phenoxy}-acetamide LC/MS (METHOD A): (m/z) 484 (MH+); RT=5.31 min; purity (UV)=100%
Amine: 2-Acetylamino-ethylamine

Example 252

Compound 252

(R)-2-{6-[2-(3,5-Dichloro-pyridin-4-yl)-acetyl]-2,3-dimethoxy-phenoxy}-N-(2-hydroxy-2-phenyl-ethyl)-acetamide LC/MS (METHOD A): (m/z) 518.9 (MH+); RT=6.47 min; purity (UV)=73.4%
Amine: (R)-2-Hydroxy-2-phenyl-ethylamine

Example 253

Compound 253

(S)-2-{6-[2-(3,5-Dichloro-pyridin-4-yl)-acetyl]-2,3-dimethoxy-phenoxy}-N-(2-hydroxy-2-phenyl-ethyl)-acetamide LC/MS (METHOD A): (m/z) 519 (MH+); RT=6.47 min; purity (UV)=73.8%
Amine: (S)-2-Hydroxy-2-phenyl-ethylamine

Example 254

Compound 254

2-{6-[2-(3,5-Dichloro-pyridin-4-yl)-acetyl]-2,3-dimethoxy-phenoxy}-N-thiophen-2-ylmethyl-acetamide LC/MS (METHOD A): (m/z) 494.9 (MH+); RT=6.97 min; purity (UV)=100%
Amine: Thiophen-2-yl-methylamine

Example 255

Compound 255

2-{6-[2-(3,5-Dichloro-pyridin-4-yl)-acetyl]-2,3-dimethoxy-phenoxy}-N-[3-(2-oxo-pyrrolidin-1-yl)-propyl]-acetamide LC/MS (METHOD A): (m/z) 524 (MH+); RT=5.66 min; purity (UV)=95.7%
Amine: 3-(2-Oxo-pyrrolidin-1-yl)-propylamine

Example 256

Compound 256

(2R)-2-(6-[2-(3,5-Dichloro-pyridin-4-yl)-acetyl]-2,3-dimethoxy-phenoxy)-N-(2-hydroxy-indan-1-yl)-acetamide LC/MS (METHOD A): (m/z) 530.8 (MH+); RT=6.62 min; purity (UV)=90.4%

Amine: (2R)-2-Hydroxy-indan-1-yl-amine

Example 257

Compound 257

N-Cycloheptylmethyl-2-{6-[2-(3,5-dichloro-pyridin-4-yl)-acetyl]-2,3-dimethoxy-phenoxy}-acetamide LC/MS (METHOD A): (m/z) 509 (MH+); RT=8.19 min; purity (UV)=100%

Amine: Cycloheptylmethylamine

Example 258

Compound 258

2-{6-[2-(3,5-Dichloro-pyridin-4-yl)-acetyl]-2,3-dimethoxy-phenoxy}-N-[2-(2-hydroxy-ethoxy)-ethyl]-acetamide LC/MS (METHOD A): (m/z) 487 (MH+); RT=5.41 min; purity (UV)=100%

Amine: 2-(2-Hydroxy-ethoxy)-ethylamine

Example 259

Compound 259

2-{6-[2-(3,5-Dichloro-pyridin-4-yl)-acetyl]-2,3-dimethoxy-phenoxy}-N-(4-dimethylamino-butyl)-acetamide LC/MS (METHOD A): (m/z) 497.9 (MH+); RT=4.36 min; purity (UV)=100%

Amine: 4-Dimethylamino-butylamine

Preparation 5

Compound 505

Resin bound 2-(3,5-dichloro-pyridin-4-yl)-1-(2,3-dihydroxy-4-methoxy-phenyl)-ethanone

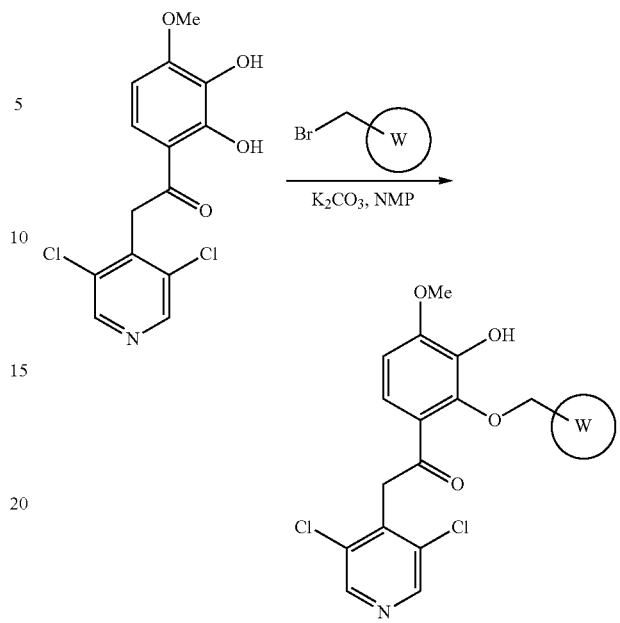

2-(3,5-Dichloro-pyridin-4-yl)-1-(2,3-dihydroxy-4-methoxy-phenyl)-ethanone (530 mg, 1.6 mmol) from preparation 3 was dissolved in dry NMP (5 mL), $K_2CO_3$ (210 mg, 1.5 mmol) was added followed by bromomethyl-Wang resin (560 mg, L=1.45 mmol/g, 0.81 mmol). The reaction mixture was vortexed at rt overnight. The resin was filtered and washed with MeOH:water (4:1, 3×10 mL), NMP (3×25 mL), MeOH (3×25 mL), dry THF (5×25 mL) and dried in vacuo to provide 760 mg of resin bound 2-(3,5-dichloro-pyridin-4-yl)-1-(2,3-dihydroxy-4-methoxy-phenyl)-ethanone.

General Procedure for Preparation of Compounds with Formula Im, Wherein R2 is as Defined Above:

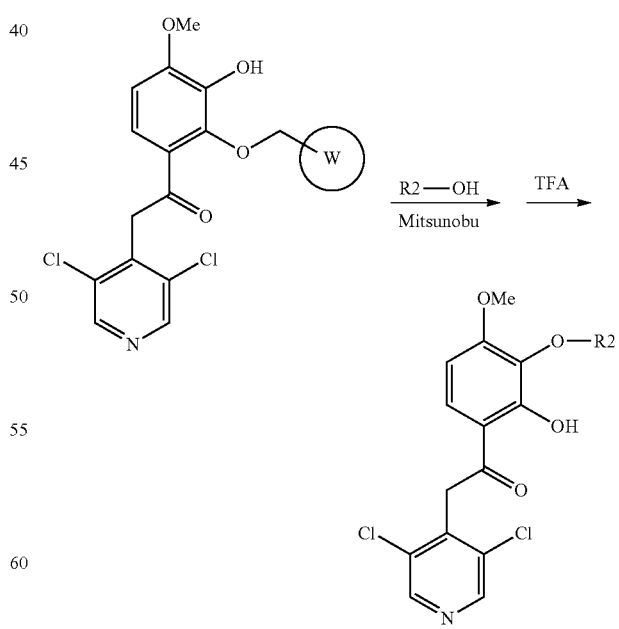

Resin bound 2-(3,5-dichloro-pyridin-4-yl)-1-(2,3-dihydroxy-4-methoxy-phenyl)-ethanone (90 mg, L=1.07 mmol/ g, 0.1 mmol) from preparation 5 was treated with a 1 mL of a stock solution of R2-OH (0.5 mmol) and PBu₃ (0.5 mmol.) cooled to 0° C. and then treated with 0.5 mL of a stock solution of TBAD (0.5 mmol). After 3 hours at rt the reaction mixture was filtered and 1 mL of the stock solution of R2-OH (0.5 mmol) and PBu₃ (0.5 mmol) was added. After cooling to 0° C. 0.5 mL of the stock solution of TBAD (0.5 mmol) was added. The reaction mixture was vortexed at rt overnight. The resin was washed with THF (5×3 mL) and DCE (5×3 mL). Cleavage of the products was performed by addition of a stock solution of DCE-TFA-TIS (90:10:1, 1 mL). After 30 min the cleavage solution was replaced by 1 mL of a fresh cleavage solution. After additional 30 min the combined cleavage solutions was evaporated in vacuo. The pure compounds were obtained by redissolving the reaction mixture in DMSO followed by standard preparative HPLC purification.

Using this procedure the following compounds were obtained:

Example 260

Compound 260

1-(3-Cyclopentyloxy-2-hydroxy-4-methoxy-phenyl)-2-(3,5-dichloro-pyridin-4-yl)-ethanone LC/MS (METHOD B): (m/z) 396 (MH+); RT=4.84 min; purity (UV)=100%
Alcohol: Cyclopentanol Example 261

Compound 261

1-(3-Cyclopropylmethoxy-2-hydroxy-4-methoxy-phenyl)-2-(3,5-dichloro-pyridin-4-yl)-ethanone LC/MS (METHOD B): (m/z) 382.1 (MH+); RT=4.36 min; purity (UV)=100%
Alcohol: Cyclopropylmethylalcohol Example 262

Compound 262

2-(3,5-Dichloro-pyridin-4-yl)-1-(3-ethoxy-2-hydroxy-4-methoxy-phenyl)-ethanone

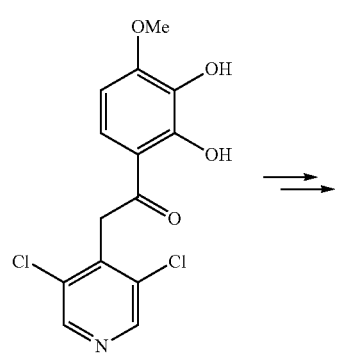

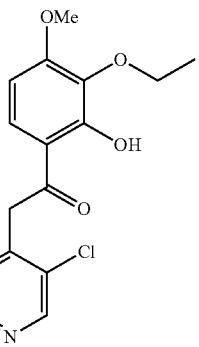

2-(3,5-Dichloro-pyridin-4-yl)-1-(2,3-dihydroxy-4-methoxy-phenyl)-ethanone (450 mg, 1.4 mmol) from preparation 3 was dissolved in dry DMF (10 mL). K₂CO₃ (566 mg, 4.1 mmol) was added followed by Ethyl iodide (442 μL, 5.5 mmol). The reaction mixture was stirred at rt overnight. Water (10 mL) was added and the organic products were extracted with EtOAc (2×25 ml). The combined organic phases were washed with water (10 mL) and brine (10 mL) and then dried over MgSO₄. The solvent was removed in vacuo and the pure product obtained be standard silica gel chromatography to provide 2-(3,5-Dichloro-pyridin-4-yl)-1-(2,3-diethoxy-4-methoxy-phenyl)-ethanone as a white solid. Yield 220 mg (42%). The compound was redissolved in DCM (1 mL) under argon. BCl₃ (0.97 mL of a 1M solution in DCM) was added slowly at room temperature. EtOH (2 mL) was added slowly after 2 hours. The solvent were removed in vacuo and the pure product obtained be standard silica gel chromatography to provide 2-(3,5-Dichloro-pyridin-4-yl)-1-(3-ethoxy-2-hydroxy-4-methoxyphenyl)-ethanone was obtained as a white solid. ¹H NMR (DMSO-d₆) δ=11.36 (1H, s), 8.67 (2H, s), 7.88 (1H, d), 6.77 (1H, d), 4.80 (2H, s), 3.96 (2H, q), 3.91 (3H, s), 1.26 (3H, t). Yield 100 mg (49%)

General Procedure for Preparation of Compounds with Formula In, Wherein R3 (R3≠Hydrogen) is as Defined Above:

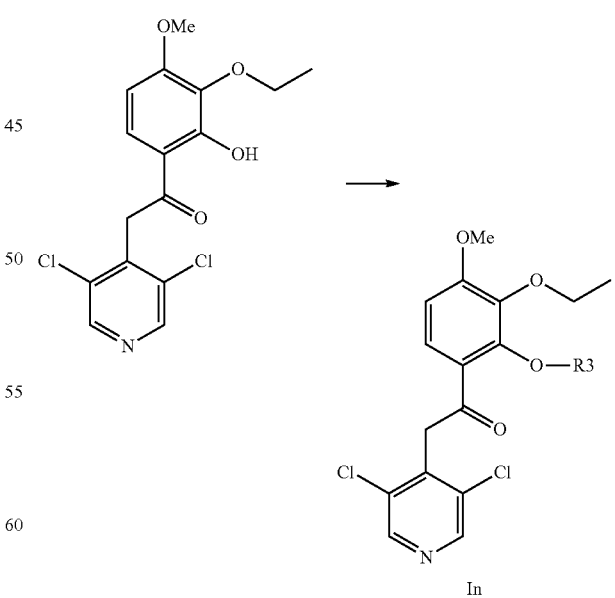

2-(3,5-Dichloro-pyridin-4-yl)-1-(3-ethoxy-2-hydroxy-4-methoxy-phenyl)-ethanone from example 263 (12 mg, 0.034 mmol) was dissolved in dry DMSO (0.25 mL). Aqueous K₂CO₃ (0.025 mL of a 2M) was added followed by 1.5 eq. of an alkyl bromide or iodide dissolved in 0.025 mL DMSO. The reaction mixture was left at for 48 hours. The pure compounds were obtained by standard preparative HPLC purification.

Using this procedure the following compounds were obtained:

Example 263

Compound 263

2-(3,5-Dichloro-pyridin-4-yl)-1-(3-ethoxy-4-methoxy-2-phenethyloxy-phenyl)-ethanone $^1$H NMR (CDCl$_3$) δ=8.47 (2H, s), 7.61 (1H, d), 7.26 (4H, m), 7.10 (1H, t), 6.75 (1H, d), 4.49 (2H, t), 4.43 (2H, s), 4.01 (2H, q), 3.91 (3H, s), 3.17 (2H, t), 1.35 (3H, t).

Alkyl halide: 2-Bromo-1-phenyl-ethane

Example 264

Compound 264

1-[2-(5-Cyclopropyl-[1,3,4]thiadiazol-2-ylmethoxy)-3-ethoxy-4-methoxy-phenyl]-2-(3,5-dichloro-pyridin-4-yl)-ethanone $^1$H NMR (CDCl$_3$) δ=8.47 (2H, s), 7.61 (1H, d), 6.81 (1H, d), 5.64 (2H, s), 4.56 (2H, s), 4.15 (2H, q), 3.95 (3H, s), 2.39 (1H, m), 1.41 (3H, t), 1.56-1.11 (4H, m).

Alkyl halide: 2-Chloromethyl-5-cyclopropyl-[1,3,4]thiadiazol

Example 265

Compound 265

{6-[2-(3,5-Dichloro-pyridin-4-yl)-acetyl]-2-ethoxy-3-methoxy-phenoxy}-acetic acid benzyl ester $^1$H NMR (DMSO-d$_6$) δ=8.62 (2H, s), 7.51 (1H, d), 7.32 (5H, m), 6.96 (1H, d), 5.19 (2H, s), 4.74 (2H, s), 3.98 (2H, q), 3.88 (3H, s), 1.27 (3H, t).

Alkyl halide: 2-Bromo-acetic acid benzyl ester

Example 266

Compound 266

1-(3-Allyloxy-2-hydroxy-4-methoxy-phenyl)-2-(3,5-dichloro-pyridin-4-yl)-ethanone

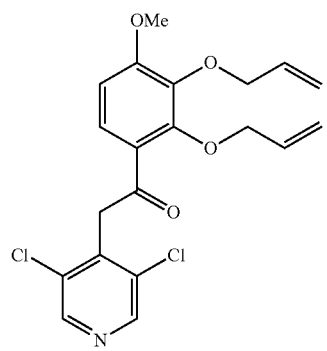

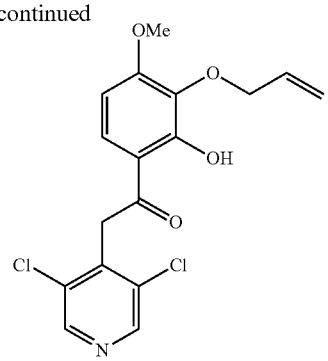

1-(2,3-Bis-allyloxy-4-methoxy-phenyl)-2-(3,5-dichloro-pyridin-4-yl)-ethanone from example 6 (3.9 g, 9.55 mmol) was dissolved in MeOH (96 mL) and cooled to 0° C. under argon. Pd(PPh$_3$)$_4$ (110 mg, 0.0955 mmol) was added followed by K2CO3 (1.3 g, 9.55 mmol). The cooling bath was removed and the reaction mixtured was stirred for 3 hours and then evaporated in vacuo. The crude was redissolved in EtOAc (100 mL) and washed twice with NH$_4$Cl (sat, 50 mL). The organic phase was dried over Na$_2$SO$_4$ and evaporated in vacuo and purified by flash chromatography using a gradient of toluene and 2% EtOAc as eluent. 1-(3-Allyloxy-2-hydroxy-4-methoxy-phenyl)-2-(3,5-dichloro-pyridin-4-yl)-ethanone was obtained as a white solid. $^1$H NMR (CDCl$_3$) δ=11.90 (1H, s), 8.53 (2H, s), 7.68 (1H, d), 6.58 (1H, d), 6.10 (1H, m), 5.26 (2H, m), 4.66 (2H, s), 4.59 (2H, d), 3.96 (3H, s). Yield 2.2 g (64%)

General Procedure for Preparation of Compounds with Formula Io, Wherein R3 (R3≠Hydrogen) is as Defined Above:

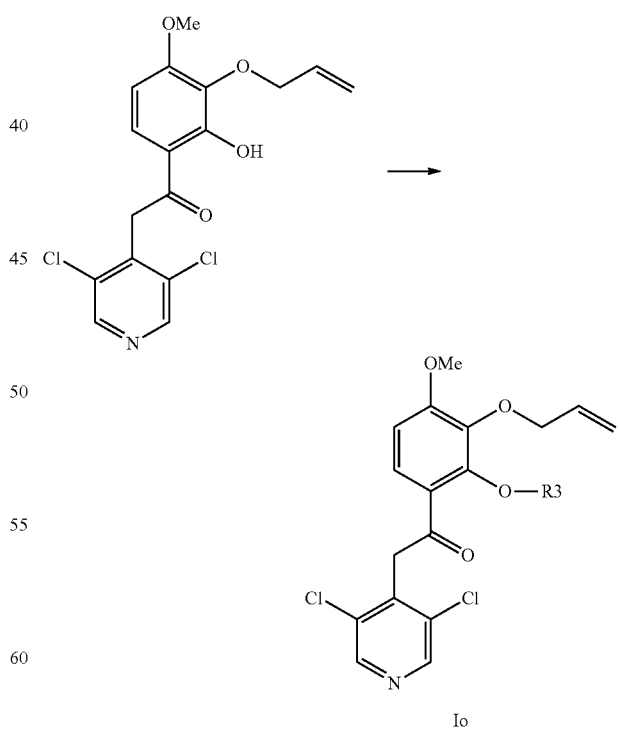

2-(3,5-Dichloro-pyridin-4-yl)-1-(3-ethoxy-2-hydroxy-4-methoxy-phenyl)-ethanone from example 263 (12 mg, 0.034 mmol) was dissolved in dry DMSO (0.25 mL). Aqueous K₂CO₃ (0.025 mL of a 2M) was added followed by 1.5 eq. of an alkyl bromide or iodide dissolved in 0.025 mL DMSO. The reaction mixture was left at it for 48 hours. The pure compounds were obtained by standard preparative HPLC purification.

Using this procedure the following compounds were obtained:

Example 267

Compound 267

2-{2-Allyloxy-6-[2-(3,5-dichloro-pyridin-4-yl)-acetyl]-3-methoxy-phenoxymethyl}-benzonitrile LC/MS (METHOD B): (m/z) 383.2 (MH+); RT=4.72 min; purity (UV)=100%
Alkyl halide: 2-Chloromethyl-benzonitrlie Example 268

Compound 268

1-(3-Allyloxy-4-methoxy-2-phenethyloxy-phenyl)-2-(3,5-dichloro-pyridin-4-yl)-ethanone LC/MS (METHOD B): (m/z) 472.3 (MH+); RT=5.32 min; purity (UV)=100%
Alkyl halide: 1-Bromo-2-phenyl-ethane Example 269

Compound 269

1-{3-Allyloxy-2-[2-(4-fluoro-phenyl)-ethoxy]-4-methoxy-phenyl}-2-(3,5-d chloro-pyridin-4-yl)-ethanone LC/MS (METHOD B): (m/z) 490.2 (MH+); RT=5.26 min; purity (UV)=100%
Alkyl halide: 1-Bromo-2-(4-fluoro-phenyl)-ethane General Procedure for Preparation of Compounds with Formula Ip, Wherein R3 is as Defined Above:

1-(2-Alkoxy-3,4-dimethoxy-phenyl)-2-(3,5-dichloro-pyridin-4-yl)-ethanone from the previous examples (0.021 mmol) was dissolved in dry DCM (0.25 mL). Methyltrioxorhenium (0.105 mmol) was added followed by hydrogenperoxide (0.042 mmol) and the reaction mixture was stirred at rt overnight. MnO₂ (0.063 mmol) was added. After 2 minutes the reaction mixture was after filtered and the reaction mixture evaporated in vacuo. The crude was re-dissolved in DMSO (0.4 mL). The pure compounds were obtained by standard preparative HPLC purification.

Using this procedure the following compounds were obtained:

Example 270

Compound 270

N-Benzyl-2-{6-[2-(3,5-dichloro-1-oxy-pyridin-4-yl)-acetyl]-2,3-dimethoxy-phenoxy}-acetamide ¹H NMR (CDCl₃) δ=8.15 (2H, s), 8.10 (1H, bs), 7.62 (1H, d), 7.30 (5H, m), 6.76 (1H, d), 4.72 (2H, s), 4.50 (2H, d), 4.46 (2H, s), 3.95 (3H, s), 3.80 (3H, s). Using N-benzyl-2-{6-[2-(3,5-dichloro-pyridin-4-yl)-acetyl]-2,3-dimethoxy-phenoxy}-acetamide from example 203 as starting material.

Example 271

Compound 271

2-(3,5-Dichloro-1-oxy-pyridin-4-yl)-1-(3,4-dimethoxy-2-phenethyloxy-phenyl)-ethanone ¹H NMR (CDCl₃) δ=8.13 (2H, s), 7.61 (1H, d), 7.26 (5H, m), 6.75 (1H, d), 4.40 (2H, t), 4.30 (2H, s), 3.93 (3H, s), 3.79 (3H, s), 3.17 (2H, t).

Using 2-(3,5-dichloro-pyridin-4-yl)-1-(3,4-dimethoxy-2-phenethyloxy-phenyl)-ethanone from example 112 as starting material.

Example 272

Compound 272

2-(3,5-Dichloro-1-oxy-pyridin-4-yl)-1-{2-[2-(4-fluoro-phenyl)-ethoxy]-3,4-dimethoxy-phenyl}-ethanone ¹H NMR (CDCl₃) δ=8.19 (2H, s), 7.61 (1H, d), 7.26 (2H, t), 6.95 (2H, t), 6.75 (1H, d), 4.44 (2H, t), 4.34 (2H, s), 3.93 (3H, s), 3.77 (3H, s), 3.14 (2H, t).

Using 2-(3,5-dichloro-pyridin-4-yl)-1-{2-[2-(4-fluoro-phenyl)-ethoxy]-3,4-dimethoxy-phenyl}-ethanone from example 129 as starting material.

Example 274

Compound 274

2-(3,5-Dichloro-1-oxy-pyridin-4-yl)-1-{3,4-di methoxy-2-[2-(1-oxy-pyridin-4-yl)-ethoxy]-phenyl}-ethanone $^1$H NMR (DMSO-d$_5$) δ=8.62 (2H, s), 8.11 (2H, d), 7.54 (1H, d), 7.39 (2H, d), 6.97 (1H, d), 4.41 (4H, m), 3.88 (3H, s), 3.67 (3H, s), 3.11 (2H, t).

Using example 100 as starting material.

Example 275

Compound 275

2-(3,5-Dichloro-1-oxy-pyridin-4-yl)-1-(2-hydroxy-3,4-dimethoxy-Phenyl)-ethanone $^1$H NMR (DMSO-d$_5$) δ=11.20 (1H, bs), 8.64 (2H, s), 7.84 (1H, d), 6.77 (1H, d), 4.70 (2H, bs), 3.91 (3H, s), 3.72 (3H, s).

Using 2-(3,5-dichloro-pyridin-4-yl)-1-(2-hydroxy-3,4-dimethoxy-phenyl)-ethanone from example 1 as starting material.

Example 276

Compound 276

4-(2-{6-[2-(3,5-Dichloro-1-oxy-pyridin-4-yl)-acetyl]-2,3-dimethoxy-phenoxy}-ethyl)-benzonitrile $^1$H NMR (DMSO-d$_6$) δ=8.61 (2H, s), 7.73 (2H, d), 7.55 (3H, m), 6.96 (1H, d), 4.45 (2H, t), 4.20 (2H, s), 3.88 (3H, s), 3.66 (3H, s), 3.22 (2H, t).

Using example 100 as starting material.

General Procedure for Preparation of Compounds with Formula Iq, Wherein R3≠Hydrogen) is as Defined Above:

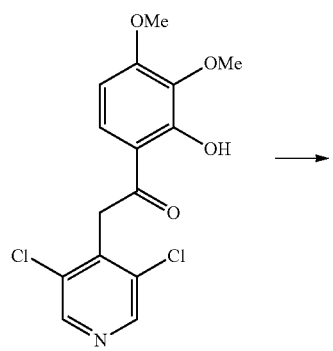

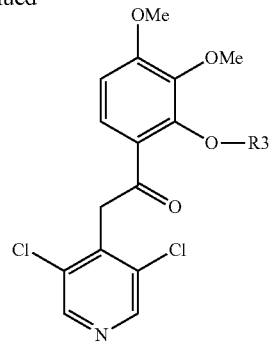

2-(3,5-Dichloro-pyridin-4-yl)-1-(2-hydroxy-3,4-dimethoxy-phenyl)-ethanone from example 1 (1.5 mmol) or 2-(3,5-Dichloro-1-oxy-pyridin-4-yl)-1-(2-hydroxy-3,4-dimethoxy-phenyl)-ethanone from example 274 (1.5 mmol), PBu$_3$ (1.5 mmol) and R3-OH (1.0 mmol) was dissolved in dry benzene (10 mL) under argon. The reaction mixture was cooled to 0° C. and then treated with ADDP (1.5 mmol). After 0.5 hours the reaction mixture was brought to rt and stirred overnight. Decalite was added and the reaction mixture was evaporated in vacuo and purified by flash chromatography using a gradient of petroleum ether and EtOAc as eluent.

Using this procedure the following compounds were obtained:

Example 277

Compound 277

2-(3,5-Dichloro-pyridin-4-yl)-1-[3,4-dimethoxy-2-(2-pyridin-4-yl-ethoxy)-phenyl]-ethanone $^1$H NMR (DMSO-d$_6$) δ=8.63 (2H, s), 8.44 (2H, d), 7.53 (1H, d), 7.37 (2H, d), 6.97 (1H, d), 4.46 (4H, m), 3.88 (3H, s), 3.66 (3H, s), 3.15 (2H, t).

R3-OH: 2-Pyridin-4-yl-ethanol

Example 278

Compound 278

4-(2-{6-[2-(3,5-Dichloro-pyridin-4-yl)-acetyl]-2,3-dimethoxy-phenoxy}-ethyl)-benzonitrile $^1$H NMR (DMSO-d$_6$) δ=8.63 (2H, s), 7.70 (2H, d), 7.55 (3H, m), 6.97 (1H, d), 4.47 (2H, t), 4.30 (2H, s), 3.89 (3H, s), 3.68 (3H, s), 3.23 (2H, t).

R3-OH: 4-(2-Hydroxy-ethyl)-benzonitrile prepared from 2-(4-bromo-phenyl)-ethanol according to

Example 279

Compound 279

2-(3,5-Dichloro-pyridin-4-yl)-1-[3,4-dimethoxy-2-(2-pyridin-2-yl-ethoxy)-phenyl]-ethanone $^1$H NMR (DMSO-d$_6$) δ=8.62 (2H, s), 8.41 (1H, t), 7.65 (1H, t), 7.50 (1H, d), 7.38 (1H, d), 7.10 (1H, m), 6.95 (1H, d), 4.61 (2H, t), 4.38 (2H, s), 3.88 (3H, s), 3.72 (3H, s), 3.28 (2H, t).

R3-OH: 2-Pyridin-2-yl-ethanol

Example 280

Compound 280

2-(3,5-Dichloro-pyridin-4-yl)-1-[3,4-dimethoxy-2-(2-pyridin-3-yl-ethoxy)-phenyl]-ethanone $^1$H NMR (DMSO-d$_6$) δ=8.64 (2H, s), 8.55 (1H, s), 8.34 (1H, d), 7.77 (1H, d), 7.53 (1H, d), 7.28 (1H, m), 6.97 (1H, d), 4.47 (2H, s), 4.43 (2H, t), 3.88 (3H, s), 3.64 (3H, s), 3.15 (2H, t).

R3-OH: 2-Pyridin-3-yl-ethanol

Example 281

Compound 281

2-(3,5-Dichloro-pyridin-4-yl)-1-{2-[2-(4-methane-sulfinyl-phenyl)-ethoxy]-3,4-dimethoxy-phenyl}-ethanone (CDCl$_3$) δ=8.50 (2H, s), 7.59 (3H, m), 7.49 (2H, d), 6.78 (1H, d), 4.48 (4H, m), 3.93 (3H, s), 3.74 (3H, s), 3.24 (2H, t), 2.63 (3H, s).

R3-OH: 2-(4-Methanesulfinyl-phenyl)-ethanol, prepared by oxidising 2-(4-methylsulfanyl-phenyl)-ethanol with 1.5 eq MCPBA in DCM rt overnight. $^1$H NMR (CDCl$_3$) δ=7.88 (2H, d), 7.45 (2H, d), 3.92 (2H, t), 3.04 (3H, s), 2.97 (2H, t), 1.70 (1H, bs). LC/MS (METHOD B): (m/z) 185 (MH+); RT=1.27 min

Example 282

Compound 282

2-(3,5-Dichloro-pyridin-4-yl)-1-{2-[2-(4-methane-sulfonyl-phenyl)-ethoxy]-3,4-dimethoxy-phenyl}-ethanone $^1$H NMR (CDCl$_3$) δ=8.50 (2H, s), 7.88 (2H, d), 7.59 (1H, d), 7.53 (2H, d), 6.77 (1H, d), 4.51 (2H, s), 4.49 (2H, t), 3.93 (3H, s), 3.72 (3H, s), 3.27 (2H, t), 2.98 (3H, s).

R3-OH: 2-(4-Methanesulfonyl-phenyl)-ethanol, prepared by oxidising 2-(4-methylsulfanyl-phenyl)-ethanol with 1.5 eq MCPBA in DCM rt overnight. NMR (CDCl$_3$) δ=7.59 (2H, d), 7.40 (2H, d), 3.90 (2H, t), 2.94 (2H, t), 2.72 (3H, s), 1.85 (1H, bs). LC/MS (METHOD B): (m/z) 201 (MH+); RT=1.48 min

Example 283

Compound 283

2-(3,5-Dichloro-pyridin-4-yl)-1-[3,4-dimethoxy-2-(1-phenyl-propoxy)-phenyl]-ethanone $^1$H NMR (DMSO-d$_6$) δ=8.65 (2H, s), 7.34 (6H, m), 6.85 (1H, d), 5.48 (1H, t), 4.63 (2H, s), 3.85 (3H, s), 3.72 (3H, s), 2.14 (1H, m), 1.95 (1H, m), 0.88 (3H, t).

R3-OH: 1-Phenyl-propan-1-ol

Example 284

Compound 284

2-(3,5-Dichloro-pyridin-4-yl)-1-[3,4-dimethoxy-2-(2-phenyl-propoxy)-phenyl]-ethanone $^1$H NMR (DMSO-d$_6$) δ=8.62 (2H, s), 7.51 (1H, d), 7.35 (2H, d), 7.23 (2H, t), 7.06 (1H, t), 6.95 (1H, d), 4.33 (4H, m), 3.88 (3H, s), 3.69 (3H, s), 3.33 (1H, m), 1.37 (3H, d).

R3-OH: 2-Phenyl-propan-1-ol

Example 285

Compound 285

2-(3,5-Dichloro-pyridin-4-yl)-1-[3,4-dimethoxy-2-(1-methyl-2-phenyl-ethoxy)-phenyl]-ethanone $^1$H NMR (DMSO-d$_6$) δ=8.66 (2H, s), 7.46 (1H, d), 7.28 (4H, d), 7.17 (1H, m), 6.93 (1H, d), 4.94 (1H, m), 4.60 (2H, m), 3.88 (3H, s), 3.58 (3H, s), 3.02 (2H, m), 1.18 (3H, d).

R3-OH: 1-Phenyl-propan-2-ol

Preparation 6

Compound 506

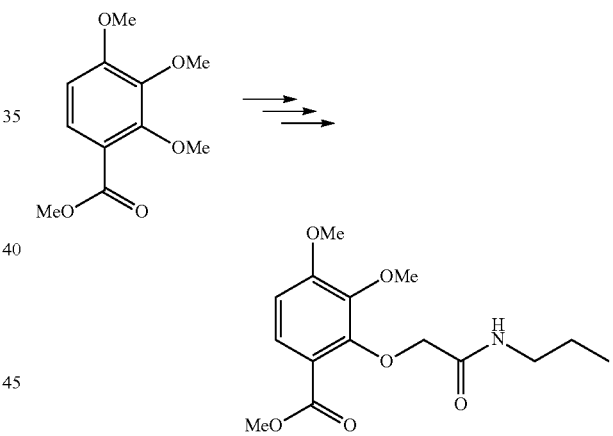

Methyl 2,3,4-trimethoxybenzoic acid (25.7 g, 114 mmol) was dissolved in DCM (25 mL) under argon. BCl$_3$ (133 mL of an 1M solution in DCM, 133 mmol) was added dropwise and the reaction mixture was left at it for 2 hours. EtOH (200 mL) was added and the reaction mixture was stirred for 2 hours. Filter the precipitate and recryst. from EtOAc-petrol ether to provide 6 g (25%) of 2-hydroxy-3,4-dimethoxy-benzoic acid methyl ester as a white solid. $^1$H NMR (CDCl$_3$) δ=10.90 (1H, s), 7.59 (1H, d), 6.48 (1H, d), 3.93 (3H, s), 3.92 (3H, s), 3.89 (3H, s). 2-Hydroxy-3,4-dimethoxy-benzoic acid methyl ester (6 g, 28.2 mmol) was redissolved in NMP (35 mL) and treated with tert-butyl bromoacetate (42.4 mmol) and K$_2$CO$_3$ (42.4 mmol). The reaction mixture was heated to 50° C. overnight. The reaction mixture was poured into water (300 mL). The organic products were extracted with EtOAc (2×100 mL), and the combined organic phases washed with NaCl (sat, 100 mL). The organic phase was dried over Na$_2$SO$_4$, evaporated in vacuo and purified by flash chromatography using a gradient of EtOAc in heptane as eluent to provide 2-tert-butoxycarbonylmethoxy-3,4-dimethoxy-benzoic acid methyl ester (compound 506a) as a colourless oil. $^1$H NMR (CDCl$_3$) δ=7.58 (1H, d), 6.71 (1H, d), 4.56 (2H, s), 3.90 (3H, s), 3.87 (3H, s), 3.86 (3H, s), 1.50 (9H, s). Yield 8.19 g (89%). 2-tert-Butoxycarbonylmethoxy-3,4-dimethoxy-benzoic acid methyl ester (8.19 g, 25.1 mmol) was dissolved in DCM (50 mL) and treated with triethylsilane (4 mL, 25.1 mmol) and TFA (9.66 mL, 125.5 mmol). The reaction mixture was left overnight. The reaction mixture was evaporated in vacuo, redissolved in toluene (200 mL) and evaporated to dryness. This procedure was repeated three times to afford 2-carboxymethoxy-3,4-dimethoxy-benzoic acid methyl ester (compound 506b) as a white solid. NMR (CDCl$_3$) δ=12.6 (1H, bs), 7.75 (1H, d), 6.73 (1H, d), 4.84 (2H, s), 3.95 (3H, s), 3.92 (3H, s), 3.85 (3H, s). Yield 6.71 g (99%). 2-Carboxymethoxy-3,4-dimethoxy-benzoic acid methyl ester (6.71 g, 24.8 mmol) was dissolved in dry DMF (130 mL) under argon. Propylamine (4.1 mL, 49.8 mmol) was added followed by HATU (11.32 g, 29.8 mmol) and the reaction mixture was left overnight. The solvent was evaporated in vacuo and the crude mixture was redissolved in EtOAc (150 mL). Wash the organic phase with CaCl$_2$ aq. (2×50 mL), water (2×50 mL) and brine (50 mL). The organic phase was dried over Na$_2$SO$_4$, evaporated in vacuo and purified by flash chromatography using a gradient of EtOAc in heptane as eluent. 3,4-Dimethoxy-2-propylcarbamoylmethoxy-benzoic acid methyl ester (compound 506c) was obtained as a white solid. $^1$H NMR (CDCl$_3$) δ=8.47 (1H, bs), 7.71 (1H, d), 6.70 (1H, d), 4.69 (2H, s), 3.93 (3H, s), 3.87 (3H, s), 3.83 (3H, s), 3.33 (2H, q), 1.64 (2H, m), 0.99 (3H, t). Yield 6.67 g (86%). General Procedure for Preparation of Compounds with Formula Ir, Wherein Ar and HetAr is as Defined Above:

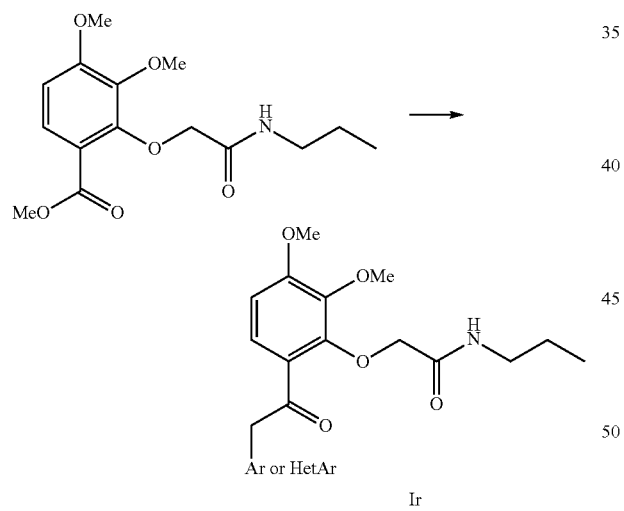

3,4-Dimethoxy-2-propylcarbamoylmethoxy-benzoic acid methyl ester (28 mg, 0.09 mmol) obtained from Preparation 6 and a Ar-Me or HetAr-Me compound (1.2 eq, see below) was dissolved in dry THF (1 mL) under argon. The mixture was cooled to 0° and treated dropwise with LiHMDS (0.273 mL of a 1M solution). The reaction mixture was brought to room temperature and left overnight. The reaction was quenched with NH$_4$Cl (sat., 2 mL) and the organic products were extracted with EtOAc (2×2 mL). The combined organic phases was washed with NaCl (sat, 2 mL). The organic phase was dried over Na$_2$SO$_4$, evaporated in vacuo and redissolved in MeOH (0.350 mL) followed by standard HPLC purification.

Using this procedure the following compounds were obtained:

Example 286

Compound 286

2-{6-[2-(6-Chloro-pyrazin-2-yl)-acetyl]-2,3-dimethoxy-phenoxy}-N-propyl-acetamide LC/MS (METHOD B): (m/z) 408.4 (MH+); RT=3.33 min; purity (UV)=91%

HetAr-Me: 2-Chloro-6-methyl-pyrazine

Example 287

Compound 287

2-{6-[2-(3-Bromo-pyrazin-2-yl)-acetyl]-2,3-dimethoxy-phenoxy}-N-Propyl-acetamide LC/MS (METHOD B): (m/z) 454.3 (MH+); RT=3.26 min; purity (UV)=86%

HetAr-Me: 2-Bromo-3-methyl-pyrazine

Example 288

Compound 288

2-{6-[2-(2,6-Dichloro-phenyl)-acetyl]-2,3-dimethoxy-phenoxy}-N-propyl-acetamide $^1$H NMR (CDCl$_3$) δ=7.84 (1H, bs), 7.68 (1H, d), 7.34 (2H, d), 7.19 (1H, t), 6.77 (1H, d), 4.66 (2H, s), 4.60 (2H, s), 3.95 (3H, s), 3.86 (3H, s), 3.25 (2H, q), 1.48 (2H, m), 0.86 (3H, t).

Ar-Me: 1,3-Dichloro-2-methyl-benzene

Example 289

Compound 289

2-[2,3-Dimethoxy-6-(2-pyridin-4-yl-acetyl)-phenoxy]-N-propyl-acetamide $^1$H NMR (DMSO-d$_5$) δ=8.49 (2H, bs), 8.15 (1H, t), 7.55 (1H, d), 7.24 (2H, d), 6.95 (1H, d), 4.56 (2H, s), 4.44 (2H, s), 3.88 (3H, s), 3.77 (3H, s), 3.09 (2H, q), 1.42 (2H, m), 0.81 (3H, t).

HetAr-Me: 4-Methyl-pyridine

Example 290

Compound 290

2-[2,3-Dimethoxy-6-(2-quinolin-4-yl-acetyl-phenoxy]-N-propyl-acetamide LC/MS (METHOD B): (m/z) 423.4 (MH+); RT=2.45 min; purity (UV)=100%

HetAr-Me: 4-Methyl-quinoline

Example 291

Compound 291

2-[2,3-Dimethoxy-6-(2-pyrazin-2-yl-acetyl)-phenoxy]-N-propyl-acetamide LC/MS (METHOD B): (m/z) 374.1 (MH+); RT=2.58 min; purity (UV)=81%

HetAr-Me: 2-Methyl-pyrazine

Example 292

Compound 292

2-{6-[2-(3-Bromo-pyridin-4-yl)-acetyl]-2,3-dimethoxy-phenoxy}-N-propyl-acetamide LC/MS (METHOD B): (m/z) 453.07 (MH+); RT=3.13 min; purity (UV)=100%
HetAr-Me: 3-Bromo-4-methyl-pyridine

Example 293

Compound 293

2-{6-[2-(3,5-Dibromo-pyridin-4-yl)-acetyl]-2,3-dimethoxy-phenoxy}-N-propyl-acetamide LC/MS (METHOD B): (m/z) 531.0 (MH+); RT=3.68 min; purity (UV)=100%
HetAr-Me: 3,5-Dibromo-4-methyl-pyridine

Example 294

Compound 294

2-(6-[2-(6-Chloro-pyrimidin-4-yl)-acetyl]-2,3-dimethoxy-phenoxy)-N-propyl-acetamide LC/MS (METHOD B): (m/z) 408.3 (MH+); RT=3.19 and 3.79 min (probably keton and enol isomer); purity (UV)=100%
HetAr-Me: 4-Chloro-6-methyl-pyrimidine

Example 295

Compound 295

2-(6-[2-(4-Chloro-pyridin-2-yl)-acetyl]-2,3-dimethoxy-phenoxy)-N-propyl-acetamide LC/MS (METHOD B): (m/z) 407.4 (MH+); RT=3.50 min; purity (UV)=100%
HetAr-Me: 4-Chloro-2-methyl-pyridine

Example 296

Compound 296

2-{6-[2-(2-Chloro-pyridin-3-yl)-acetyl]-2,3-dimethoxy-phenoxy}-N-propyl-acetamide LC/MS (METHOD B): (m/z) 407.4 (MH+); RT=3.26 min; purity (UV)=100%
HetAr-Me: 2-Chloro-3-methyl-pyridine

Example 297

Compound 297

2-(2,3-Dimethoxy-6-[2-(2-methoxy-pyridin-4-yl)-acetyl]-phenoxy)-N-propyl-acetamide LC/MS (METHOD B): (m/z) 403.3 (MH+); RT=3.24 min; purity (UV)=100%
HetAr-Me: 2-Methoxy-4-methyl-pyridine

Example 298

Compound 298

2-(6-[2-(2-Cyano-pyridin-4-yl)-acetyl]-2,3-dimethoxy-phenoxy)-N-propyl-acetamide LC/MS (METHOD B): (m/z) 398.4 (MH+); RT=3.23 min; purity (UV)=94%
HetAr-Me: 4-Methyl-pyridine-2-carbonitrile

Example 299

Compound 299

2-[2,3-Dimethoxy-6-(2-pyridazin-3-yl-acetyl)-phenoxy]-N-propyl-acetamide

LC/MS (METHOD B): (m/z) 374.2 (MH+); RT=2.39 min; purity (UV)=90%
HetAr-Me: 3-Methyl-pyridazine

Example 300

Compound 300

2-(2-tert-Butylamino-3,5-dichloro-pyridin-4-yl)-1-{2-[2-(4-fluoro-phenyl)-ethoxy]-3,4-dimethoxy-phenyl}-ethanone

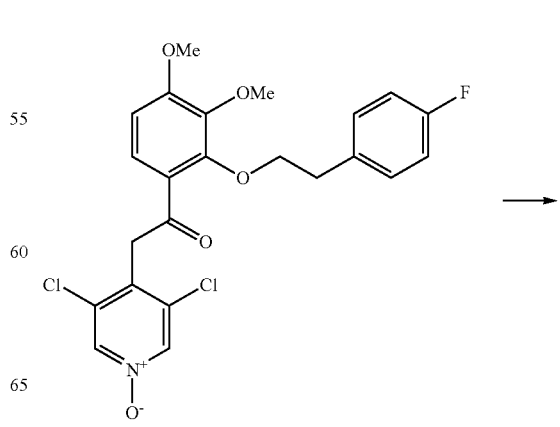

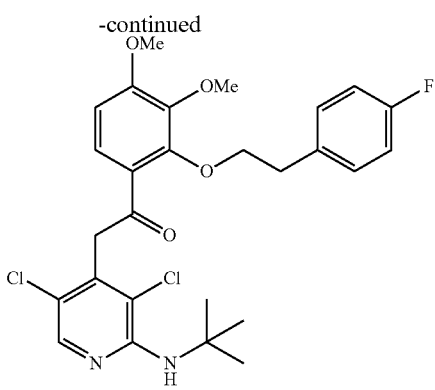

2-(3,5-Dichloro-1-oxy-pyridin-4-yl)-1-{2-[2-(4-fluoro-phenyl)-ethoxy]-3,4-dimethoxy-phenyl}-ethanone obtained from example 272 was converted into 2-(2-tert-Butylamino-3,5-dichloro-pyridin-4-yl)-1-{2-[2-(4-fluoro-phenyl)-ethoxy]-3,4-dimethoxy-phenyl}-ethanone according to the procedure described in *J. Org. Chem.* (2007), 72, 4554-57. Pure 2-(2-tert-butylamino-3,5-dichloro-pyridin-4-yl)-1-{2-[2-(4-fluoro-phenyl)-ethoxy]-3,4-dimethoxy-phenyl}-ethanone was obtained by standard HPLC purification.

LC/MS (METHOD B): (m/z) 535.2 (MH+); RT=6.21 min; purity (UV)=100%

Example 301

Compound 301

2-(2-amino-3,5-dichloro-pyridin-4-yl)-1-{2-[2-(4-fluoro-phenyl)-ethoxy]-3,4-dimethoxy-phenyl}-ethanone

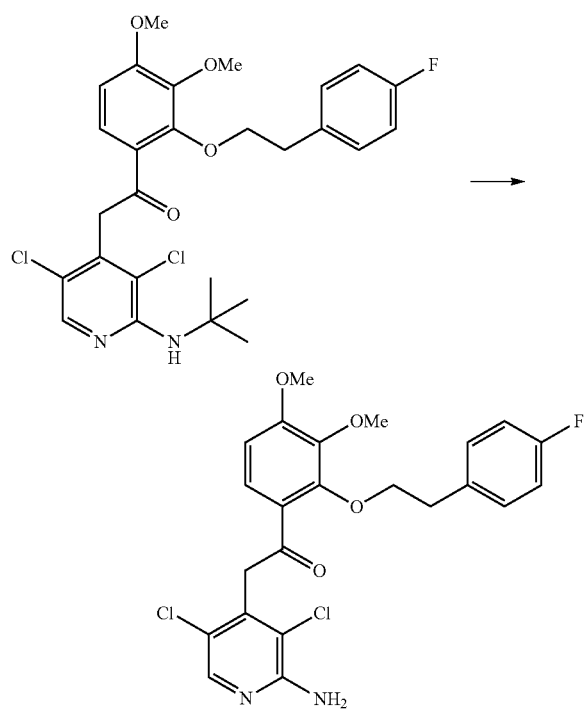

2-(2-tert-Butylamino-3,5-dichloro-pyridin-4-yl)-1-{2-[2-(4-fluoro-phenyl)-ethoxy]-3,4-dimethoxy-phenyl}-ethanone obtained from example 300 (16.5 mg, 0.0308 mmol), triethylsilane (2 eq.) and TFA (0.1 mL) in dichloroethane (0.2 mL) was heated to 50° C. for 24 hours. The crude mixture was evaporated in vacuo, redissolved in dichloroethane (1 mL) and washed with NaHCO₃ (sat, 2×0.5 mL). The organic phase was dried over Na₂SO₄ and the solvent evaporated in vacuo. Pure 2-(2-amino-3,5-dichloro-pyridin-4-yl)-1-{2-[2-(4-fluoro-phenyl)-ethoxy]-3,4-dimethoxy-phenyl}-ethanone was obtained by flash chromatography using a gradient of MeOH in dichloromethane as eluent.

LC/MS (METHOD B): (m/z) 479.3 (MH+); RT=4.53 min; purity (UV)=3.00%

Example 302

Compound 302

2-(3,5-Dichloro-pyridin-4-yl)-1-(4-ethoxy-3-methoxy-2-phenethyloxy-phenyl)-ethanone

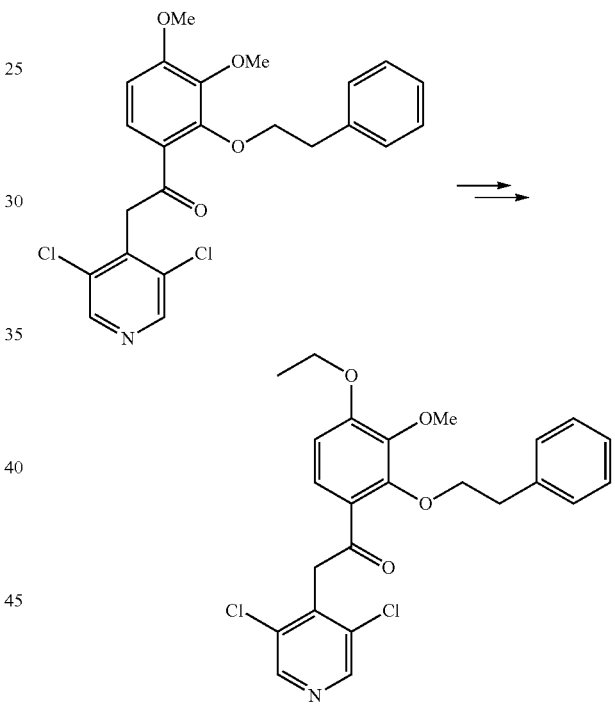

2-(3,5-Dichloro-pyridin-4-yl)-1-(3,4-dimethoxy-2-phenethyloxy-phenyl)-ethanone obtained from example 112 (89.3 mg, 0.1 mmol) was treated with piperidine (0.8 mL) and water (0.32 mL). The yellow suspension was heated to 90° C. for 54 hours. The solvent was evaporated in vacuo. The crude mixture was treated with NH₄Cl (sat., 1 mL) and the organic products were extracted with EtOAc (3×2 mL). The combined organic phases was dried over Na₂SO₄ and evaporated in vacuo. Purification by flash chromatography using a gradient of EtOAc in toluene as eluent provided 2-(3,5-dichloro-pyridin-4-yl)-1-(4-hydroxy-3-methoxy-2-phenethyloxy-phenyl)-ethanone as a white solid. Yield 8.6 mg (20%). 2-(3,5-Dichloro-pyridin-4-yl)-1-(4-hydroxy-3-methoxy-2-phenethyloxy-phenyl)-ethanone (5.5 mg, 0.013 mmol) was dissolved in DMSO (0.45 mL) and treated with K₂CO₃ (0.019 mL of a 1M aq. solution) followed by ethyliodide (0.019 mL of a 1M solution in DMSO). The reaction mixture was left at rt for 48 hours and purified by standard HPLC purification. 2-(3,5-Dichloro-pyridin-4-yl)-1-(4-ethoxy-3-methoxy-2-phenethyloxy-phenyl)-ethanone was obtained as a colourless solid. Yield 3.2 mg (36%).

$^1$H NMR (CDCl$_3$) δ=8.48 (2H, s), 7.59 (1H, d), 7.27 (4H, m), 7.11 (1H, t), 6.73 (1H, d), 4.48 (4H, m), 4.14 (2H, q), 3.78 (3H, s), 3.18 (2H, t), 1.49 (3H, t).

Example 303

PDE4 Assay

Human recombinant PDE4 (Gene bank accession no NM_006203) are incubated for 1 hour, respectively, with the test compound at concentrations up to 10 uM, with cAMP ($1 \times 10^{-5}$ M), and with a low amount (0.021 MBq) of radioactively labelled CAMP. At the end of the incubation, the cleavage of the substrate is evaluated by the binding of the AMP product to SPA beads, which generate chemo luminescence when bound to the radioactive tracer. The AMP product inhibits the binding of the radioactive tracer to the beads, and the luminescent signal is competed.

The results are calculated as the molar concentrations resulting in 50% inhibition of the substrate cleavage compared to controls samples, and are expressed as $-\log IC_{50}$ (M).

Compounds 101, 103, 104, 106-148, 150-155, 157-206, 208-234, 236-241, 243, 244, 246, 248, 249, 251-258, 260-272, 274-5, 277-285, 287-290, 292-293, 296, 301 and 302 were shown to be efficient inhibitors with $-\log IC_{50}$ (M) above 6.

Example 304

TNFalfa-Release

Human peripheral blood mononuclear cells (PBMC) are isolated from buffy coats. The blood is mixed with saline at a ratio of 1:1, and the PBMC is isolated by the use of Lymphoprep Tubes™ (Nycomed, Norway). The PBMC is suspended in RPMI1640 with 2% foetal calf serum (FCS), pen/strep and 2 mM L-glutamine at a concentration of 5×105 c/ml. The cells are pre-incubated for 30 minutes with the test compounds in 96 well tissue culture plates and stimulated for 18 hours with lipopolysaccharide 1 mg/ml (Sigma). The level of TNF-a is measured in the culture supernatant by enzyme immuno assays using primary and secondary biotinylated antibodies from R&D systems. Results are expressed as pIC50 values calculated from inhibition curves using as positive controls the secretion in LPS stimulated wells and as negative controls the secretion in unstimulated cells.

Compounds 101, 104, 106-138, 140-148, 150-153, 155, 157, 161-164, 168, 170, 171, 176, 177, 182-186, 188-190, 193, 202-206, 208-241, 243, 244, 246, 248, 249, 251-258, 260-275, 277-282, 284, 285, 288-290, 292 and 293 were shown to be efficient inhibitors with $-\log IC_{50}$ (M) above 6.

The invention claimed is:

1. A compound which is 2-{6-[2-(3,5-Dichloro-pyridin-4-yl)-acetyl]-2,3-dimethoxy-phenoxy}-N-propyl-acetamide (compound 208).

2. A pharmaceutical composition comprising the compound according to claim 1 together with a pharmaceutically acceptable vehicle or excipient or pharmaceutically acceptable carrier(s).

3. The compound according to claim 1 or a pharmaceutically acceptable and physiologically cleavable ester thereof, or a pharmaceutically acceptable salt or pharmaceutically acceptable N-oxide thereof.

* * * * *